(12) United States Patent
Numata et al.

(10) Patent No.: US 10,396,295 B2
(45) Date of Patent: Aug. 27, 2019

(54) CONDENSED CYCLIC COMPOUND AND ORGANIC LIGHT-EMITTING DEVICE INCLUDING THE SAME

(71) Applicant: SAMSUNG ELECTRONICS CO., LTD., Suwon-si, Gyeonggi-do (KR)

(72) Inventors: Masaki Numata, Hwaseong-si (KR); Hiroshi Miyazaki, Hwaseong-si (KR); Myungsun Sim, Suwon-si (KR); Saeyoun Lee, Suwon-si (KR); Sooghang Ihn, Hwaseong-si (KR); Soonok Jeon, Seoul (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 181 days.

(21) Appl. No.: 15/466,087

(22) Filed: Mar. 22, 2017

(65) Prior Publication Data

US 2018/0083200 A1    Mar. 22, 2018

(30) Foreign Application Priority Data

Sep. 22, 2016  (KR) ........................ 10-2016-0121457

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 519/00* | (2006.01) | |
| *H01L 51/50* | (2006.01) | |
| *H01L 27/12* | (2006.01) | |

(52) U.S. Cl.
CPC ........ *H01L 51/0072* (2013.01); *C07D 519/00* (2013.01); *C09K 11/06* (2013.01); *H01L 51/0071* (2013.01); *H01L 51/5012* (2013.01); *C09K 2211/1007* (2013.01); *C09K 2211/1048* (2013.01); *H01L 27/1218* (2013.01)

(58) Field of Classification Search
CPC . C09K 11/06; C09K 2211/00; C09K 2211/10; C09K 2211/1007; C09K 2211/1048; C07D 519/00; C07D 519/02; C07D 519/04; H01L 51/0032; H01L 51/005; H01L 51/0071; H01L 51/0072; H01L 51/0074; H01L 51/0073; H01L 51/50; H01L 51/5012; H01L 51/5016; H01L 51/5056; H01L 27/1218
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 2010/0187984 A1 | 7/2010 | Lin et al. | |
| 2015/0021556 A1* | 1/2015 | Xia | ..................... H01L 51/0071 257/40 |
| 2015/0243907 A1 | 8/2015 | Wolleb et al. | |
| 2016/0197286 A1 | 7/2016 | Kawamura et al. | |
| 2017/0062718 A1 | 3/2017 | Numata et al. | |

FOREIGN PATENT DOCUMENTS

| | | |
|---|---|---|
| KR | 10-2015-0056829 A | 5/2015 |
| WO | 2014-092083 A1 | 6/2014 |

* cited by examiner

*Primary Examiner* — Andrew K Bohaty
(74) *Attorney, Agent, or Firm* — Cantor Colburn LLP

(57) ABSTRACT

A condensed cyclic compound represented by Formula 1:

$$Ar_1\text{-}(L_1)_{a1}\text{-}Ar_2 \quad \text{Formula 1}$$

wherein, in Formula 1, a1, $Ar_1$, $Ar_2$, and $L_1$ are the same as described in the specification.

19 Claims, 1 Drawing Sheet

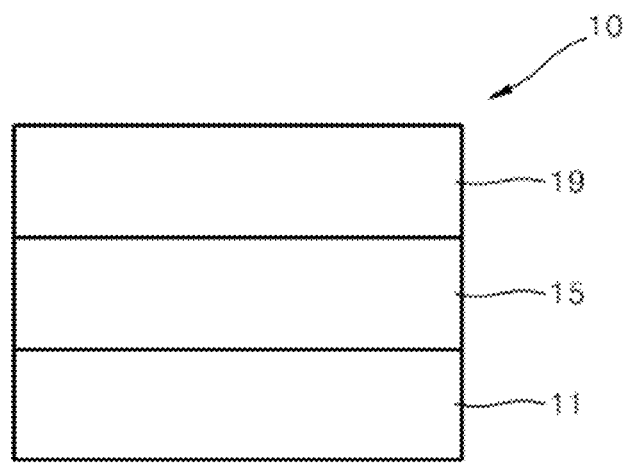

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2016-0121457, filed on Sep. 22, 2016, in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound and an organic light-emitting device including the same.

2. Description of the Related Art

Organic light-emitting devices (OLEDs) are self-emission devices that produce full-color images and have improved characteristics such as a viewing angle, a response time, luminance, a driving voltage, and a response speed.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transition from an excited state to a ground state, thereby generating light.

Various types of organic light emitting devices are known. However, there still remains a need in OLEDs having low driving voltage, high efficiency, high brightness, and long lifespan.

SUMMARY

One or more embodiments relate to a condensed cyclic compound and an organic light-emitting device including the same.

Additional aspects will be set forth in part in the description which follows and, in part, will be apparent from the description, or may be learned by practice of the presented embodiments.

According to one or more embodiments, a condensed cyclic compound is represented by Formula 1:

$$Ar_1-(L_1)_{a1}-Ar_2$$ Formula 1

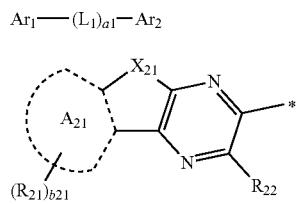

2-1

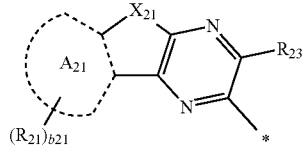

2-2

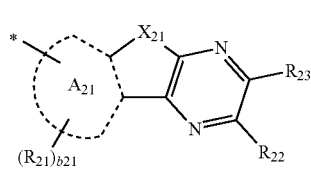

2-3

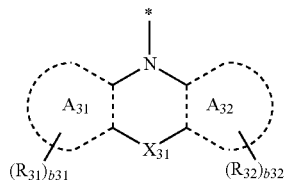

Formula 3-1

In Formulae 1, 2-1 to 2-3, and 3-1, $Ar_1$ may be a group represented by one of Formulae 2-1 to 2-3, $Ar_2$ may be a group represented by Formula 3-1, $L_1$ may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 may be selected from 0, 1, 2, and 3, $X_{21}$ may be selected from O, S, and Se, $X_{31}$ may be selected from a single bond, O, S, $N(R_{33})$, $C(R_{33})(R_{34})$, $Si(R_{33})(R_{34})$, $Ge(R_{33})(R_{34})$, and $P(=O)(R_{33})$, $A_{21}$, $A_{31}$, and $A_{32}$ may each independently be selected from a $C_5$-$C_{30}$ carbocyclic group and a $C_1$-$C_{30}$ heterocyclic group, $R_{21}$ to $R_{23}$ and $R_{31}$ to $R_{34}$ may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ aryl alkyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ heteroaryl alkyl group, a substituted or unsubstituted $C_1$-$C_{60}$ hetero aryloxy group, a substituted or unsubstituted $C_1$-$C_{60}$ hetero arylthio group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_1)(Q_2)(Q_3)$, and $-B(Q_1)(Q_2)$, $R_{22}$ and $R_{23}$ may optionally be linked to form a substituted or unsubstituted $C_5$-$C_{30}$ carbocyclic group or a substituted or unsubstituted $C_1$-$C_{30}$ heterocyclic group, $R_{33}$ and $R_{34}$ may optionally be linked via a first linking group to form a substituted or unsubstituted $C_5$-$C_{30}$ carbocyclic group or a substituted or unsubstituted $C_1$-$C_{30}$ heterocyclic group, b21, b31, and b32 may each independently be selected from 1, 2, 3, 4, 5, 6, 7, and 8, $Q_1$ to $Q_3$ may each independently be selected from:

hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, substituted with at least one selected from deuterium, a $C_1$-$C_{60}$ alkyl group, and a $C_6$-$C_{60}$ aryl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group; and a $C_6$-$C_{60}$ aryl group, substituted with at least one selected from deuterium, a $C_1$-$C_{60}$ alkyl group, and a $C_6$-$C_{60}$ aryl group, and

* indicates a binding site to a neighboring atom.

According to one or more embodiments, an organic light-emitting device includes:
a first electrode;
a second electrode; and
an organic layer disposed between the first electrode and the second electrode,
wherein the organic layer includes an emission layer, and
wherein the organic layer includes at least one condensed cyclic compound represented by Formula 1.

BRIEF DESCRIPTION OF THE DRAWING

These and/or other aspects will become apparent and more readily appreciated from the following description of the embodiments, taken in conjunction with the FIGURE, which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

According to one or more embodiments, a condensed cyclic compound may be represented by Formula 1:

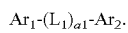   Formula 1

$Ar_1$ in Formula 1 may be a group represented by one of Formulae 2-1 to 2-3:

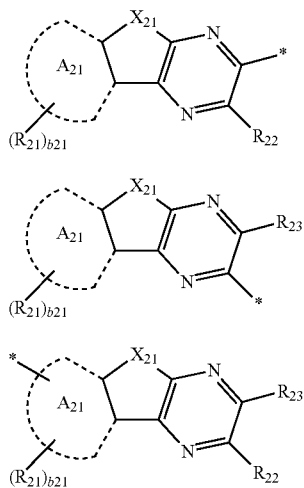

In Formulae 2-1 to 2-3,
$A_{21}$, $X_{21}$, $R_{21}$ to $R_{23}$, and b21 are the same as described below, and
* indicates a binding site to a neighboring atom.

For example, $Ar_1$ in Formula 1 may be represented by Formula 2-3, but embodiments of the present disclosure are not limited thereto.

$L_1$ in Formula 1 may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ in Formula 1 may be selected from:
a phenylene group, a naphthylene group, a fluorenylene group, a phenanthrenylene group, an anthracenylene group, a triphenylenylene group, a pyrenylene group, a chrysenylene group, a pyridinylene group, a pyrazinylene group, a pyrimidinylene group, and a triazinylene group; and
a phenylene group, a naphthylene group, a fluorenylene group, a phenanthrenylene group, an anthracenylene group, a triphenylenylene group, a pyrenylene group, a chrysenylene group, a pyridinylene group, a pyrazinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a triphenylenyl group, a pyrenyl group, a chrysenyl group, a pyridinyl group, a pyrazinyl group, a pyrimidinyl group, and a triazinyl group, but embodiments of the present disclosure are not limited thereto.

In one or more embodiments, $L_1$ in Formula 1 may be selected from:
a phenylene group, a naphthylene group, a pyridinylene group, a pyrazinylene group, a pyrimidinylene group, and a triazinylene group; and
a phenylene group, a naphthylene group, a pyridinylene group, a pyrazinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group, but embodiments of the present disclosure are not limited thereto.

In one or more embodiments, $L_1$ in Formula 1 may be selected from groups represented by Formulae 4-1 to 4-28, but embodiments of the present disclosure are not limited thereto:

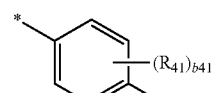   4-1

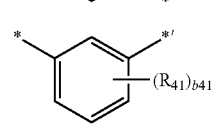   4-2

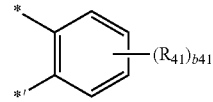   4-3

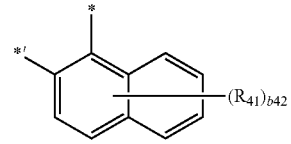   4-4

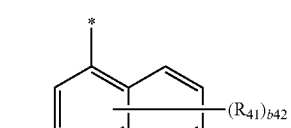   4-5

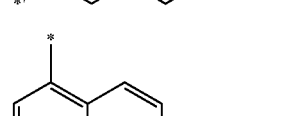   4-6

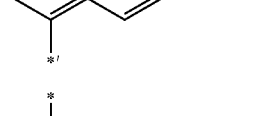   4-7

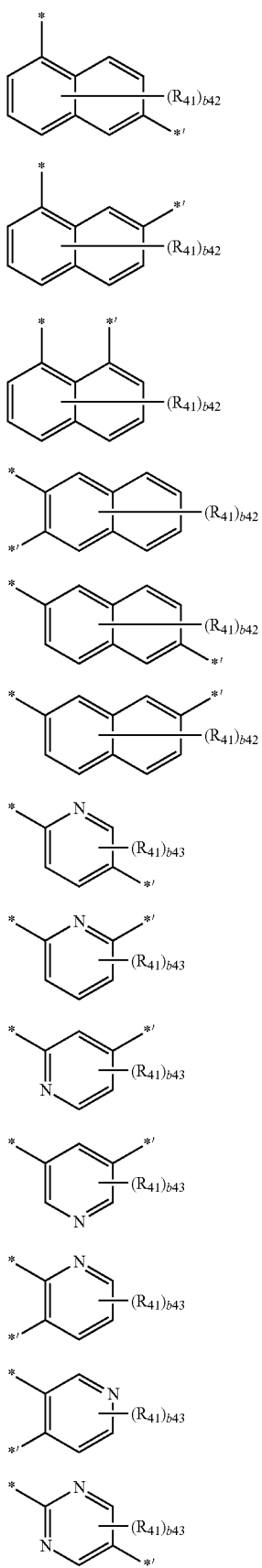

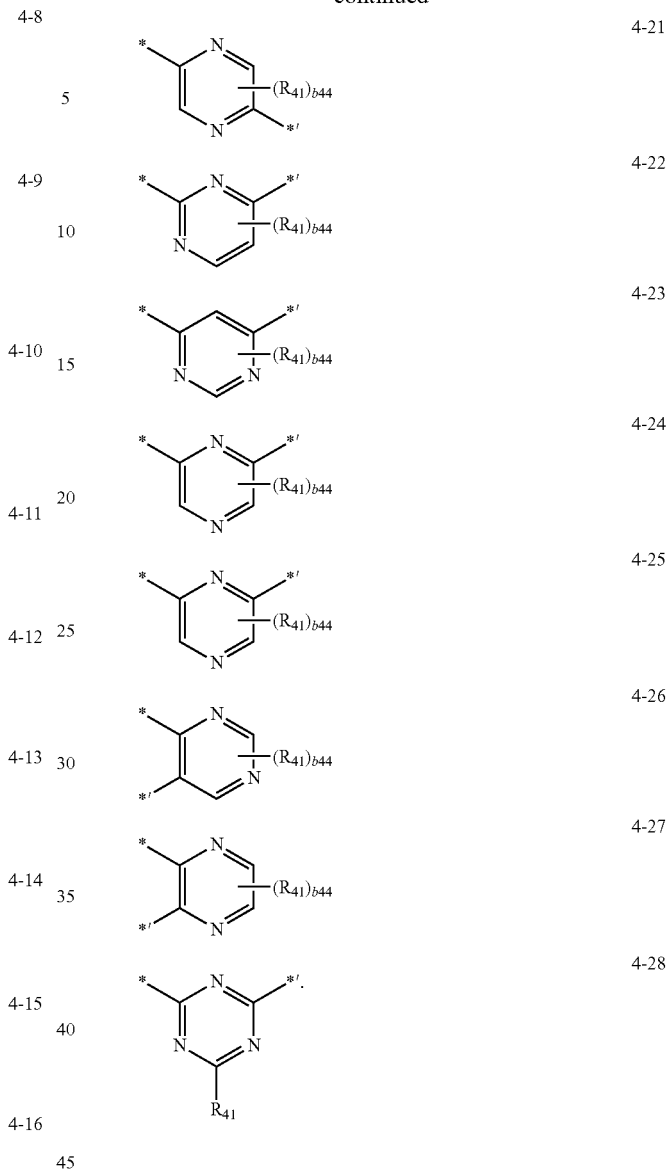

In Formulae 4-1 to 4-28,

R$_{41}$ may be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, and a pyridinyl group, b41 may be selected from 1, 2, 3, and 4, b42 may be selected from 1, 2, 3, 4, 5, and 6, b43 may be selected from 1, 2, and 3, b44 may be 1 or 2, and

* and *' each indicate a binding site to a neighboring atom.

In one or more embodiments, L$_1$ in Formula 1 may be selected from groups represented by Formulae 5-1 to 5-9, but embodiments of the present disclosure are not limited thereto:

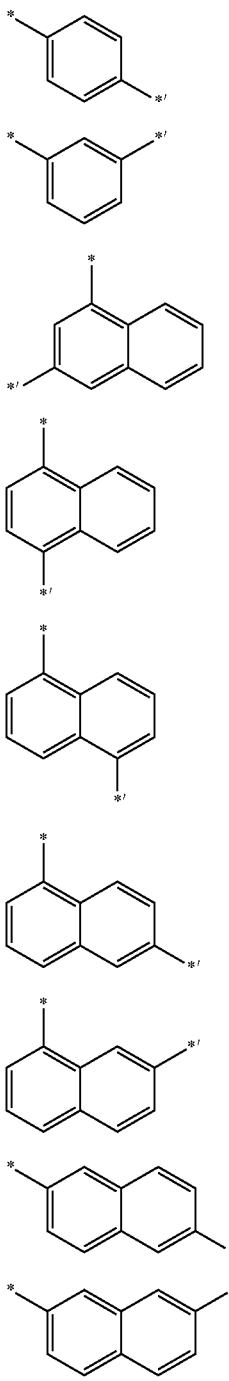

In Formulae 5-1 to 5-9,

* and *' each indicate a binding site to a neighboring atom.

a1 in Formula 1 means the repeating number of groups $L_1$, wherein a1 may be selected from 0, 1, 2, and 3. When a1 is zero, $(L_1)_{a1}$ may be a single bond, and when a1 is two or more, two or more groups $L_1$ may be identical to or different from each other.

For example, a1 in Formula 1 may be 0 or 1, but embodiments of the present disclosure are not limited thereto.

In one or more embodiments, a1 in Formula 1 may be 0, but embodiments of the present disclosure are not limited thereto.

$Ar_2$ in Formula 1 may be a group represented by Formula 3-1:

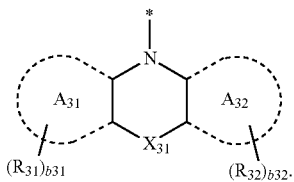

Formula 3-1

In Formula 3-1, $A_{31}$, $A_{32}$, $R_{31}$, $R_{32}$, b31, b32, and $X_{31}$ are the same as described below, and

* indicates a binding site to a neighboring atom.

$X_{21}$ in Formulae 2-1 to 2-3 may be selected from O, S, and Se.

$A_{21}$ in Formulae 2-1 to 2-3 may each independently be selected from a $C_5$-$C_{30}$ carbocyclic group and a $C_1$-$C_{30}$ heterocyclic group.

For example, $A_{21}$ in Formulae 2-1 to 2-3 may be selected from a benzene group, a naphthalene group, a phenanthrene group, a pyrene group, a chrysene group, a triphenylene group, a fluoranthene group, an indene group, a fluorene group, a benzofluorene group, a dibenzofluorene group, a spiro-bifluorene group, a pyridine group, a pyrimidine group, a quinoline group, an isoquinoline group, an indole group, a carbazole group, a benzocarbazole group, a dibenzocarbazole group, a furan group, a benzofuran group, a dibenzofuran group, a naphtho furan group, a benzonaphtho furan group, a dinaphtho furan group, a thiophene group, a benzothiophene group, a dibenzothiophene group, a naphtho thiophene group, a benzonaphtho thiophene group, and a dinaphtho thiophene group, but embodiments of the present disclosure are not limited thereto.

In one or more embodiments, $A_{21}$ in Formulae 2-1 to 2-3 may be selected from a benzene group, a naphthalene group, a phenanthrene group, a pyrimidine group, a quinoline group, and an isoquinoline group, but embodiments of the present disclosure are not limited thereto.

In one or more embodiments, $A_{21}$ in Formulae 2-1 to 2-3 may be selected from a benzene group and a naphthalene group, but embodiments of the present disclosure are not limited thereto.

$R_{21}$ to $R_{23}$ in Formulae 2-1 to 2-3 may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ aryl alkyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ heteroaryl alkyl group, a substituted or unsubstituted $C_1$-$C_{60}$ hetero aryloxy group, a substituted or unsubstituted $C_1$-$C_{60}$ hetero arylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_1$)($Q_2$)($Q_3$), and —B($Q_1$)($Q_2$), and $R_{22}$ and $R_{23}$ may optionally be linked to form a substituted or unsubstituted $C_5$-$C_{30}$ carbocyclic group or a substituted or unsubstituted $C_1$-$C_{30}$ heterocyclic group, wherein $Q_1$ to $Q_3$ may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, substituted with at least one selected from deuterium, a $C_1$-$C_{60}$ alkyl group, and a $C_6$-$C_{60}$ aryl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group; and a $C_6$-$C_{60}$ aryl group, substituted with at least one selected from deuterium, a $C_1$-$C_{60}$ alkyl group, and a $C_6$-$C_{60}$ aryl group, but embodiments of the present disclosure are not limited thereto.

For example, $R_{21}$ to $R_{23}$ in Formulae 2-1 to 2-3 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a pyridinyl group, a pyrimidinyl group, and a triazinyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, a dibenzothiophenyl group, —Si($Q_{31}$)($Q_{32}$)($Q_{33}$), —N($Q_{31}$)($Q_{32}$), and —B($Q_{31}$)($Q_{32}$); and —Si($Q_1$)($Q_2$)($Q_3$), —N($Q_1$)($Q_2$), and —B($Q_1$)($Q_2$), and $R_{22}$ and $R_{23}$ may optionally be linked to form a substituted or unsubstituted $C_5$-$C_{30}$ carbocyclic group or a substituted or unsubstituted $C_1$-$C_{30}$ heterocyclic group, wherein $Q_1$ to $Q_3$ and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, but embodiments of the present disclosure are not limited thereto.

In one or more embodiments, $R_{21}$ to $R_{23}$ in Formulae 2-1 to 2-3 may each independently be selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a fluorenyl group, a pyridinyl group, a pyrimidinyl group, a carbazolyl group, a dibenzofuranyl group, a dibenzothiophenyl group, and —N(Ph)$_2$, and $R_{22}$ and $R_{23}$ may optionally be linked to form a substituted or unsubstituted $C_5$-$C_{30}$ carbocyclic group or a substituted or unsubstituted $C_1$-$C_{30}$ heterocyclic group, but embodiments of the present disclosure are not limited thereto.

b21 in Formulae 2-1 to 2-3 may be selected from 1, 2, 3, 4, 5, 6, 7, and 8. When b21 is two or more, two or more groups $R_{21}$ may be identical to or different from each other.

In one or more embodiments, $Ar_1$ in Formula 1 may be selected from groups represented by Formulae 2-11 to 2-16, but embodiments of the present disclosure are not limited thereto:

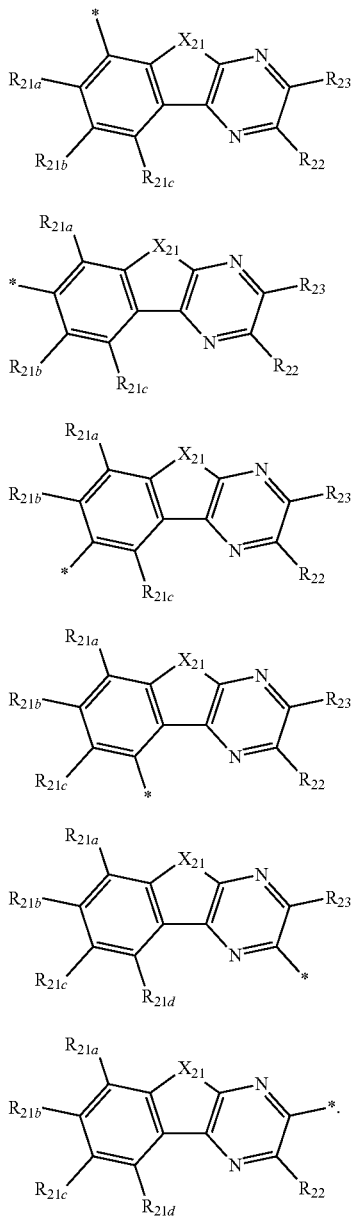

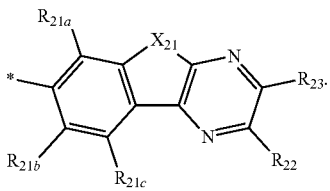

In Formulae 2-11 to 2-16,

X$_{21}$, R$_{22}$, and R$_{23}$ are the same as described in Formulae 2-1 to 2-3, R$_{21a}$ to R$_{21d}$ are each independently the same as described in connection with R$_{21}$ in Formulae 2-1 to 2-3, and

* indicates a binding site to a neighboring atom.

For example, R$_{22}$, R$_{23}$, and R$_{21a}$ to R$_{21d}$ in Formulae 2-11 to 2-16 may each independently be selected from hydrogen, deuterium, —F, —Cl, —Br, —I, a hydroxyl group, a cyano group, a nitro group, a C$_1$-C$_{20}$ alkyl group, a C$_1$-C$_{20}$ alkoxy group, a phenyl group, a fluorenyl group, a pyridinyl group, a pyrimidinyl group, a carbazolyl group, a dibenzofuranyl group, a dibenzothiophenyl group, and —N(Ph)$_2$, and R$_{22}$ and R$_{23}$ may optionally be linked to form a substituted or unsubstituted C$_5$-C$_{30}$ carbocyclic group or a substituted or unsubstituted C$_1$-C$_{30}$ heterocyclic group, but embodiments of the present disclosure are not limited thereto.

In one or more embodiments, Ar$_1$ in Formula 1 may be represented by Formula 2-12, but embodiments of the present disclosure are not limited thereto:

In Formula 2-12,

X$_{21}$, R$_{22}$, and R$_{23}$ are the same as described in Formulae 2-1 to 2-3, R$_{21a}$ to R$_{21c}$ are each independently the same as described in connection with R$_{21}$ in Formulae 2-1 to 2-3, and

* indicates a binding site to a neighboring atom.

For example, R$_{22}$, R$_{23}$, and R$_{21a}$ to R$_{21c}$ in Formula 2-12 may each independently be selected from hydrogen, deuterium, —F, —Cl, —Br, —I, a hydroxyl group, a cyano group, a nitro group, a C$_1$-C$_{20}$ alkyl group, a C$_1$-C$_{20}$ alkoxy group, a phenyl group, a fluorenyl group, a pyridinyl group, a pyrimidinyl group, a carbazolyl group, a dibenzofuranyl group, a dibenzothiophenyl group, and —N(Ph)$_2$, and R$_{22}$ and R$_{23}$ may optionally be linked to form a substituted or unsubstituted C$_5$-C$_{30}$ carbocyclic group or a substituted or unsubstituted C$_1$-C$_{30}$ heterocyclic group, but embodiments of the present disclosure are not limited thereto.

X$_{31}$ in Formula 3-1 may be selected from a single bond, O, S, N(R$_{33}$), C(R$_{33}$)(R$_{34}$), Si(R$_{33}$)(R$_{34}$), Ge(R$_{33}$)(R$_{34}$), and P(=O)(R$_{33}$), and R$_{33}$ and R$_{34}$ are the same as described above.

For example, X$_{31}$ in Formula 3-1 may be selected from a single bond, O, S, N(R$_{33}$), and C(R$_{33}$)(R$_{34}$), but embodiments of the present disclosure are not limited thereto.

A$_{31}$ and A$_{32}$ in Formula 3-1 may each independently be selected from a C$_5$-C$_{30}$ carbocyclic group and a C$_1$-C$_{30}$ heterocyclic group.

For example, A$_{31}$ and A$_{32}$ in Formula 3-1 may each independently be selected from a benzene group, a naphthalene group, a phenanthrene group, a pyrene group, a chrysene group, a triphenylene group, a fluoranthene group, an indene group, a fluorene group, a benzofluorene group, a dibenzofluorene group, a spiro-bifluorene group, a pyridine group, a pyrimidine group, a quinoline group, an isoquinoline group, an indole group, a carbazole group, a benzocarbazole group, a dibenzocarbazole group, a furan group, a benzofuran group, a dibenzofuran group, a naphtho furan group, a benzonaphtho furan group, a dinaphtho furan group, a thiophene group, a benzothiophene group, a dibenzothiophene group, a naphtho thiophene group, a benzonaphtho thiophene group, and a dinaphtho thiophene group, but embodiments of the present disclosure are not limited thereto.

In one or more embodiments, A$_{31}$ and A$_{32}$ in Formula 3-1 may each independently be selected from a benzene group, a naphthalene group, a phenanthrene group, an indene group, a fluorene group, a benzofluorene group, a dibenzofluorene group, a pyridine group, a pyrimidine group, a quinoline group, an isoquinoline group, an indole group, a carbazole group, a benzocarbazole group, a dibenzocarbazole group, a benzofuran group, a dibenzofuran group, a naphtho furan group, a benzonaphtho furan group, a dinaphtho furan group, a benzothiophene group, a dibenzothiophene group, a naphtho thiophene group, a benzonaphtho thiophene group, and a dinaphtho thiophene group, but embodiments of the present disclosure are not limited thereto.

In one or more embodiments, $A_{31}$ in Formula 3-1 may be selected from a benzene group, a naphthalene group, a pyridine group, a pyrimidine group, a quinoline group, and an isoquinoline group, and $A_{32}$ may be selected from a benzene group, a naphthalene group, a phenanthrene group, an indene group, a fluorene group, a benzofluorene group, a dibenzofluorene group, a pyridine group, a pyrimidine group, a quinoline group, an isoquinoline group, an indole group, a carbazole group, a benzocarbazole group, a dibenzocarbazole group, a benzofuran group, a dibenzofuran group, a naphtho furan group, a benzonaphtho furan group, a dinaphtho furan group, a benzothiophene group, a dibenzothiophene group, a naphtho thiophene group, a benzonaphtho thiophene group, and a dinaphtho thiophene group, but embodiments of the present disclosure are not limited thereto.

In one or more embodiments, $A_{31}$ in Formula 3-1 may be selected from a benzene group and a naphthalene group, and $A_{32}$ may be selected from a benzene group, a naphthalene group, a fluorene group, a benzofluorene group, a carbazole group, a benzocarbazole group, a dibenzofuran group, a benzonaphtho furan group, a dibenzothiophene group, and a benzonaphtho thiophene group, but embodiments of the present disclosure are not limited thereto.

In one or more embodiments, $A_{31}$ in Formula 3-1 may be a benzene group, and $A_{32}$ may be selected from a benzene group, a fluorene group, a carbazole group, a dibenzofuran group, and a dibenzothiophene group, but embodiments of the present disclosure are not limited thereto.

$R_{31}$ to $R_{34}$ in Formula 3-1 may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ aryl alkyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ heteroaryl alkyl group, a substituted or unsubstituted $C_1$-$C_{60}$ hetero aryloxy group, a substituted or unsubstituted $C_1$-$C_{60}$ hetero arylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_1$)($Q_2$)($Q_3$), and —B($Q_1$)($Q_2$), $R_{33}$ and $R_{34}$ may optionally be linked via a first linking group to form a substituted or unsubstituted $C_5$-$C_{30}$ carbocyclic group or a substituted or unsubstituted $C_1$-$C_{30}$ heterocyclic group, and $Q_1$ to $Q_3$ may each independently be selected from:

hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, substituted with at least one selected from deuterium, a $C_1$-$C_{60}$ alkyl group, and a $C_6$-$C_{60}$ aryl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group; and a $C_6$-$C_{60}$ aryl group, substituted with at least one selected from deuterium, a $C_1$-$C_{60}$ alkyl group, and a $C_6$-$C_{60}$ aryl group.

For example, $R_{31}$ to $R_{34}$ in Formula 3-1 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a pyridinyl group, a pyrimidinyl group, and a triazinyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, a dibenzothiophenyl group, —Si($Q_{31}$)($Q_{32}$)($Q_{33}$), —N($Q_{31}$)($Q_{32}$), and —B($Q_{31}$)($Q_{32}$); and —Si($Q_1$)($Q_2$)($Q_3$), —N($Q_1$)($Q_2$), and —B($Q_1$)($Q_2$),
wherein $Q_1$ to $Q_3$ and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, but embodiments of the present disclosure are not limited thereto.

In one or more embodiments, $R_{31}$ to $R_{34}$ in Formula 3-1 may each independently be selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a fluorenyl group, a pyridinyl group, a pyrimidinyl group, a carbazolyl group, a dibenzofuranyl group, a dibenzothiophenyl group, and —N(Ph)$_2$, and $R_{33}$ and $R_{34}$ may optionally be linked via a first linking group to form a substituted or unsubstituted $C_5$-$C_{30}$ carbocyclic group or a substituted or unsubstituted $C_1$-$C_{30}$ heterocyclic group, but embodiments of the present disclosure are not limited thereto.

For example, the first linking group may be selected from a single bond, *—O—*', *—S—*', *—[C($R_{35}$)($R_{36}$)]$_{k11}$—*', *—C($R_{35}$)=*', *=C($R_{35}$)—*', *—C($R_{35}$)=C($R_{36}$)—*', *—C(=O)—*', *—C(=S)—*', *—C≡C—*', *—N($R_{35}$)—*', *—P($R_{35}$)—*', *—[Si($R_{35}$)($R_{36}$)]$_{k11}$—*', and *—P($R_{35}$)($R_{36}$)—*', $R_{35}$ and $R_{36}$ are each the same as described in connection with $R_{31}$, k11 may be 1 or 2, and

* and *' each indicate a binding site to a neighboring atom, but embodiments of the present disclosure are not limited thereto.

b31 and b32 in Formula 3-1 may each independently be selected from 1, 2, 3, 4, 5, 6, 7, and 8. When b31 is two or more, two or more groups $R_{31}$ may be identical to or different from each other. When b32 is two or more, two or more groups $R_{32}$ may be identical to or different from each other.

In one or more embodiments, Ar$_2$ in Formula 1 may be one represented by one of Formulae 3-11 to 3-17, but embodiments of the present disclosure are not limited thereto:

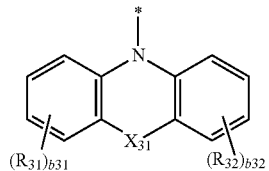

3-11

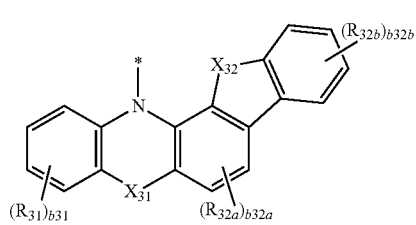

3-12

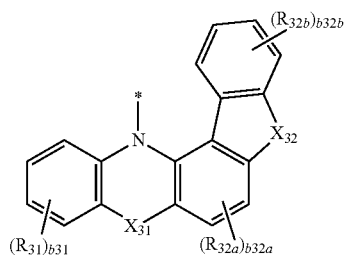

3-13

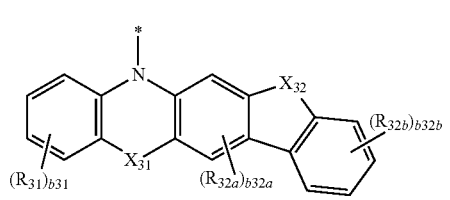

3-14

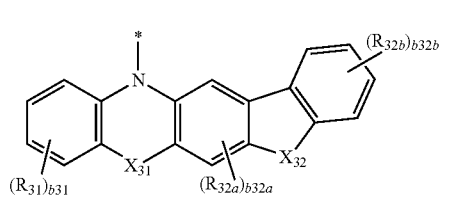

3-15

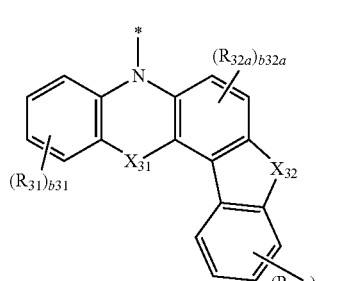

3-16

3-17

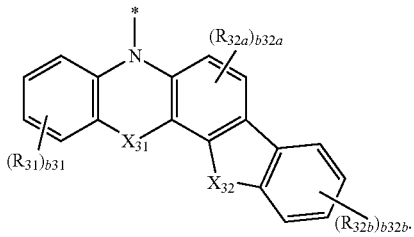

In Formulae 3-11 to 3-17, $X_{31}$, $R_{31}$, $R_{32}$, b31, and b32 are the same as described in Formula 3-1, $X_{32}$ may be selected from O, S, $N(R_{32c})$, and $C(R_{32c})(R_{32d})$, $R_{32a}$ to $R_{32d}$ are each independently the same as described in connection with $R_{32}$ in Formula 3-1, b32a and b32b are each independently the same as described in connection with b32 in Formula 3-1, and

* indicates a binding site to a neighboring atom.

For example, $X_{31}$ in Formulae 3-11 to 3-17 may be selected from a single bond, O, S, $N(R_{33})$, $C(R_{33})(R_{34})$, $Si(R_{33})(R_{34})$, $Ge(R_{33})(R_{34})$, and $P(=O)(R_{33})$, $R_{31}$ to $R_{34}$ and $R_{32a}$ to $R_{32d}$ may each independently be selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a fluorenyl group, a pyridinyl group, a pyrimidinyl group, a carbazolyl group, a dibenzofuranyl group, a dibenzothiophenyl group, and —$N(Ph)_2$, and $R_{33}$ and $R_{34}$ may optionally be linked via a first linking group to form a substituted or unsubstituted $C_5$-$C_{30}$ carbocyclic group or a substituted or unsubstituted $C_1$-$C_{30}$ heterocyclic group, but embodiments of the present disclosure are not limited thereto.

In one or more embodiments, $Ar_2$ in Formulae 3-11 to 3-17 may be one represented by one of Formulae 3-21 to 3-30, but embodiments of the present disclosure are not limited thereto:

3-21

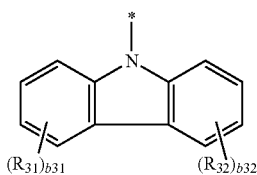

3-22

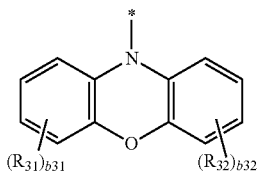

3-23

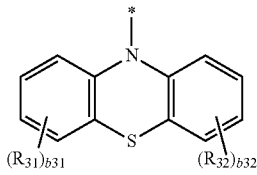

3-24

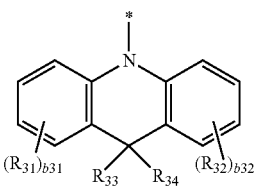

3-25

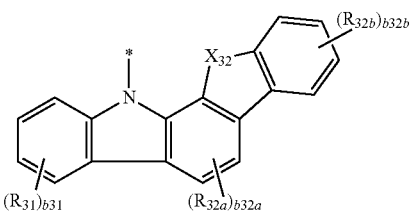

3-26

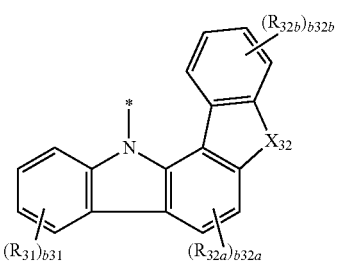

3-27

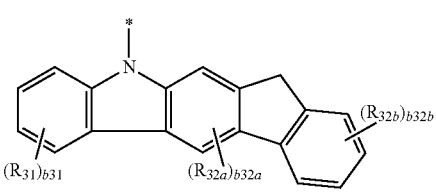

3-28

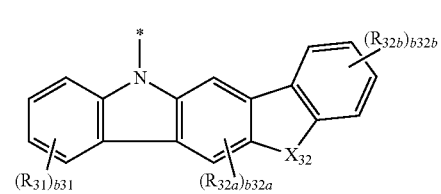

3-29

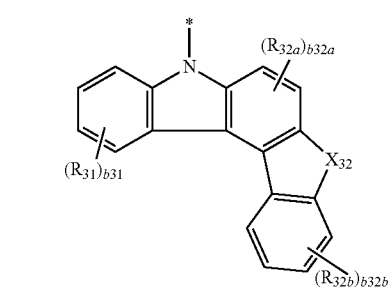

3-30

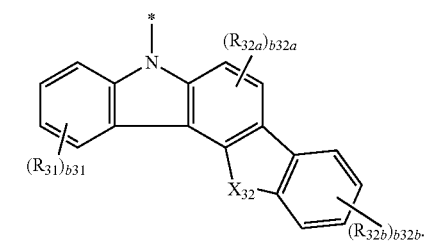

In Formulae 3-21 to 3-30,
$R_{31}$ to $R_{34}$, b31, and b32 are the same as described in Formula 3-1,
$X_{32}$ may be selected from O, S, N($R_{32c}$), and C($R_{32c}$)($R_{32d}$),
$R_{32a}$ to $R_{32d}$ are each independently the same as described in connection with $R_{32}$ in Formula 3-1,
b32a and b32b are each independently the same as described in connection with b32 in Formula 3-1, and
* indicates a binding site to a neighboring atom.

For example, $R_{31}$ to $R_{34}$ and $R_{32a}$ to $R_{32d}$ in Formulae 3-21 to 3-30 may each independently be selected from hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a phenyl group, a fluorenyl group, a pyridinyl group, a pyrimidinyl group, a carbazolyl group, a dibenzofuranyl group, a dibenzothiophenyl group, and —N(Ph)$_2$, and $R_{33}$ and $R_{34}$ may optionally be linked via a first linking group to form a substituted or unsubstituted $C_5$-$C_{30}$ carbocyclic group or a substituted or unsubstituted $C_1$-$C_{30}$ heterocyclic group, but embodiments of the present disclosure are not limited thereto.

In one or more embodiments, the condensed cyclic compound represented by Formula 1 may be represented by one of Formulae 1-1 to 1-10, but embodiments of the present disclosure are not limited thereto:

1-1
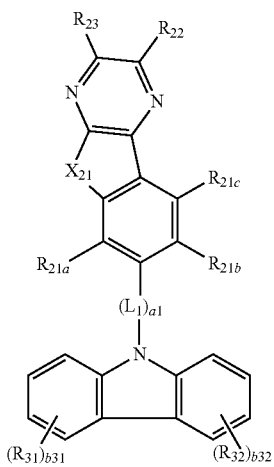

1-2
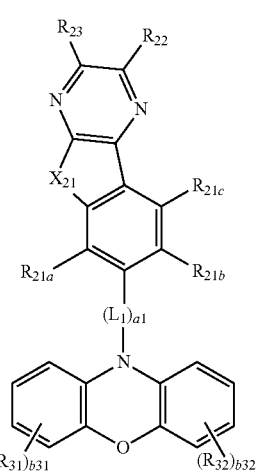

1-3
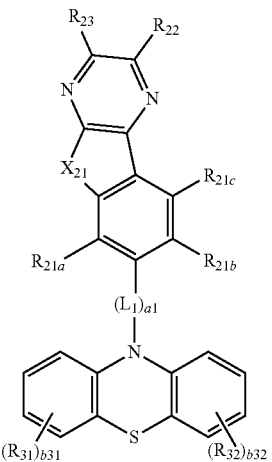

1-4
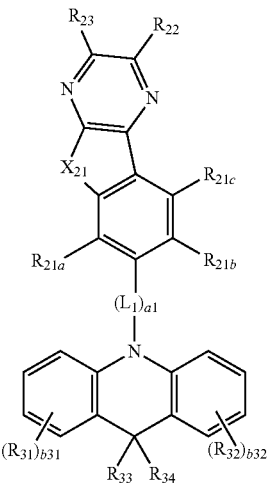

1-5
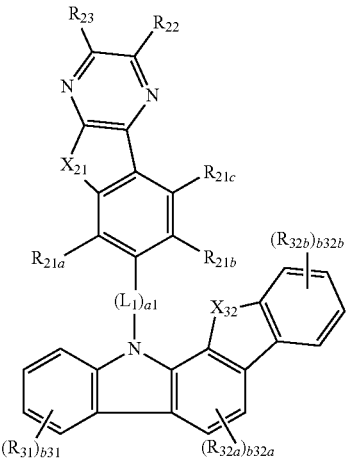

1-6

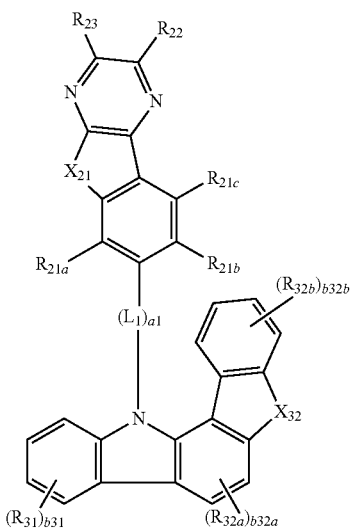

1-7

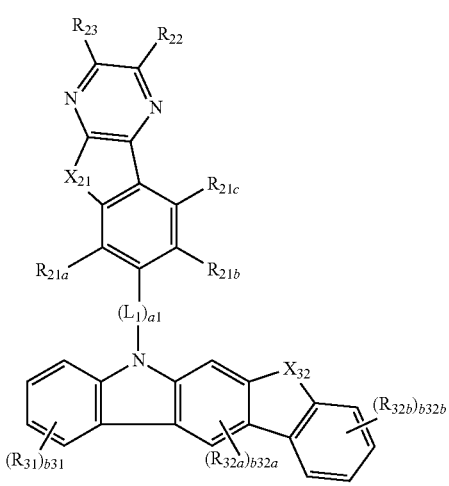

1-8

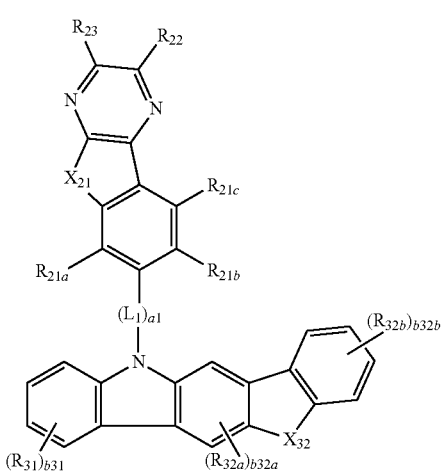

1-9

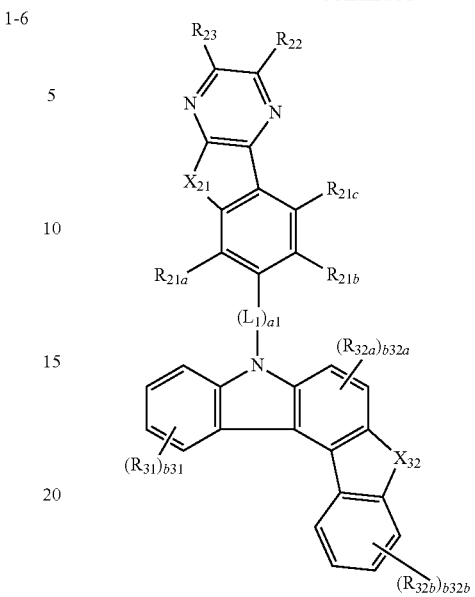

1-10

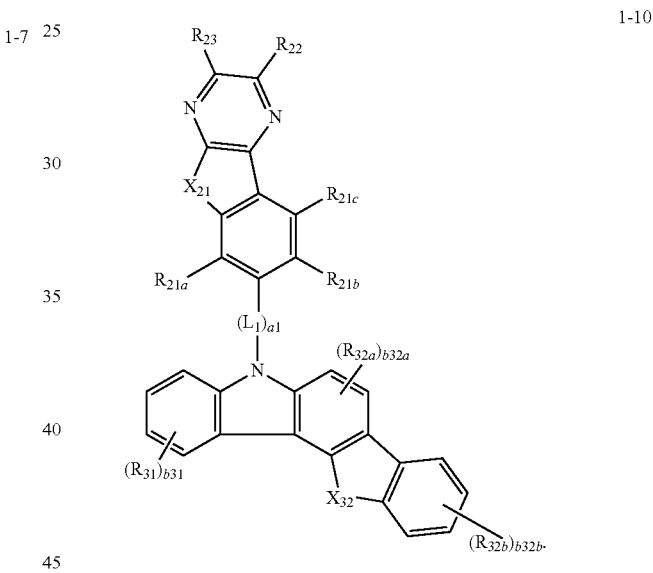

In Formulae 1-1 to 1-10,

L$_1$ and a1 are the same as described in Formula 1,

X$_{21}$, R$_{22}$, and R$_{23}$ are the same as described in Formulae 2-1 to 2-3, R$_{21a}$ to R$_{21c}$ are each independently the same as described in connection with R$_{21}$ in Formulae 2-1 to 2-3, R$_{31}$ to R$_{34}$, b31, and b32 are the same as described in Formula 3-1, X$_{32}$ may be selected from O, S, N(R$_{32c}$), and C(R$_{32c}$)(R$_{32d}$), R$_{32a}$ to R$_{32d}$ are each independently the same as described in connection with R$_{32}$ in Formula 3-1, and b32a and b32b are each independently the same as described in connection with b32 in Formula 3-1.

For example, R$_{22}$, R$_{23}$, R$_{21a}$ to R$_{21c}$, R$_{31}$ to R$_{34}$, and R$_{32a}$ to R$_{32d}$ in Formulae 1-1 to 1-10 may each independently be selected from hydrogen, deuterium, —F, —Cl, —Br, —I, a hydroxyl group, a cyano group, a nitro group, a C$_1$-C$_{20}$ alkyl group, a C$_1$-C$_{20}$ alkoxy group, a phenyl group, a fluorenyl group, a pyridinyl group, a pyrimidinyl group, a carbazolyl group, a dibenzofuranyl group, a dibenzothiophenyl group, and —N(Ph)$_2$, and $R_{33}$ and $R_{34}$ may optionally be linked via a first linking group to form a substituted or unsubstituted $C_5$-$C_{30}$ carbocyclic group or a substituted or unsubstituted $C_1$-$C_{30}$ heterocyclic group, but embodiments of the present disclosure are not limited thereto.

In one or more embodiments, the condensed cyclic compound represented by Formula 1 may be selected from Compounds 1 to 84, but embodiments of the present disclosure are not limited thereto:

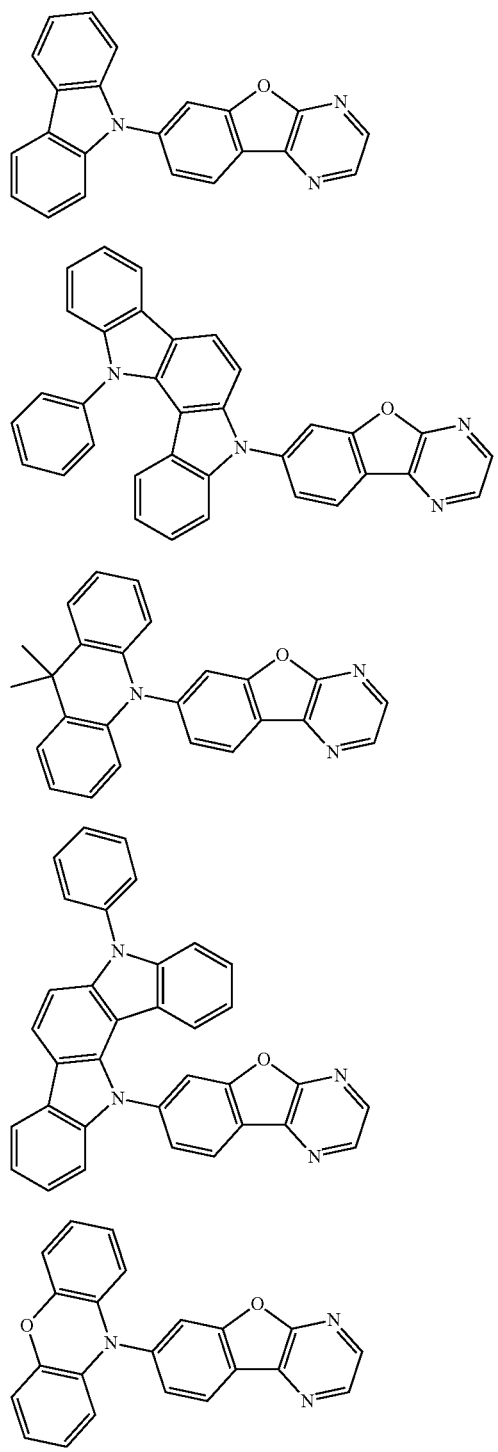

-continued

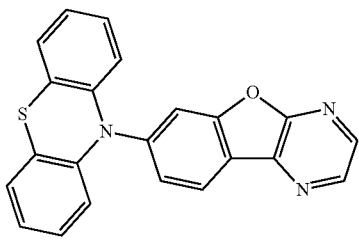

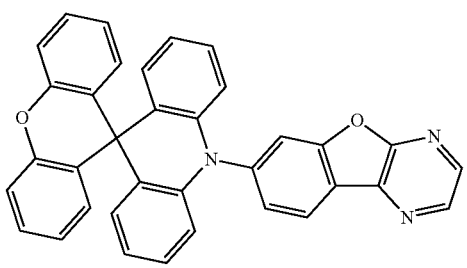

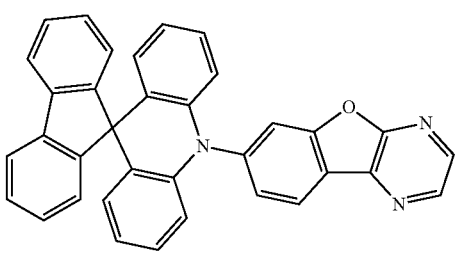

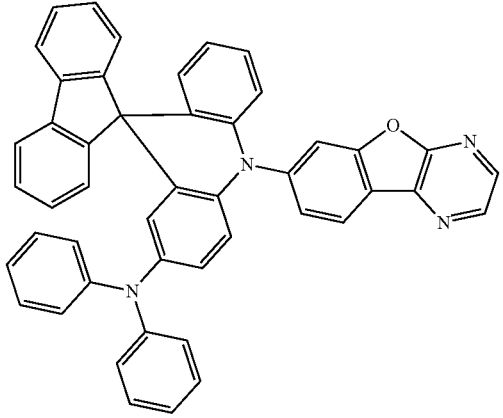

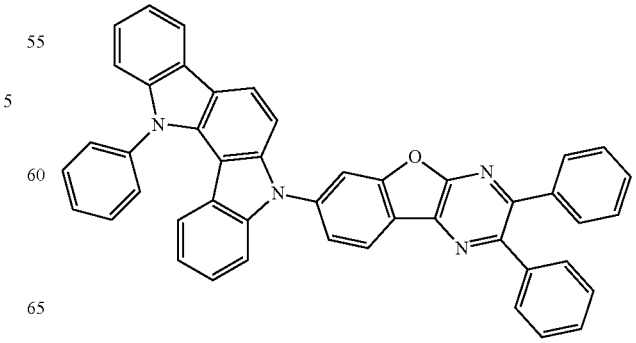

11
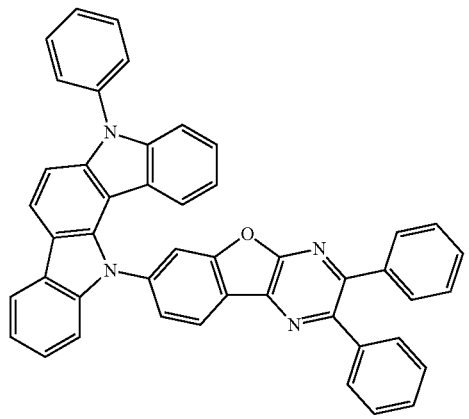
12
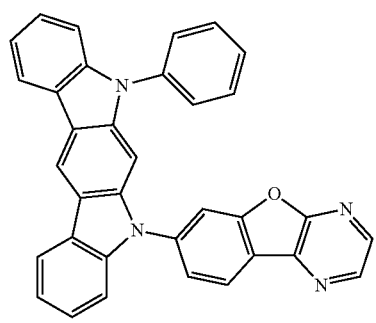
13
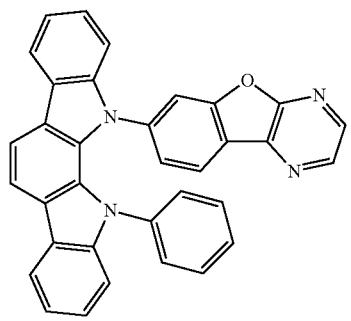
14
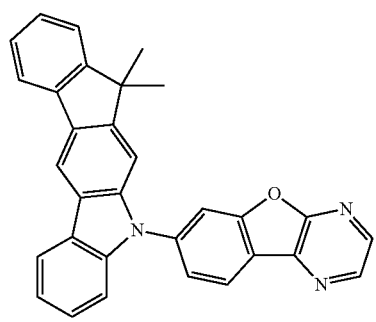
15
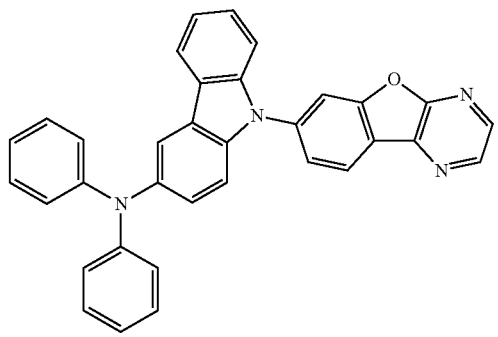
16
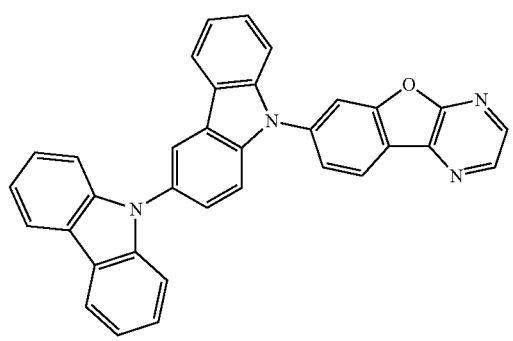
17
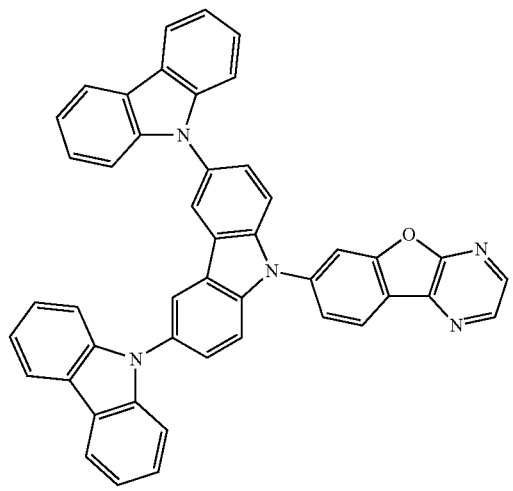
18
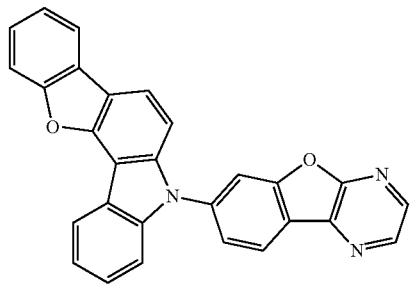

19
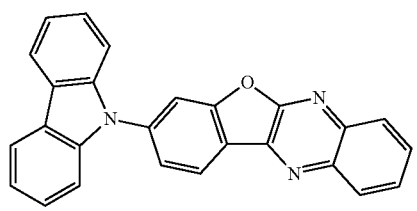
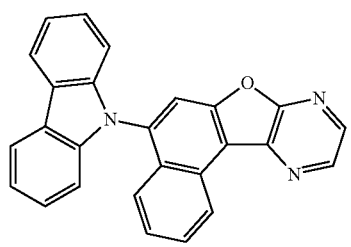
20
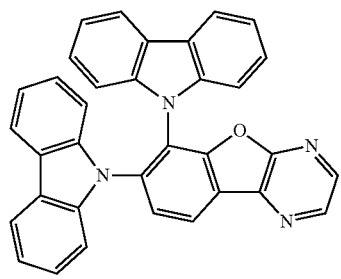
21
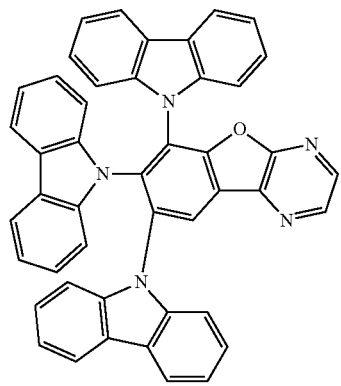
22
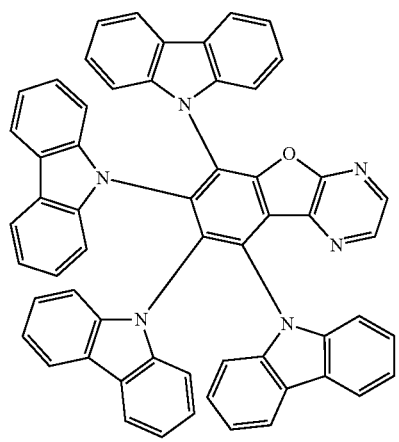
23
24
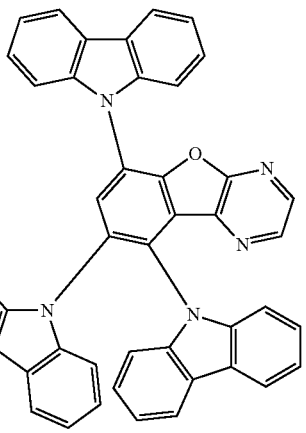
25
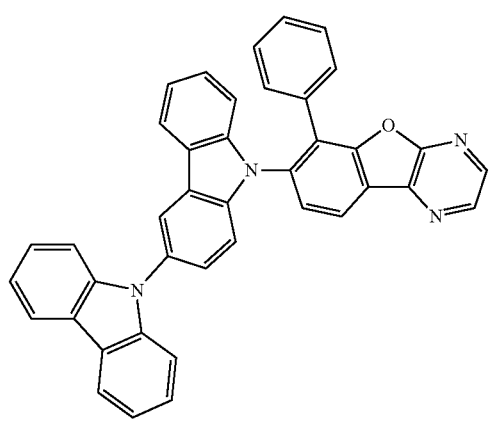
26
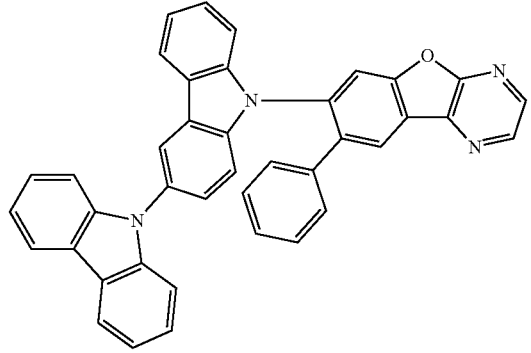
27
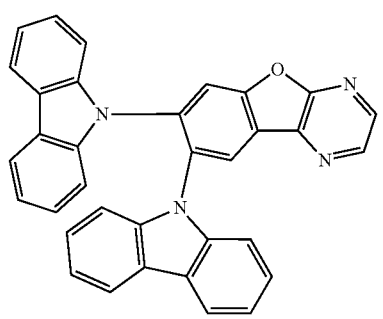

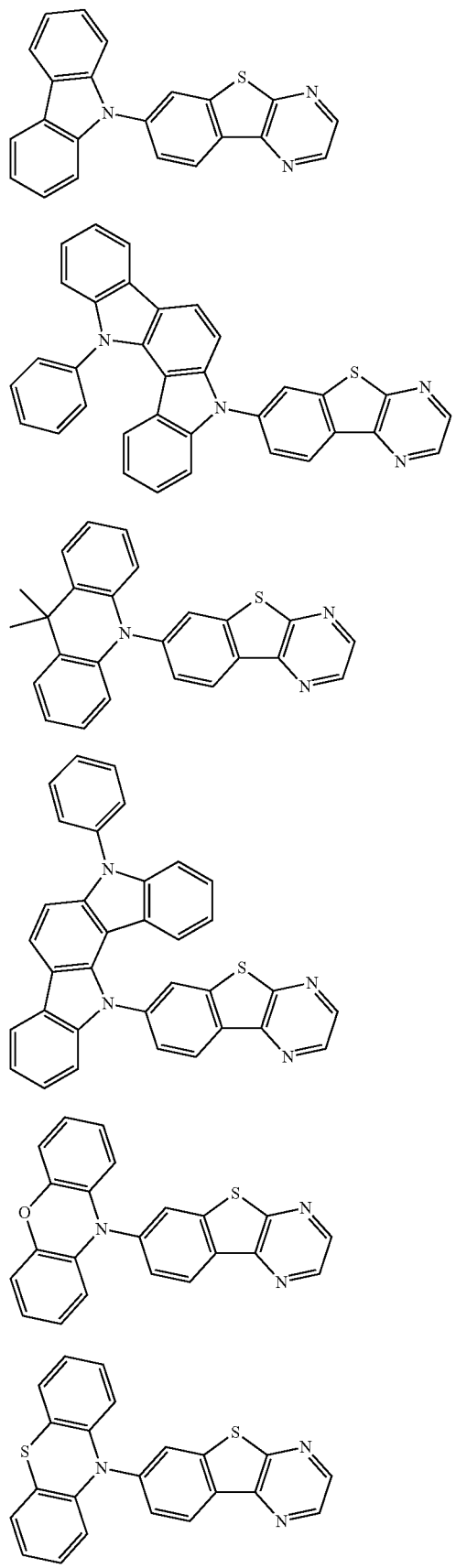
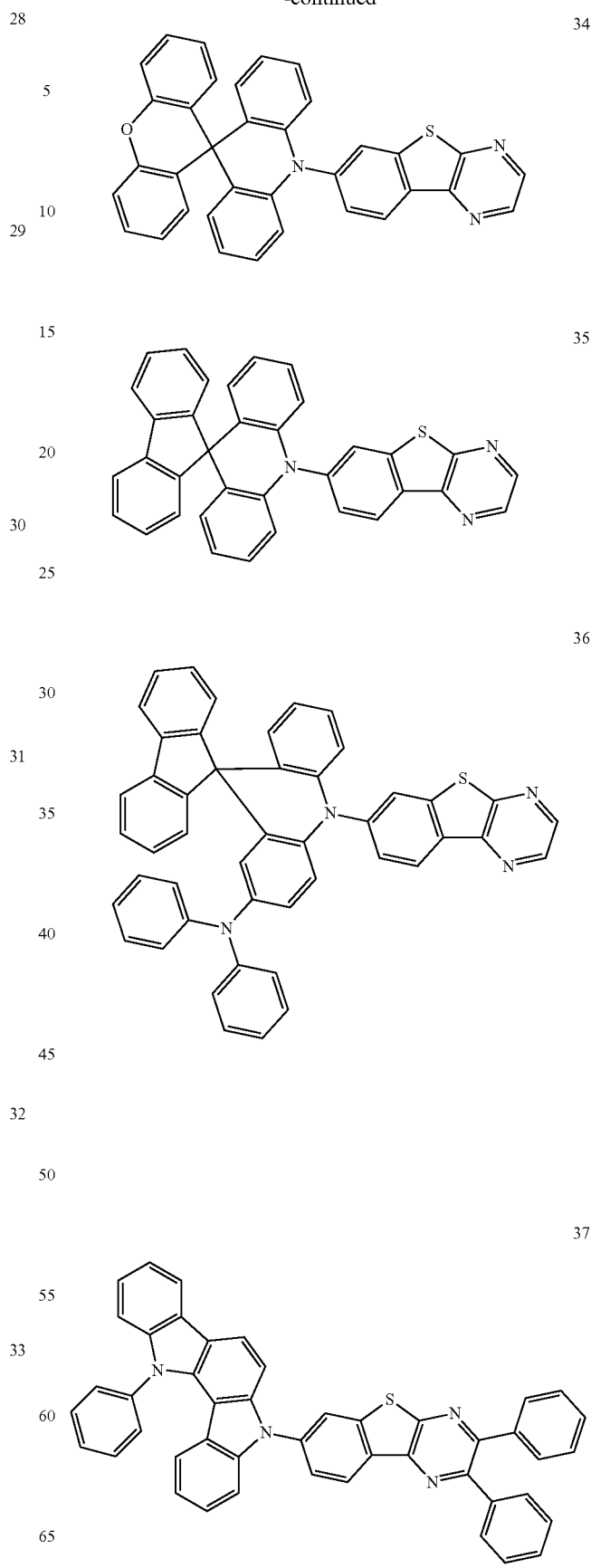

38
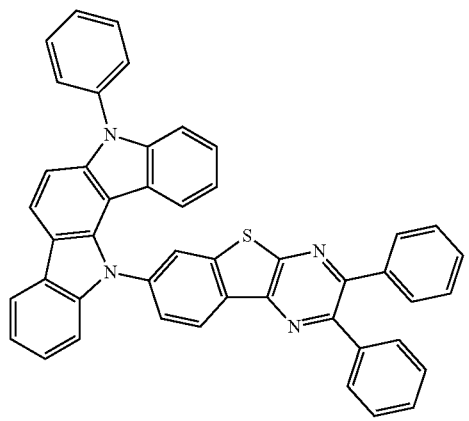
39
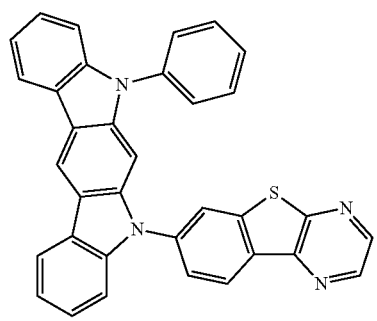
40
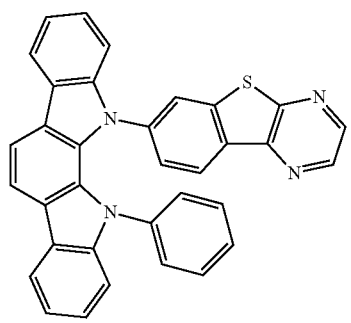
41
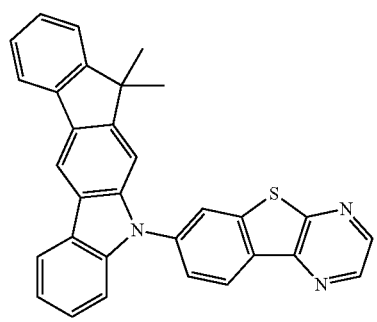
42
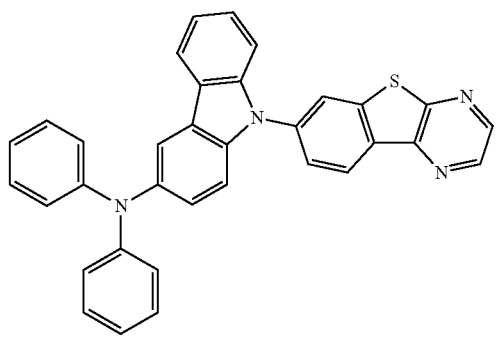
43
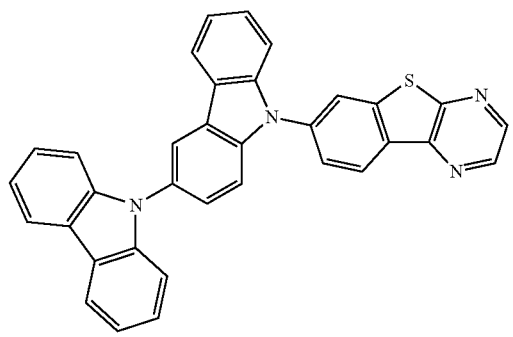
44
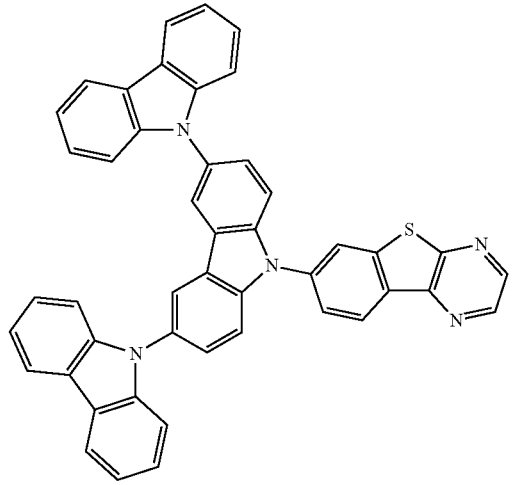
45
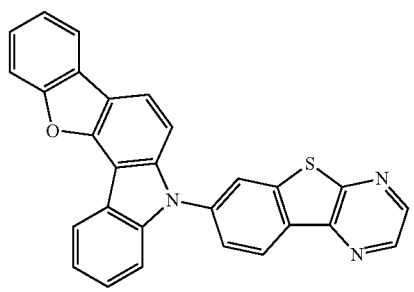

-continued
46
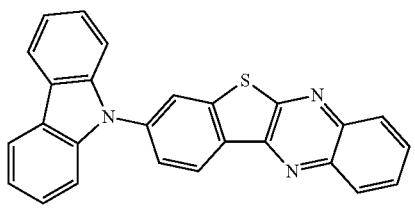
47
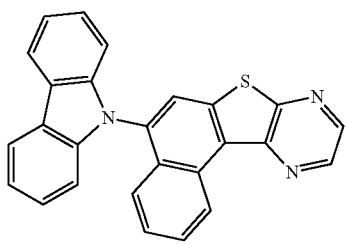
48
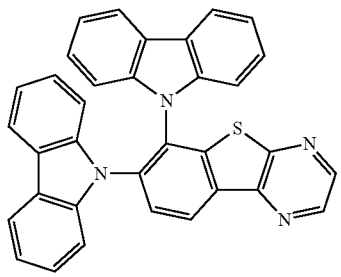
49
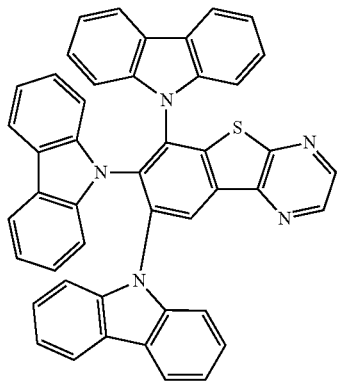
50
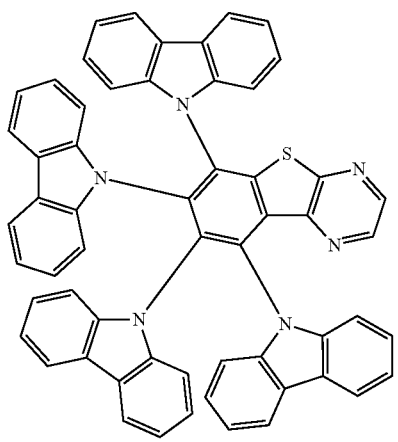
-continued
51
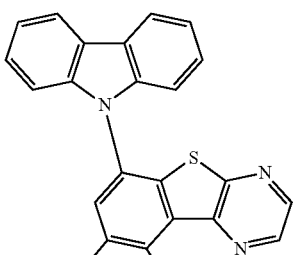
52
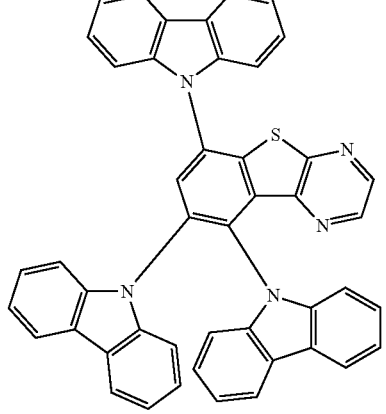
53
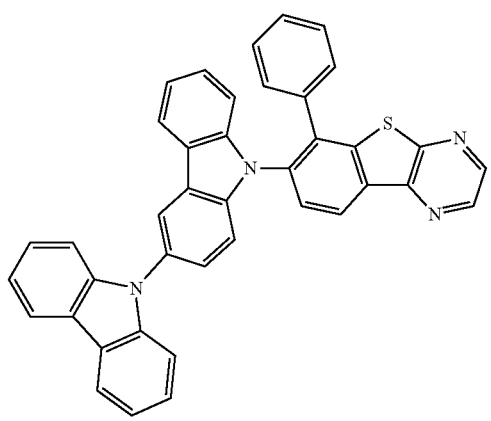
54
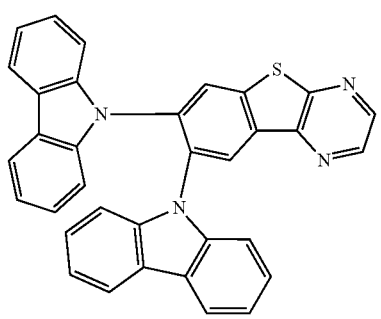

-continued
55
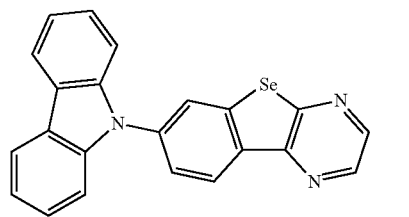
56
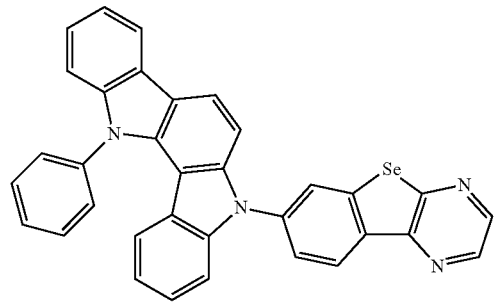
57
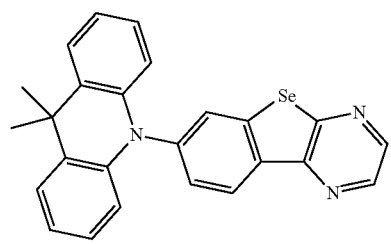
58
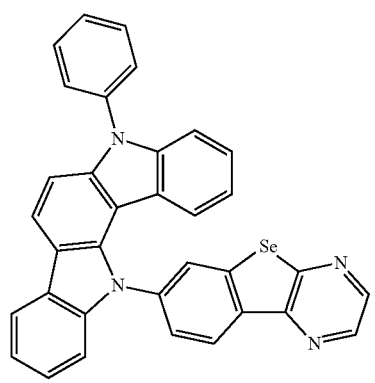
59
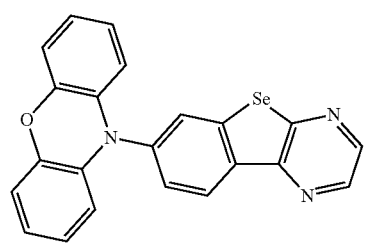
60
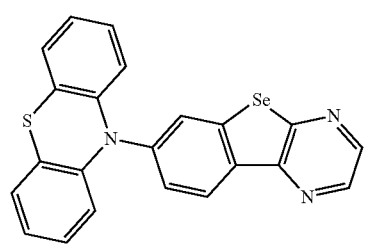
-continued
61
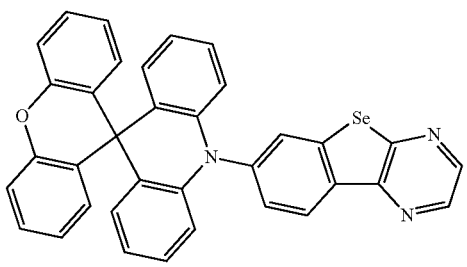
62
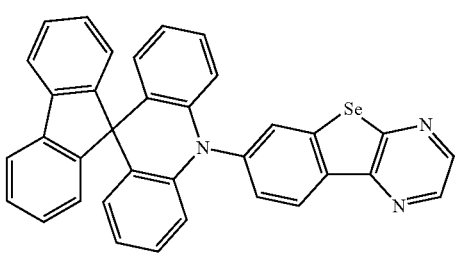
63
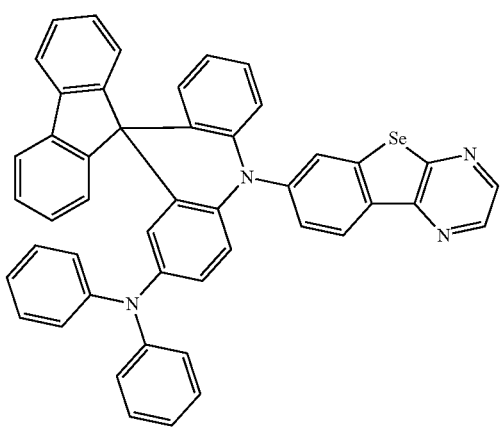
64
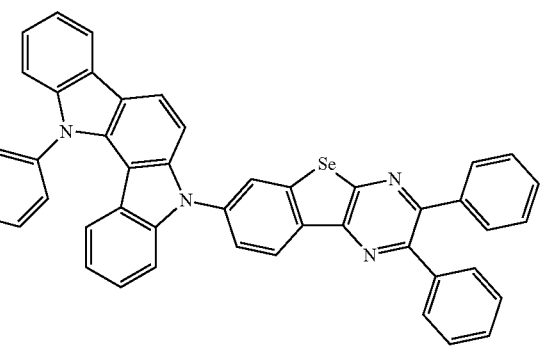

65
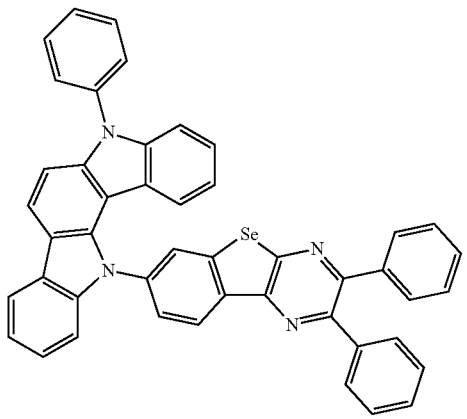
66
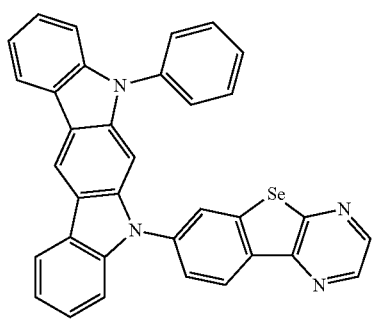
67
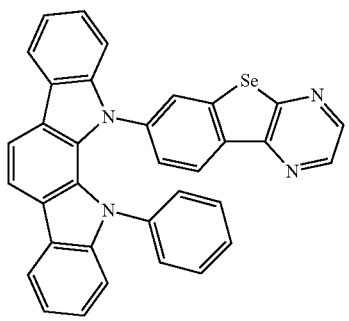
68
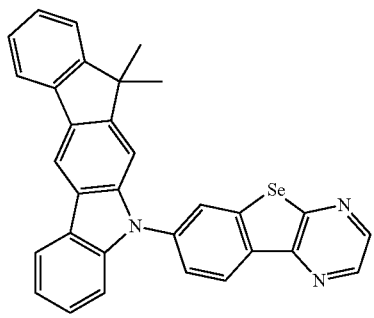
69
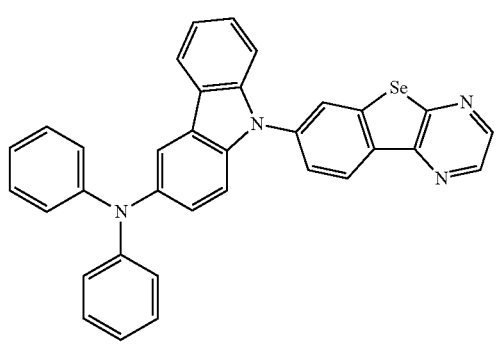
70
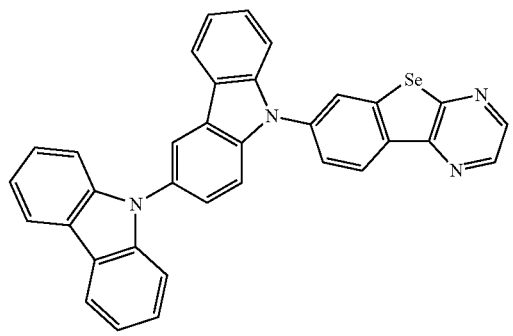
71
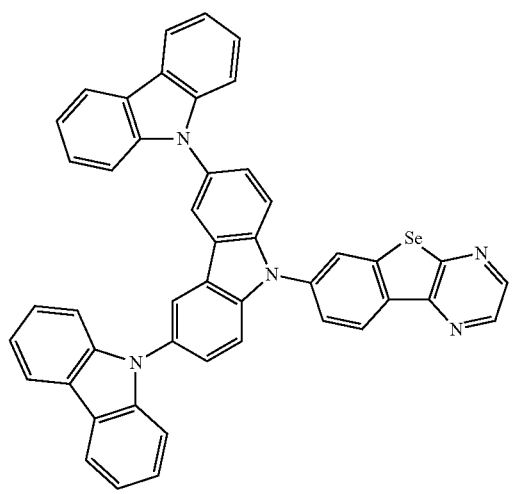
72
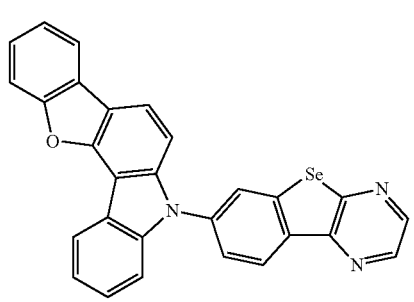

73
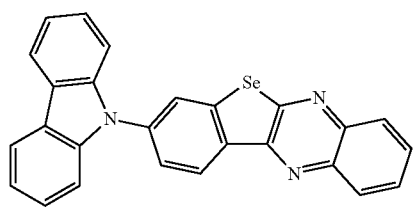
74
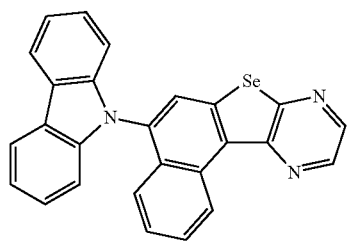
75
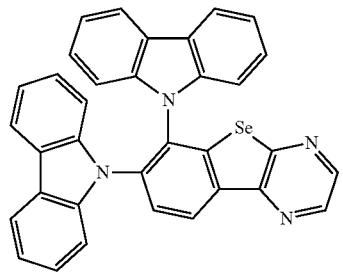
76
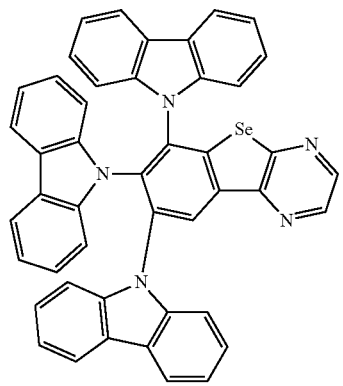
77
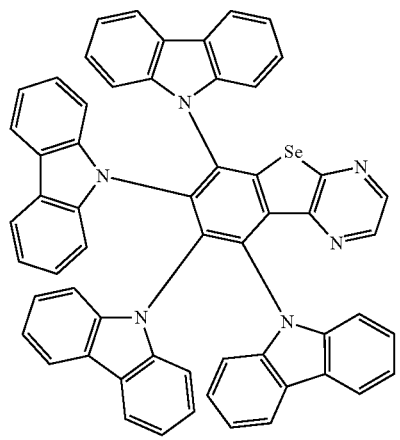
78
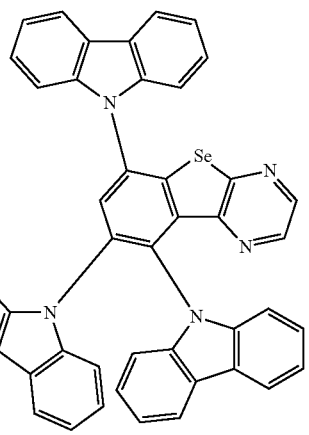
79
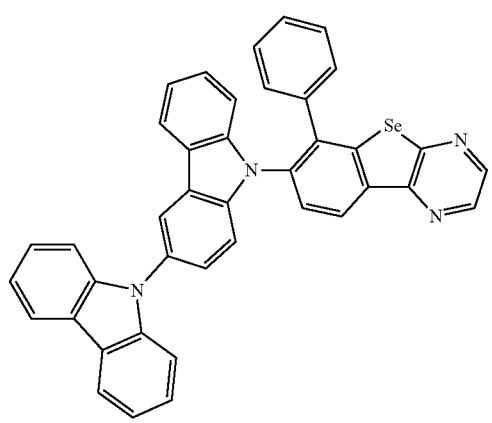
80
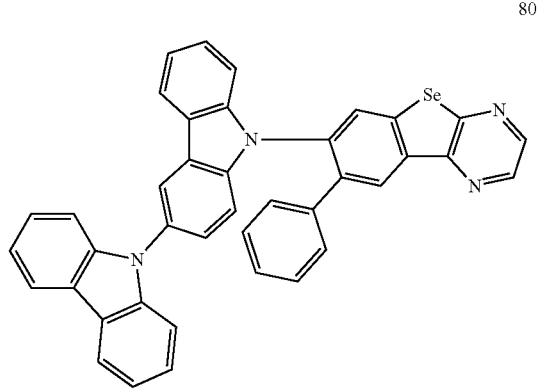
81
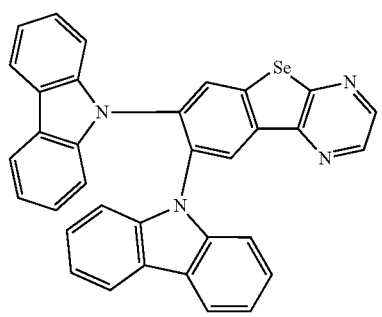

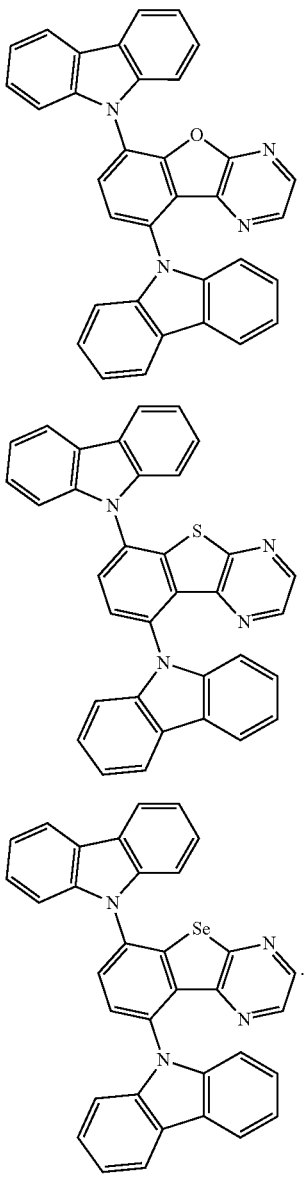

A molecular weight of the condensed cyclic compound represented by Formula 1 may be 1,000 grams per mole (g/mol) or less. For example, the molecular weight of the condensed cyclic compound represented by Formula 1 may be 800 g/mol or less, may be 700 g/mol or less, or may be 600 g/mol or less, but embodiments of the present disclosure are not limited thereto. For example, the molecular weight of the condensed cyclic compound represented by Formula 1 may be 400 g/mol to 800 g/mol, may be 400 g/mol to 700 g/mol, or may be 400 g/mol to 600 g/mol. While not wishing to be bound by theory, it is understood that when the molecular weight of the condensed cyclic compound represented by Formula 1 is within this range, a deposition temperature thereof may be relatively low.

The deposition temperature of the condensed cyclic compound represented by Formula 1 may be lower than that of another compound having a molecular weight similar thereto. Accordingly, an organic light-emitting device including the condensed cyclic compound represented by Formula 1 may be more easily manufactured through a deposition process. For example, the deposition temperature of the condensed cyclic compound represented by Formula 1 may be 200° C. or less, or may be 180° C. or less.

The condensed cyclic compound represented by Formula 1 may have high thermal stability. In particular, the condensed cyclic compound represented by Formula 1 may not include a cyano group, thereby improving the thermal stability of the condensed cyclic compound represented by Formula 1.

The condensed cyclic compound represented by Formula 1 may satisfy Equation 1:

$$0 \text{ electron volts (eV)} \leq \Delta E_{ST} \leq 0.3 \text{ electron volts (eV)}. \quad \text{Equation 1}$$

In Equation 1, $\Delta E_{ST}$ is a difference between the lowest excitation singlet energy level ($E_{S1}$) of the condensed cyclic compound represented by Formula 1 and the lowest excitation triplet energy level ($E_{T1}$) of the condensed cyclic compound represented by Formula 1.

Since the condensed cyclic compound represented by Formula 1 satisfies Equation 1, reverse intersystem crossing may occur even at a low temperature (for example, room temperature (ambient temperature)). Accordingly, an organic light-emitting device including the condensed cyclic compound represented by Formula 1 may provide improved light emission efficiency.

The condensed cyclic compound represented by Formula 1 may include a group acting as an electron withdrawing group and represented by one of Formulae 2-1 to 2-3, and a group acting as an electron donating group and represented by Formula 3-1. Accordingly, in the condensed cyclic compound represented by Formula 1, the highest occupied molecular orbital (HOMO) and the lowest unoccupied molecular orbital (LUMO) may be spatially separated from each other, resulting in a reduction in $\Delta E_{ST}$. Thus, reverse intersystem crossing may occur in the condensed cyclic compound represented by Formula 1 even at a low temperature.

Also, the condensed cyclic compound represented by Formula 1 essentially includes at least two nitrogen atoms at specific locations, like a group represented by one of Formulae 2-1 to 2-3. Accordingly, since the condensed cyclic compound represented by Formula 1 has a relatively large radiative rate constant, an organic light-emitting device including the condensed cyclic compound represented by Formula 1 may increase a quantum yield.

Furthermore, since the condensed cyclic compound represented by Formula 1 has an electron withdrawing group represented by one of Formulae 2-1 to 2-3, a molecular weight thereof may be relatively low. Although a molecular weight is not an absolute factor in determining a deposition temperature, a low molecular weight may act as a factor in reducing a deposition temperature. Thus, an organic light-emitting device may be manufactured at a low temperature.

Synthesis methods of the condensed cyclic compound represented by Formula 1 may be recognizable by one of ordinary skill in the art by referring to Synthesis Examples provided below.

Accordingly, the condensed cyclic compound represented by Formula 1 is suitable for use in an organic layer of an organic light-emitting device, for example, for use as a dopant in an emission layer of the organic layer. According to one or more embodiments, an organic light-emitting device includes:

a first electrode;

a second electrode; and an organic layer disposed between the first electrode and the second electrode, wherein the organic layer includes an emission layer, and wherein the organic layer includes at least one condensed cyclic compound represented by Formula 1.

The organic light-emitting device may have, due to inclusion of an organic layer including the condensed cyclic compound represented by Formula 1, improved light emission efficiency, color purity, and lifespan characteristics.

The condensed cyclic compound represented by Formula 1 may be used between a pair of electrodes of an organic light-emitting device. For example, the condensed cyclic compound represented by Formula 1 may be included in the emission layer.

In one or more embodiments, the emission layer may include a host A and a condensed cyclic compound represented by Formula 1. In the emission layer, an amount of the host A may be greater than an amount of the condensed cyclic compound represented by Formula 1 (that is, the condensed cyclic compound represented by Formula 1 is included as a dopant). Also, the condensed cyclic compound represented by Formula 1 may emit fluorescence and/or delayed fluorescence.

In this case, the host A and the condensed cyclic compound represented by Formula 1 may satisfy Equation 2:

$$E(H_A)_{S1} > E_{S1}. \qquad \text{Equation 2}$$

In Equation 2, $E(H_A)_{S1}$ refers to the lowest excitation singlet energy level of the host A, and $E_{S1}$ refers to the lowest excitation singlet energy level of the condensed cyclic compound represented by Formula 1.

When the condensed cyclic compound represented by Formula 1 satisfies Equation 1 and the condensed cyclic compound represented by Formula 1 and the host A satisfy Equation 2, fluorescence and/or delayed fluorescence may be emitted from the condensed cyclic compound represented by Formula 1. Therefore, light emission efficiency of an organic light-emitting device including the condensed cyclic compound represented by Formula 1 and the host A may be improved.

For example, the host A may be a host material to be described below, but embodiments of the present disclosure are not limited thereto.

In one or more embodiments, the emission layer may include a condensed cyclic compound represented by Formula 1 and a fluorescent dopant A. In the emission layer, an amount of the condensed cyclic compound represented by Formula 1 may be greater than an amount of the fluorescent dopant A (that is, the condensed cyclic compound represented by Formula 1 is included as a host). Also, the fluorescent dopant A may emit fluorescence.

In this case, the condensed cyclic compound represented by Formula 1 and the fluorescent dopant A may satisfy Equation 3:

$$E_{S1} > E(F_A)_{S1}. \qquad \text{Equation 3}$$

In Equation 3, $E_{S1}$ refers to a lowest excitation singlet energy level of the condensed cyclic compound represented by Formula 1, and $E(F_A)_{S1}$ refers to a lowest excitation singlet energy level of the fluorescent dopant A.

When the condensed cyclic compound represented by Formula 1 satisfies Equation 1 and the condensed cyclic compound represented by Formula 1 and the fluorescent dopant A satisfy Equation 3, Förster energy transfer from the condensed cyclic compound represented by Formula 1 to the fluorescent dopant A may be accelerated. Accordingly, light emission efficiency of an organic light-emitting device including the condensed cyclic compound represented by Formula 1 and the fluorescent dopant A may be improved.

For example, the fluorescent dopant A may be a dopant material to be described below, but embodiments of the present disclosure are not limited thereto.

In one or more embodiments, the emission layer may include a host B, a condensed cyclic compound represented by Formula 1, and a fluorescent dopant B.

In the emission layer, an amount of the host B may be greater than each of an amount of the condensed cyclic compound represented by Formula 1 and an amount of the fluorescent dopant B (that is, the condensed cyclic compound represented by Formula 1 is included as a host). For example, in the emission layer, an amount of the condensed cyclic compound represented by Formula 1 may be greater than an amount of the fluorescent dopant B, but embodiments of the present disclosure are not limited thereto.

Also, the fluorescent dopant B may emit fluorescence.

In this case, the host B, the condensed cyclic compound represented by Formula 1, and the fluorescent dopant B may satisfy Equation 4:

$$E(H_B)_{S1} > E_{S1} > E(F_B)_{S1}. \qquad \text{Equation 4}$$

In Equation 4, $E(H_B)_{S1}$ refers to the lowest excitation singlet energy level of the host B, $E_{S1}$ refers to the lowest excitation singlet energy level of the condensed cyclic compound represented by Formula 1, and $E(F_B)_{S1}$ refers to the lowest excitation singlet energy level of the fluorescent dopant B.

While not wishing to be bound by theory, it is understood that when the condensed cyclic compound represented by Formula 1 satisfies Equation 1, and the host B, the condensed cyclic compound represented by Formula 1, and the fluorescent dopant B satisfy Equation 4, Förster energy transfer from the condensed cyclic compound represented by Formula 1 to the fluorescent dopant B may be accelerated. Accordingly, light emission efficiency of an organic light-emitting device including the host B, the condensed cyclic compound represented by Formula 1, and the fluorescent dopant B may be improved.

In this case, the host B, the condensed cyclic compound represented by Formula 1, and the fluorescent dopant B may further satisfy Equation 5:

$$E(H_B)_{T1} > E_{T1}. \qquad \text{Equation 5}$$

In Equation 5, $E(H_B)_{T1}$ refers to the lowest excitation triplet energy level of the host B, and $E_{T1}$ refers to the lowest excitation triplet energy level of the condensed cyclic compound represented by Formula 1.

For example, the host B may be a host material to be described below, but embodiments of the present disclosure are not limited thereto.

For example, the fluorescent dopant B may be a dopant material to be described below, but embodiments of the present disclosure are not limited thereto.

The expression "(an organic layer) includes at least one condensed cyclic compound" as used herein may include an embodiment in which "(an organic layer) includes identical compounds represented by Formula 1" and an embodiment in which "(an organic layer) includes two or more different condensed cyclic compounds represented by Formula 1".

For example, the organic layer may include, as the condensed cyclic compound, only Compound 1. In this regard, Compound 1 may be included in an emission layer of the organic light-emitting device. In one or more embodiments, the organic layer may include, as the condensed cyclic compound, Compound 1 and Compound 2. In this regard, Compound 1 and Compound 2 may be included in an identical layer (for example, Compound 1 and Compound 2 all may be included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

In one or more embodiments, in the organic light-emitting device, the first electrode may be an anode, and the second electrode may be a cathode, and the organic layer may further include a hole transport region disposed between the first electrode and the emission layer and an electron transport region disposed between the emission layer and the second electrode, and the hole transport region may include a hole injection layer, a hole transport layer, an electron blocking layer, or any combination thereof, and the electron transport region may include a hole blocking layer, an electron transport layer, an electron injection layer, or any combination thereof.

The term "organic layer" as used herein refers to a single layer and/or a plurality of layers disposed between the first electrode and the second electrode of the organic light-emitting device. The "organic layer" may include, in addition to an organic compound, an organometallic complex including metal.

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary depending on a material that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary depending on the material used to form the hole injection layer, and the structure and thermal properties of the hole injection layer. For example, a coating speed may be from about 2,000 revolutions per minute (rpm) to about 5,000 rpm, or may be 3,000 rpm to about 4,000 rpm, and a temperature at which a heat treatment is performed to remove a solvent after coating may be from about 80° C. to about 200° C., or may be about 120° C. to about 180° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

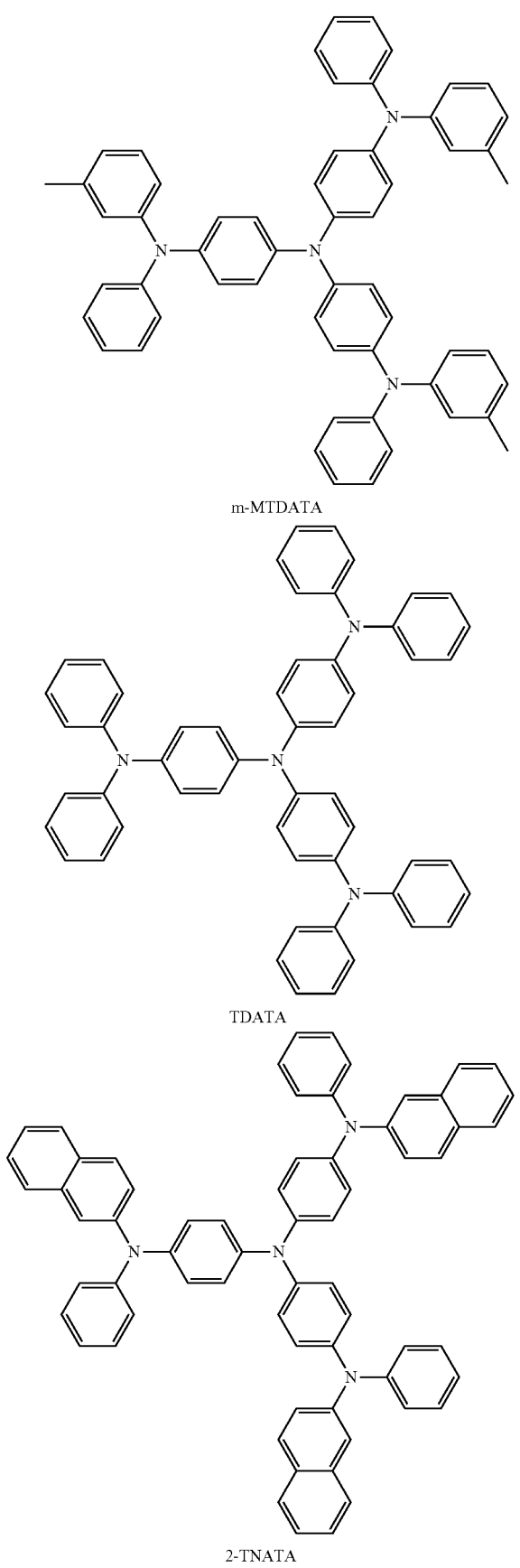
m-MTDATA
TDATA
2-TNATA
-continued
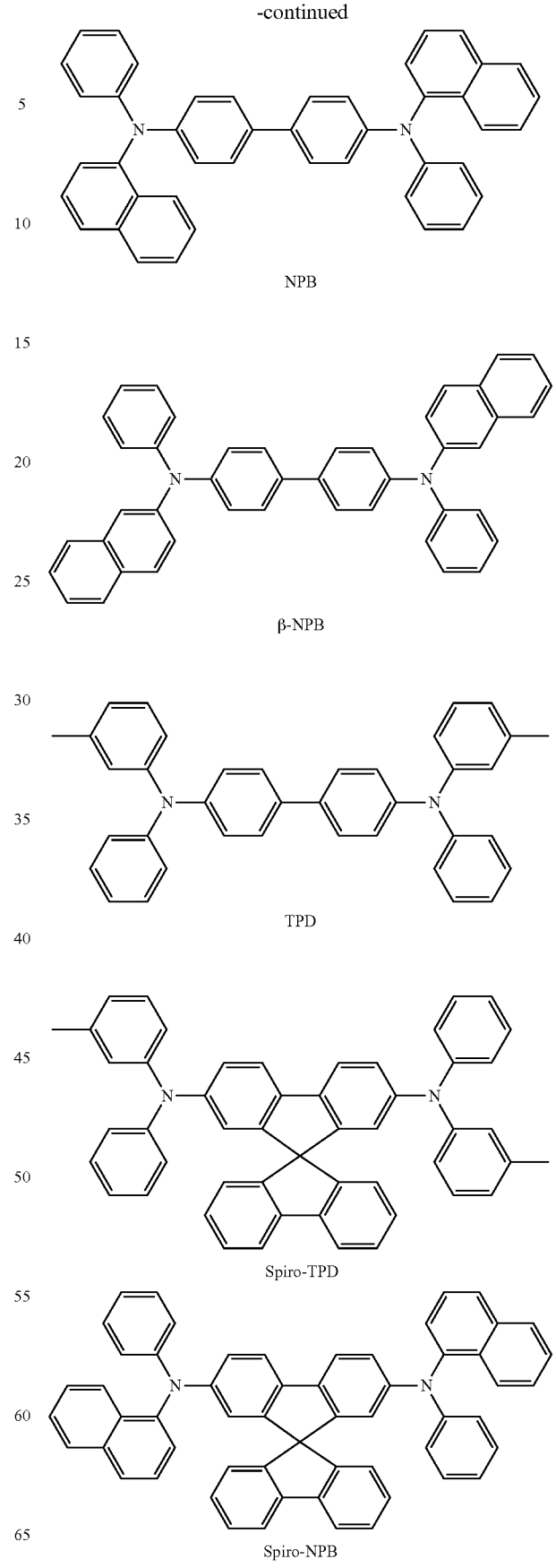
NPB
β-NPB
TPD
Spiro-TPD
Spiro-NPB -continued

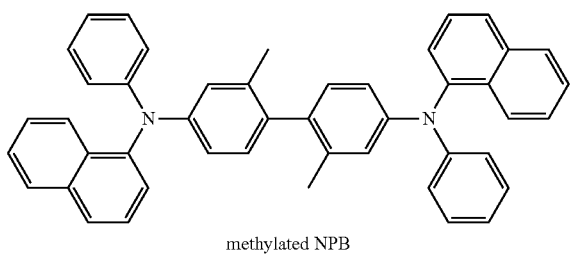

methylated NPB

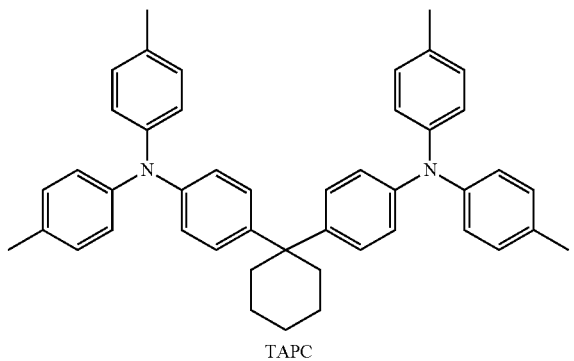

TAPC

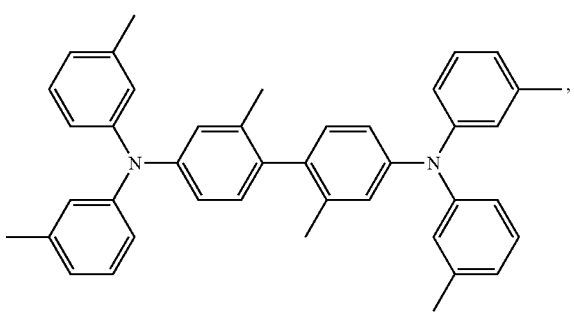

HMTPD

Formula 201

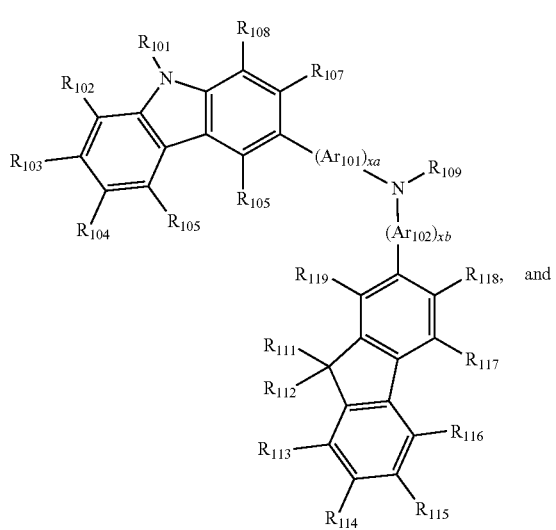

-continued

Formula 202

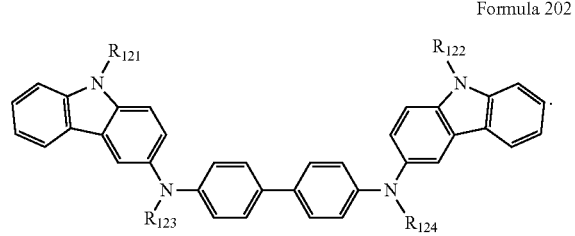

Ar$_{101}$ and Ar$_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group.

xa and xb in Formula 201 may each independently be an integer 0 to 5, or 0, 1, or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In one or more embodiments, the compound represented by Formula 201 may be represented by Formula 201A below, but is not limited thereto:

Formula 201A

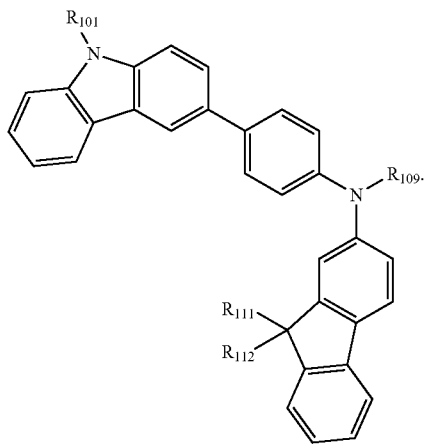

$R_{101}$, $R_{111}$, $R_{112}$, and $R_{109}$ in Formula 201A may be understood by referring to the description provided herein.

For example, the compound represented by Formula 201 and the compound represented by Formula 202 may include compounds HT1 to HT20 illustrated below, but embodiments of the present disclosure are not limited thereto.

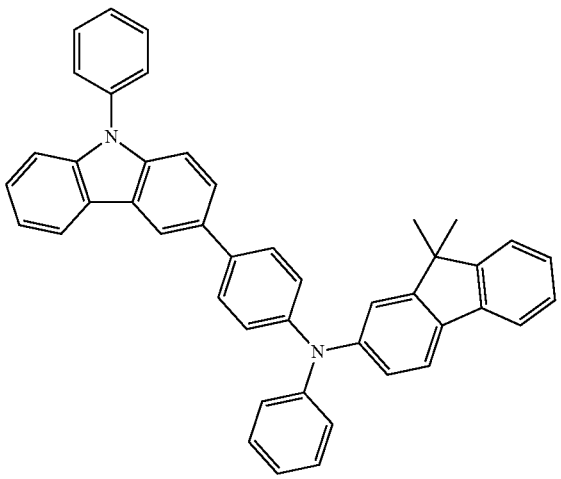

HT1

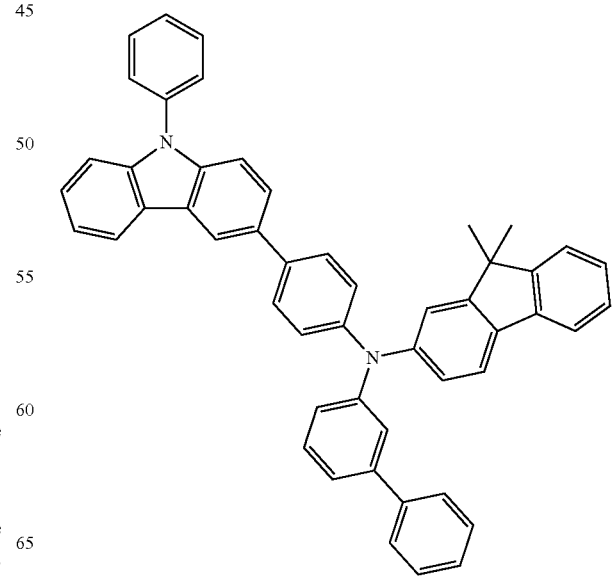

HT2

HT3
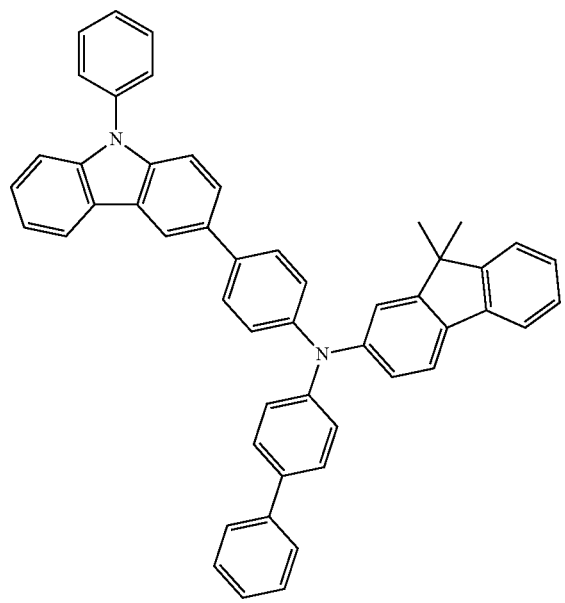
HT5
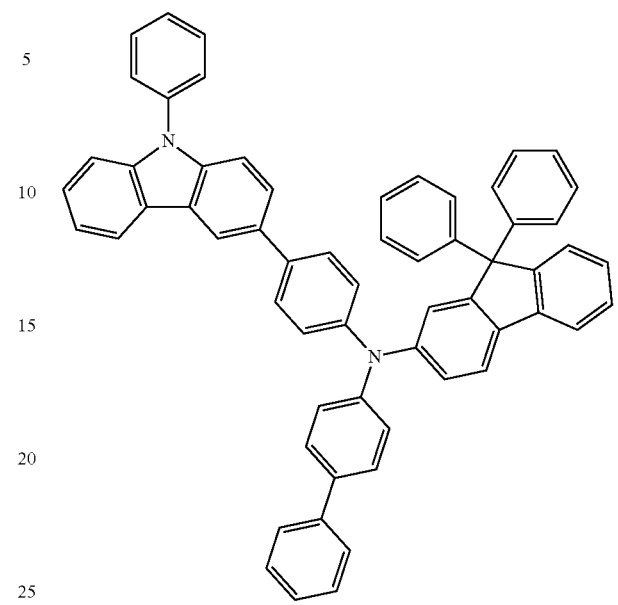
HT4
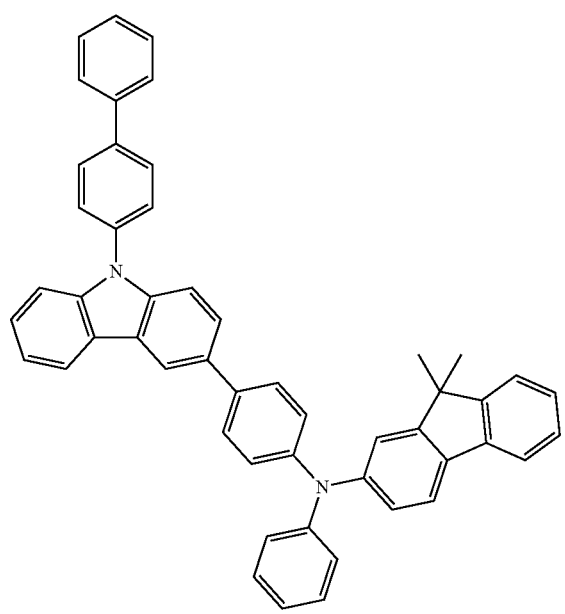
HT6
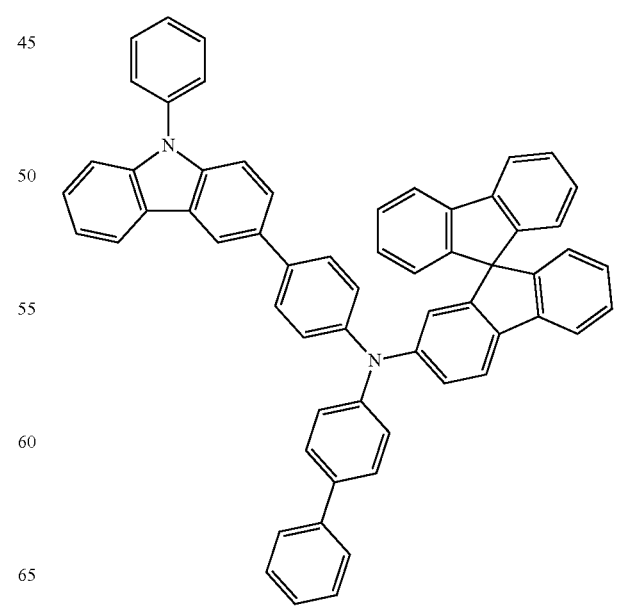

HT7
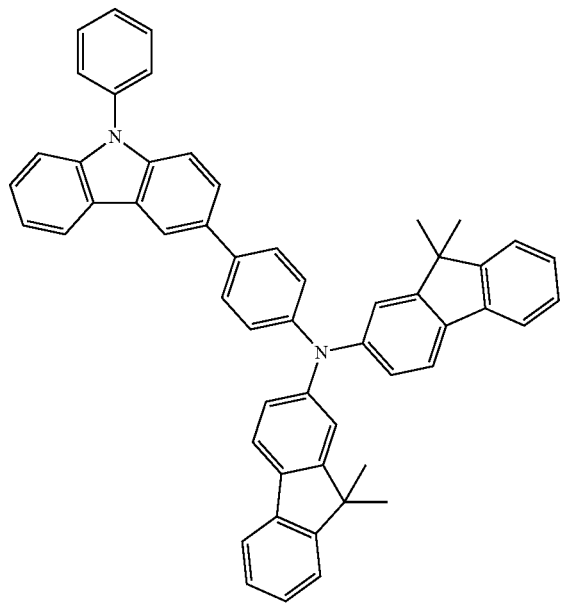
HT8
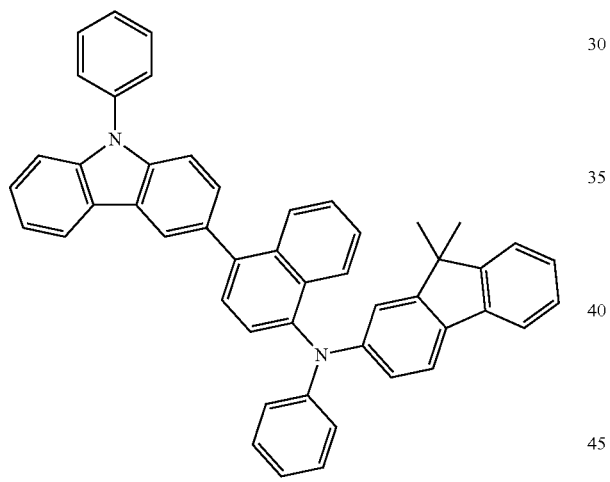
HT9
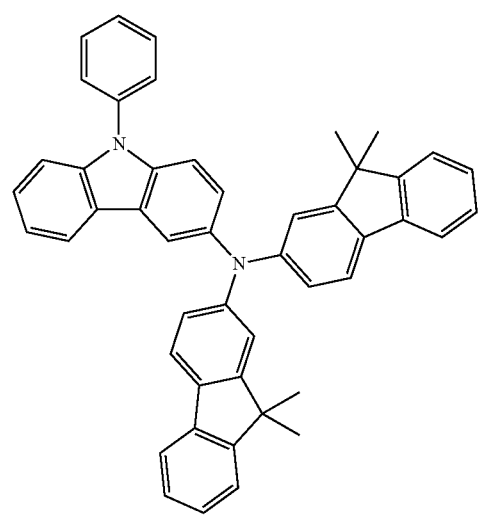
HT10
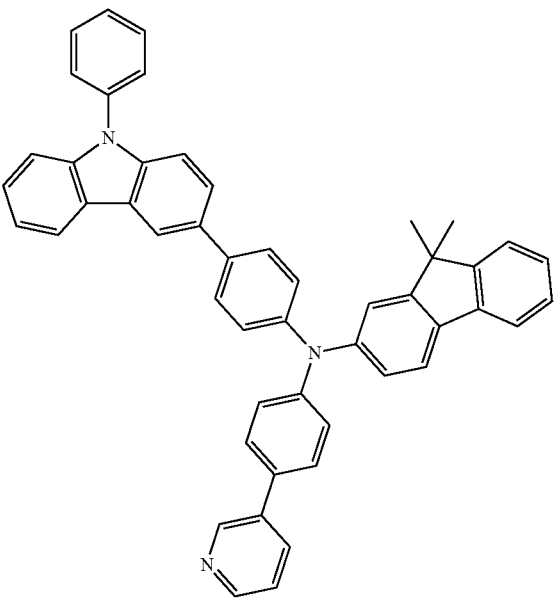
HT11
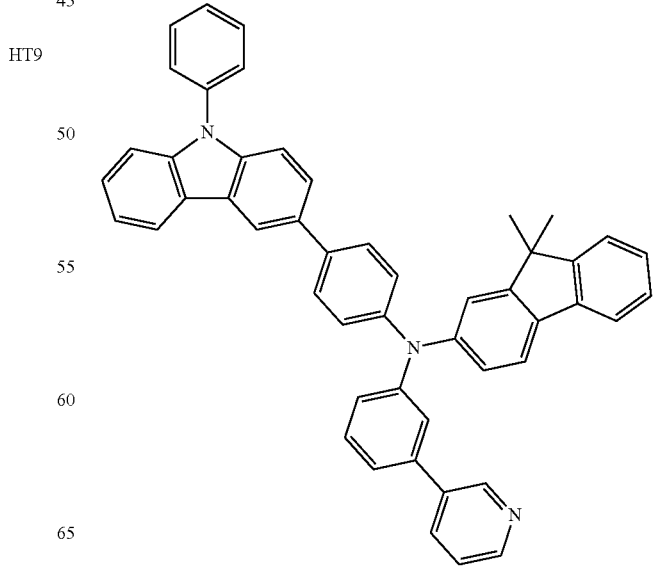

HT12
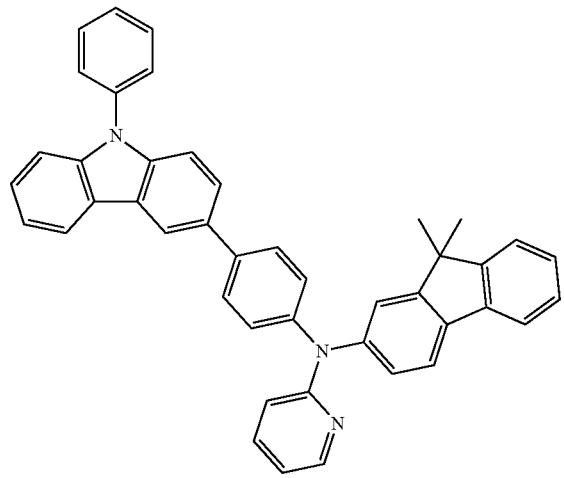
HT16
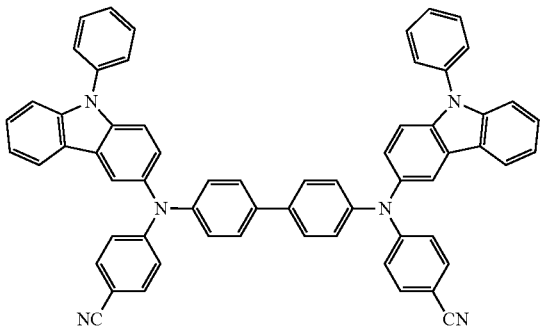
HT13
HT17
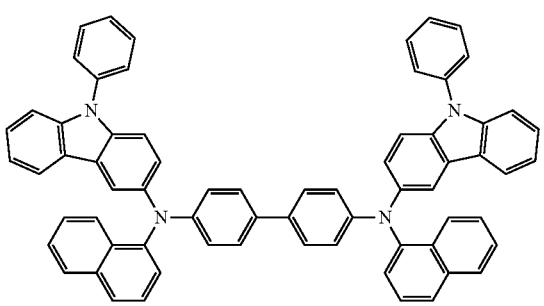
HT14
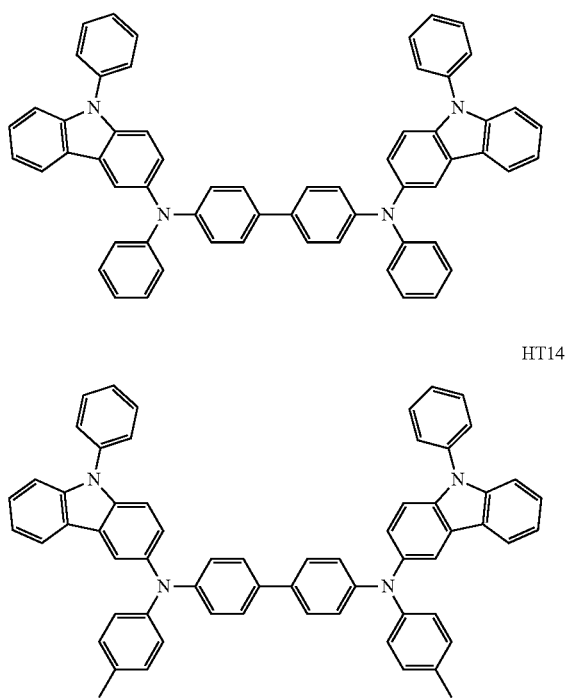
HT18
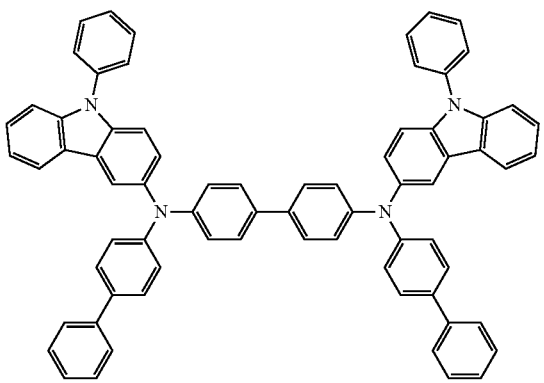
HT15
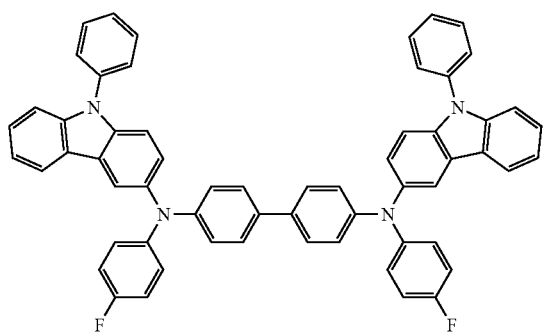
HT19
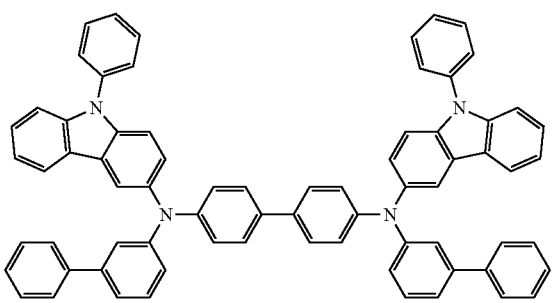

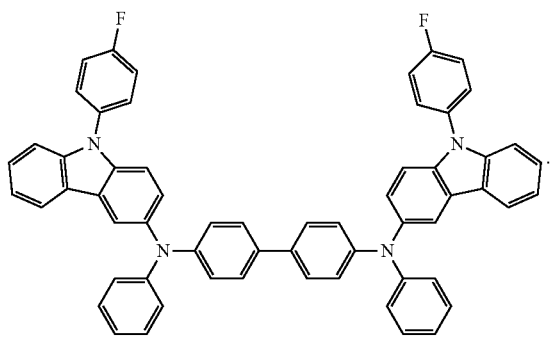

HT20

A thickness of the hole transport region may be in a range of about 100 Å to about 10,000 Å, for example, about 100 Å to about 5,000 Å, or for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 5,000 Å, or for example, about 100 Å to about 1,000 Å, and a thickness of the hole transport layer may be in a range of about 50 Å to about 2,000 Å, for example, about 100 Å to about 1,500 Å, or for example, about 300 Å to about 1,200 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for improving conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but embodiments of the present disclosure are not limited thereto:

Compound HT-D1

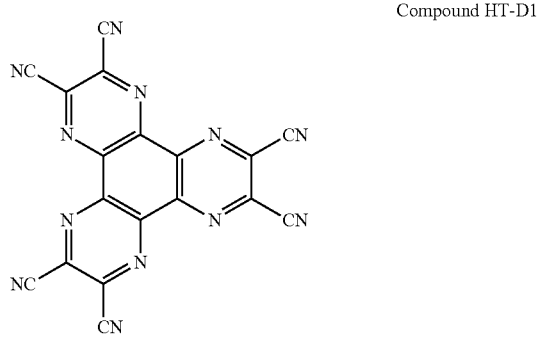

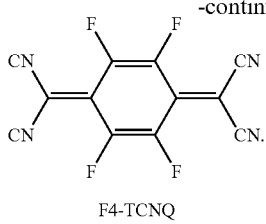

F4-TCNQ

The hole transport region may include a buffer layer.

Also, the buffer layer may compensate for an optical resonance distance depending on a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary depending on a material used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

When the organic light-emitting device is a full color organic light-emitting device, the emission layer may be patterned into a red emission layer, a green emission layer, and a blue emission layer. In one or more embodiments, due to a stack structure including a red emission layer, a green emission layer, and/or a blue emission layer, the emission layer may emit white light.

The emission layer may include a host and a dopant. The emission layer may include the condensed cyclic compound represented by Formula 1.

The host may be selected from:
i) compounds, each having at least one selected from a fluorene-based ring, a carbazole-based ring, a dibenzofuran-based ring, a dibenzothiophene-based ring, an indenocarbazole-based ring, an indolocarbazole-based ring, a benzofurocarbazole-based ring, a benzothienocarbazole-based ring, an acridine-based ring, a dihydroacridine-based ring, and a triindolobenzene-based ring, or
ii) a silicon-based compound and a phosphine oxide-based compound.

For example, the host may include a compound represented by one of Formulae 11-1 to 11-3, but embodiments of the present disclosure are not limited thereto:

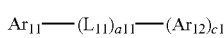

Formula 11-1

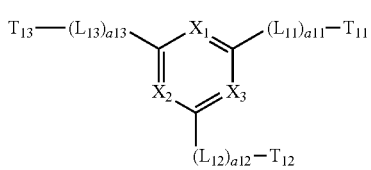

Formula 11-2

-continued $T_{21}$—$(L_{21})_{a21}$—$(T_{22})_{c1}$   Formula 11-3

Formula 13

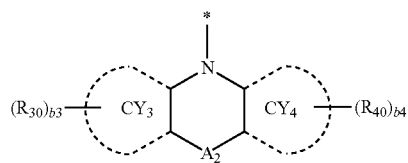

Formula 14

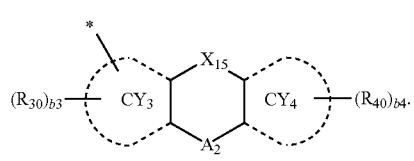

In Formulae 11-1 to 11-3, 13, and 14, $Ar_{11}$ and $Ar_{12}$ may each independently be a group represented by one of Formulae 13 and 14, $X_{15}$ may be $N(R_{22})$, O, or S, $X_1$ may be N or $C(T_{14})$, $X_2$ may be N or $C(T_{15})$, and $X_3$ may be N or $C(T_{16})$, wherein at least one from $X_1$ to $X_3$ is N, $T_{21}$ and $T_{22}$ may each independently be selected from *-$(L_{21})_{a21}$-$Si(Q_{41})(Q_{42})(Q_{43})$ and *-$(L_{21})_{a21}$-$P(=O)(Q_{51})(Q_{52})$, $L_{11}$ to $L_{13}$ and $L_{21}$ may each independently be selected from:

a single bond, O, S, $Si(Q_{61})(Q_{62})$, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{71})(Q_{72})(Q_{73})$, a11 to a13 and a21 may each independently be an integer of 0 to 5.

When a11 is two or more, two or more groups $L_{11}$ may be identical to or different from each other; when a12 is two or more, two or more groups $L_{12}$ may be identical to or different from each other; when a13 is two or more, two or more groups $L_{13}$ may be identical to or different from each other; when a21 is two or more, two or more groups $L_{21}$ may be identical to or different from each other, $CY_3$ and $CY_4$ may each independently be selected from a benzene group, a naphthalene group, a fluorene group, a carbazole group, a benzocarbazole group, an indolocarbazole group, a dibenzofuran group, and a dibenzothiophene group, $A_2$ may be selected from:

a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{81})(Q_{82})(Q_{83})$, wherein $T_{11}$ to $T_{16}$, $R_{22}$, $R_{30}$, and $R_{40}$ may each independently be selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ arylalkyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ heteroaryl alkyl group, a substituted or unsubstituted $C_1$-$C_{60}$ hetero aryloxy group, a substituted or unsubstituted $C_1$-$C_{60}$ hetero arylthio group, a substituted or unsubstituted monovalent non-aromatic condensed polycyclic group, a substituted or unsubstituted monovalent non-aromatic condensed heteropolycyclic group, and —$Si(Q_{91})(Q_{92})(Q_{93})$, b3 and b4 may each independently be an integer from 0 to 10, c1 may be 0, 1, 2, or 3,

* indicates a binding site to a neighboring atom, at least one substituent of the substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_7$-$C_{60}$ arylalkyl group, substituted $C_6$-$C_{60}$ aryloxy group, substituted $C_6$-$C_{60}$ arylthio group, substituted $C_1$-$C_{60}$ heteroaryl group, substituted $C_2$-$C_{60}$ heteroaryl alkyl group, substituted $C_1$-$C_{60}$ hetero aryloxy group, substituted $C_1$-$C_{60}$ hetero arylthio group, substituted monovalent non-aromatic condensed polycyclic group, and substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, and —Si($Q_{101}$)($Q_{102}$)($Q_{103}$), and $Q_{41}$ to $Q_{43}$, $Q_{51}$ to $Q_{52}$, $Q_{61}$ to $Q_{62}$, $Q_{71}$ to $Q_{73}$, $Q_{81}$ to $Q_{83}$, $Q_{91}$ to $Q_{93}$, and $Q_{101}$ to $Q_{103}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group.

$Ar_{11}$ and $Ar_{12}$ in Formula 11-1 may each independently be a group represented by one of Formulae 13-1 to 13-8 and 14-1 to 14-8:

Formula 13-1

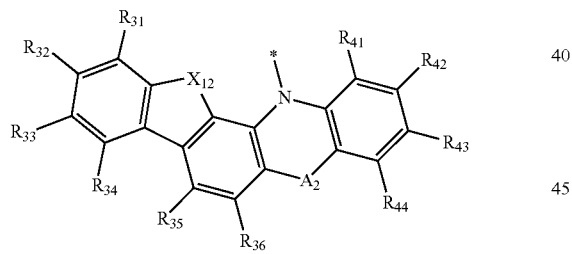

Formula 13-2

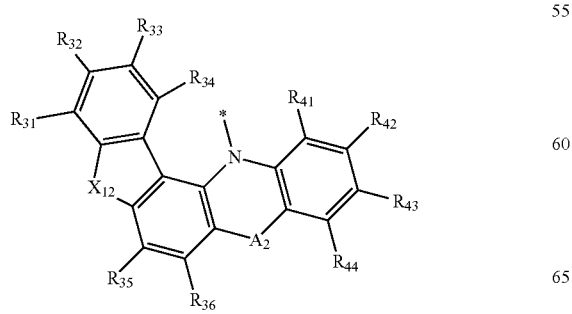

Formula 13-3

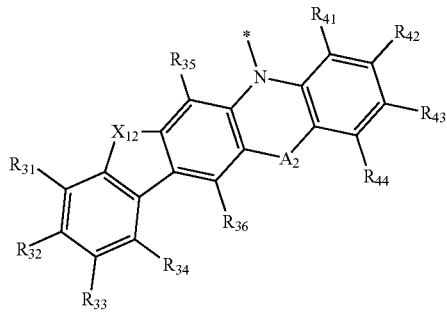

Formula 13-4

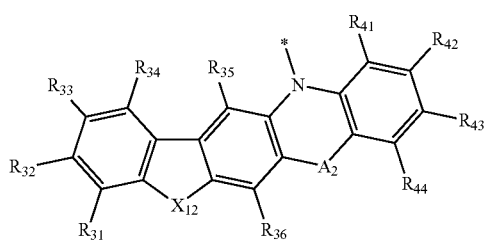

Formula 13-5

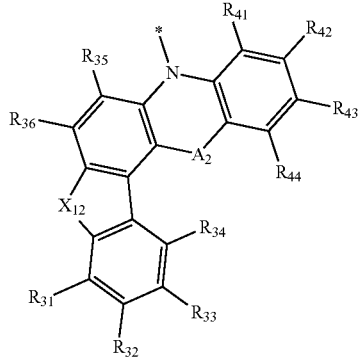

Formula 13-6

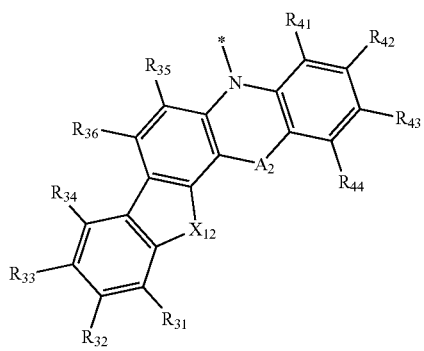

Formula 13-7

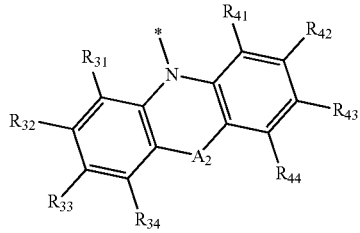

Formula 13-8
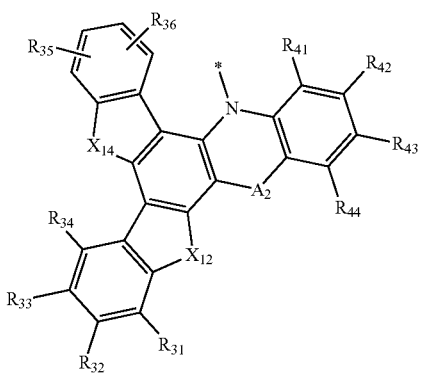

Formula 14-1
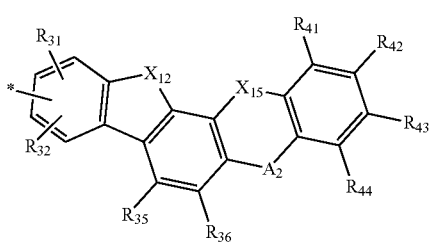

Formula 14-2
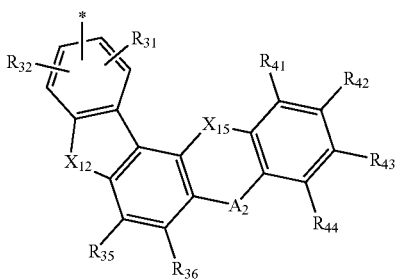

Formula 14-3
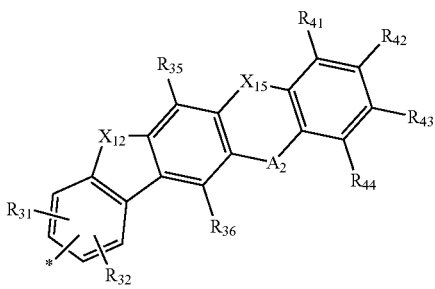

Formula 14-4
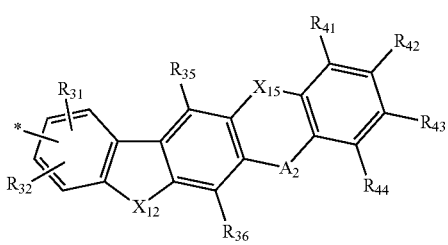

Formula 14-5
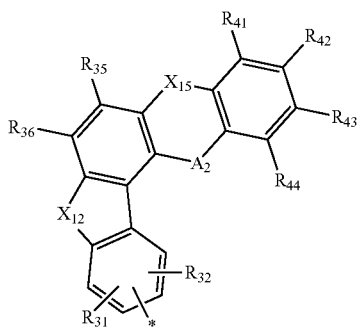

Formula 14-6
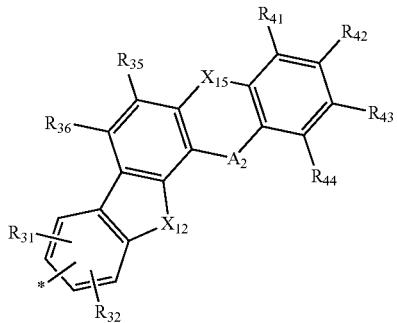

Formula 14-7
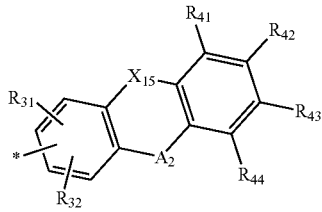

Formula 14-8
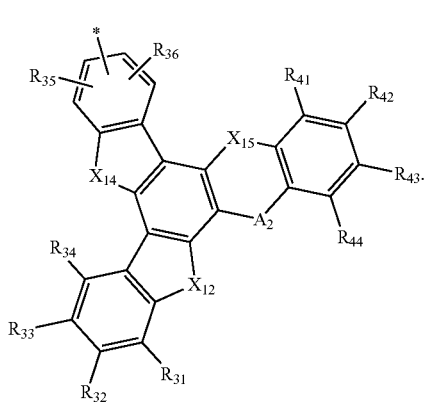

In Formulae 13-1 to 13-8 and 14-1 to 14-8, $X_{12}$ and $X_{14}$ may each independently be $C(R_{37})(R_{38})$, $N(R_{39})$, O, or S, $X_{15}$ and $A_2$ are the same as described above, $R_{31}$ to $R_{39}$ are each independently the same as described in connection with $R_{30}$, $R_{41}$ to $R_{44}$ are each independently the same as described in connection with $R_{40}$, and

* indicates a binding site to a neighboring atom.

In one or more embodiments, $A_2$ in Formulae 13, 14, 13-1 to 13-8, and 14-1 to 14-8 may be selected from:

a single bond, a $C_1$-$C_2$ alkylene group, and a $C_2$ alkenylene group; and a $C_1$-$C_2$ alkylene group and a $C_2$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{81}$)($Q_{82}$)($Q_{83}$), $R_{22}$, $R_{30}$ to $R_{39}$ and $R_{40}$ to $R_{44}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a carbazolyl group, a dibenzofuranyl group, and a dibenzothiophenyl group;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; —Si($Q_{91}$)($Q_{92}$)($Q_{93}$), and $Q_{81}$ to $Q_{83}$ and $Q_{91}$ to $Q_{93}$ may each independently be selected from hydrogen, a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one or more embodiments, $Ar_{11}$ and $Ar_{12}$ in Formula 11-1 may each independently be a group represented by one of Formulae 17-1 to 17-19 and 18-1 to 18-8, but embodiments of the present disclosure are not limited thereto:

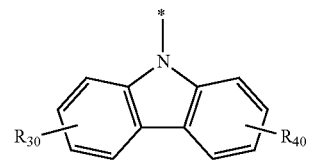
17-1

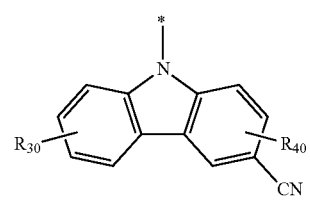
17-2

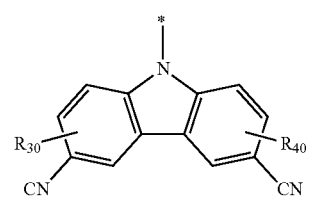
17-3

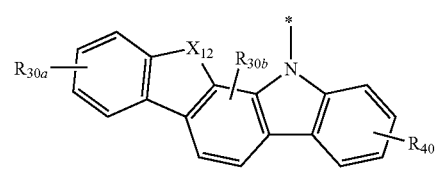
17-4

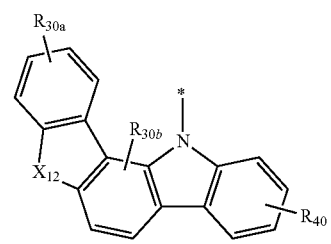
17-5

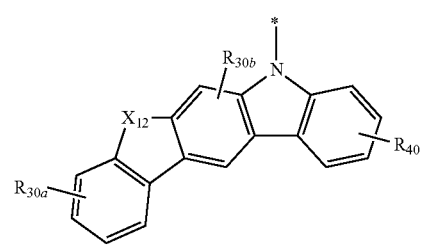
17-6

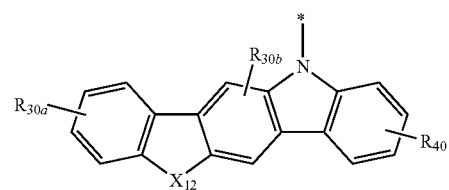
17-7

-continued
17-8
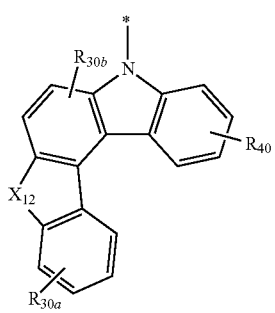
17-9
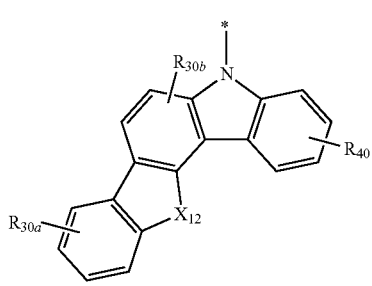
17-10
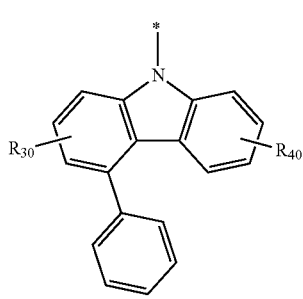
17-11
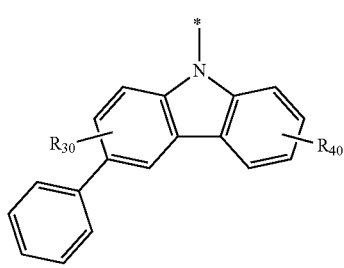
17-12
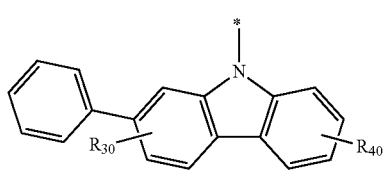
17-13
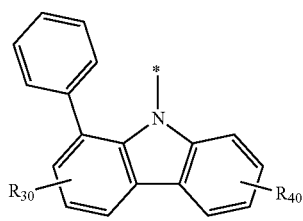
-continued
17-14
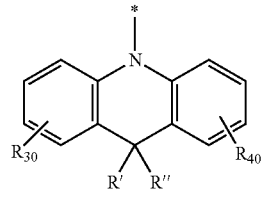
17-15
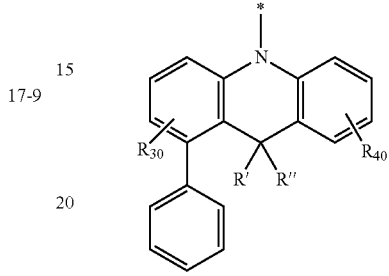
17-16
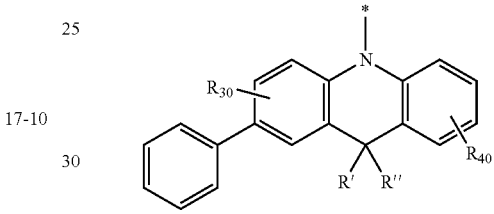
17-17
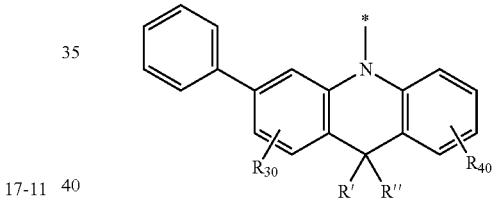
17-18
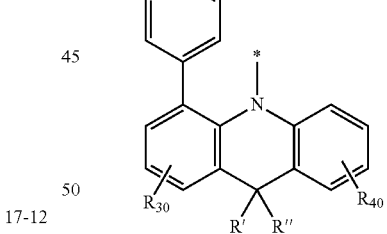
17-19
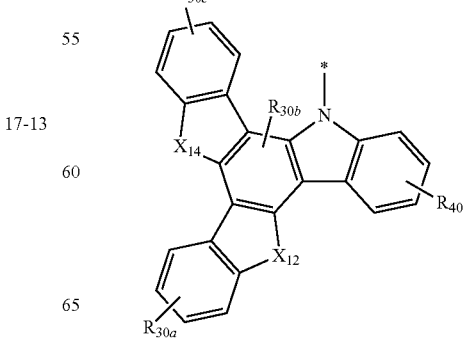

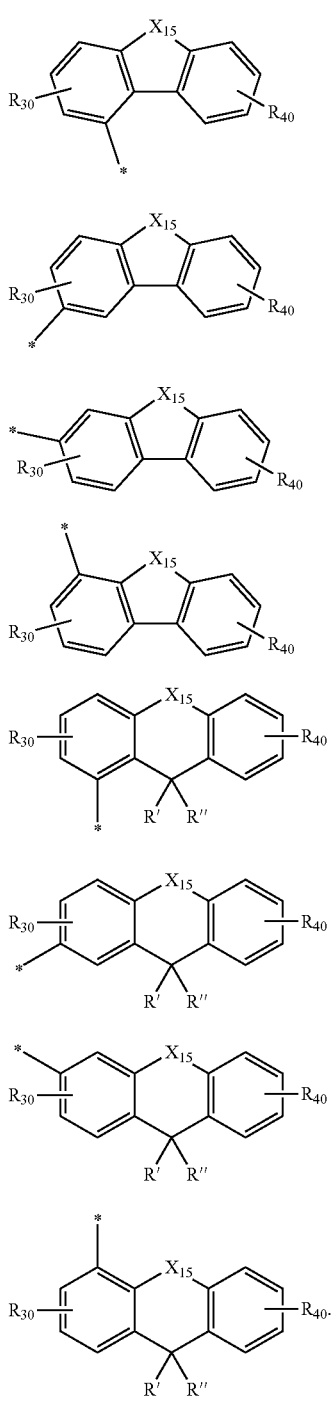

In Formulae 17-1 to 17-19 and 18-1 to 18-8, $X_{12}$ and $X_{14}$ may each independently be $C(R_{37})(R_{39})$, $N(R_{39})$, O, or S, $X_{15}$ may be $N(R_{17})$, O, or S, R' and R" may each independently be selected from hydrogen, deuterium, a $C_1$-$C_{10}$ alkyl group, a $C_1$-$C_{10}$ alkoxy group, a phenyl group, a biphenyl group, a terphenyl group, a naphthyl group, a fluorenyl group, a carbazolyl group, a dibenzofuranyl group, and a dibenzothiophenyl group, $R_{22}$, $R_{30}$, and $R_{40}$ are the same as described above, $R_{30a}$ to $R_{30c}$ may be the same as described in connection with $R_{30}$, and

* indicates a binding site to a neighboring atom.

For example, in Formulae 17-1 to 17-19 and 18-1 to 18-8, $R_{22}$, $R_{30}$, $R_{30a}$ to $R_{30c}$, and $R_{40}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$ and —$CFH_2$, a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

—$Si(Q_{91})(Q_{92})(Q_{93})$; and $Q_{91}$ to $Q_{93}$ may each independently be selected from hydrogen, a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

Two or three from $X_1$ to $X_3$ in Formula 11-2 may be N.

For example, $T_{11}$ to $T_{16}$ in Formula 11-2 may each independently be selected from:

hydrogen, deuterium, —F, a cyano group, a $C_1$-$C_{10}$ alkyl group, a $C_1$-$C_{10}$ alkoxy group —$CF_3$, —$CF_2H$, and —$CFH_2$;

a $C_1$-$C_{10}$ alkyl group and a $C_1$-$C_{10}$ alkoxy group, each substituted with at least one selected from deuterium, —F, a cyano group —$CF_3$, —$CF_2H$, and —$CFH_2$;

a phenyl group, a biphenyl group, a terphenyl group, a pyridinyl group, a pyrimidinyl group, a triazinyl group, a carbazolyl group, a dibenzofuranyl group, and a dibenzothiophenyl group;

a phenyl group, a biphenyl group, a terphenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a $C_1$-$C_{10}$ alkyl group, a $C_1$-$C_{10}$ alkoxy group, —$CF_3$, —$CF_2H$, —$CFH_2$, a phenyl group, a biphenyl group, a terphenyl group, a pyridinyl group, a pyrimidinyl group, a triazinyl group, a carbazolyl group, a dibenzofuranyl group, and a dibenzothiophenyl group;

—Si(Q$_{91}$)(Q$_{92}$) (Q$_{93}$); and

Q$_{91}$ to Q$_{93}$ may each independently be selected from hydrogen, a C$_1$-C$_{10}$ alkyl group, a C$_1$-C$_{10}$ alkoxy group, a phenyl group, a biphenyl group, a terphenyl group, a pyridinyl group, a pyrimidinyl group, a triazinyl group, a carbazolyl group, a dibenzofuranyl group, and a dibenzothiophenyl group, but embodiments of the present disclosure are not limited thereto.

T$_{21}$ and T$_{22}$ in Formula 11-3 may each independently be selected from *-(L$_{21}$)$_{a21}$-Si(Q$_{41}$)(Q$_{42}$)(Q$_{43}$) and *-(L$_{21}$)$_{a21}$-P(=O)(Q$_{51}$)(Q$_{52}$), and Q$_{41}$ to Q$_{43}$ and Q$_{51}$ to Q$_{52}$ may each independently be selected from:

a phenyl group, a biphenyl group, a terphenyl group, a pyridinyl group, a pyrimidinyl group, a triazinyl group, a carbazolyl group, a dibenzofuranyl group, and a dibenzothiophenyl group; and a phenyl group, a biphenyl group, a terphenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a C$_1$-C$_{10}$ alkyl group, a C$_1$-C$_{10}$ alkoxy group, —CF$_3$, —CF$_2$H, —CFH$_2$, a phenyl group, a biphenyl group, a terphenyl group, a pyridinyl group, a pyrimidinyl group, a triazinyl group, a carbazolyl group, a dibenzofuranyl group, and a dibenzothiophenyl group;

but embodiments of the present disclosure are not limited thereto.

For example, the host may be selected from Compounds H-1 to H-26:

H-1

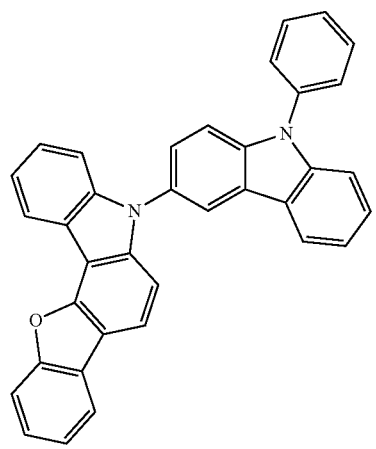

H-2

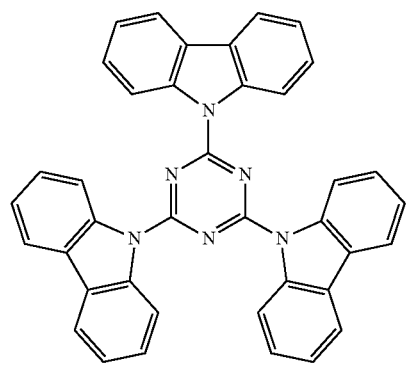

H-3

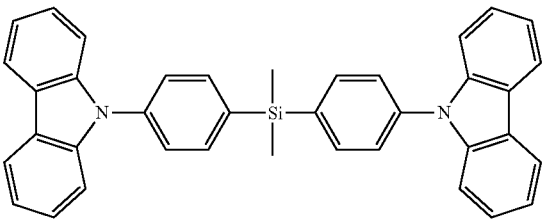

H-4

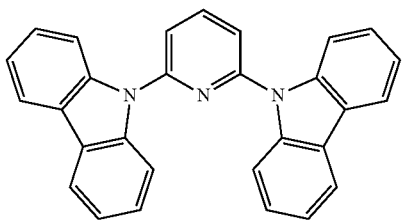

H-5

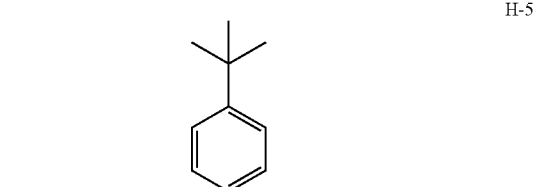

H-6

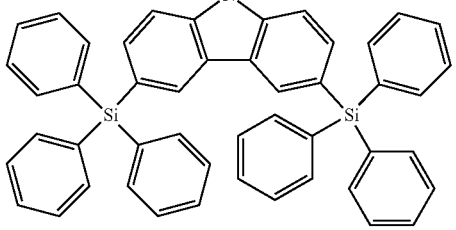

H-7

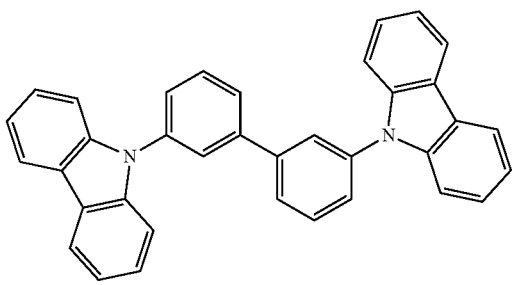

H-8
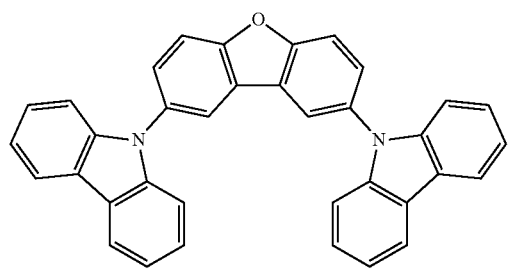
H-9
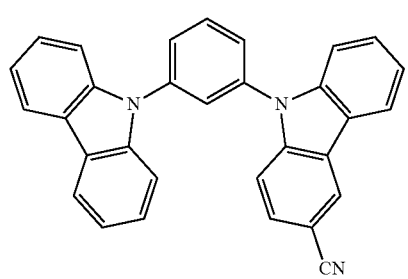
H-10
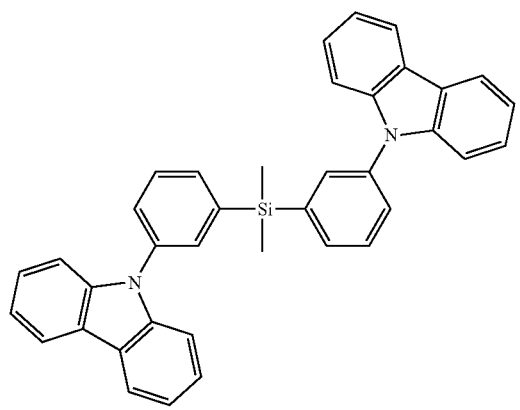
H-11
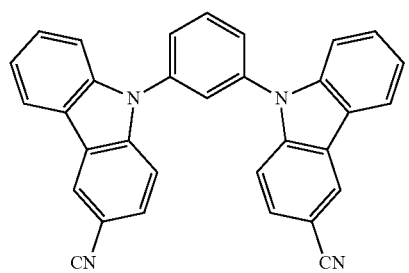
H-12
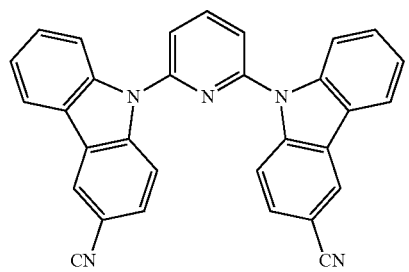
H-13
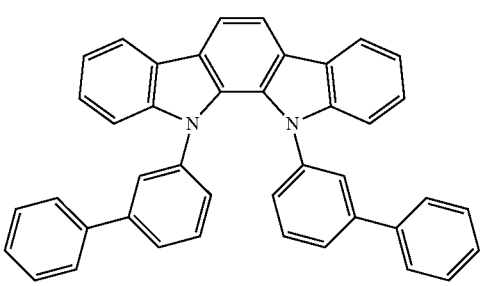
H-14
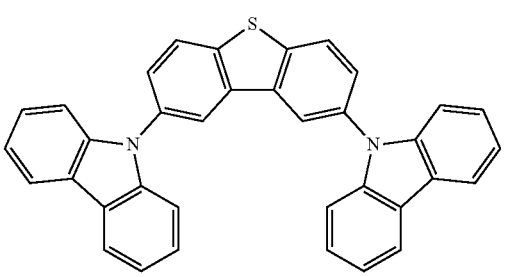
H-15
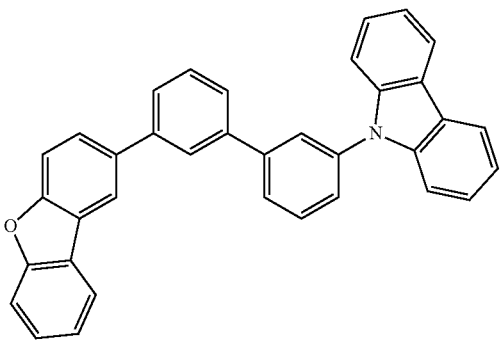
H-16
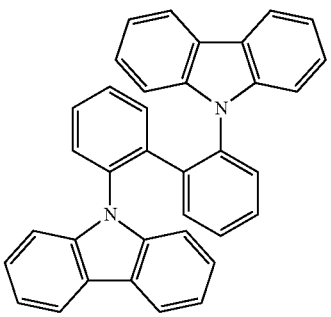
H-17
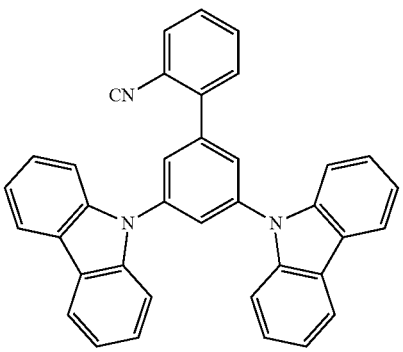

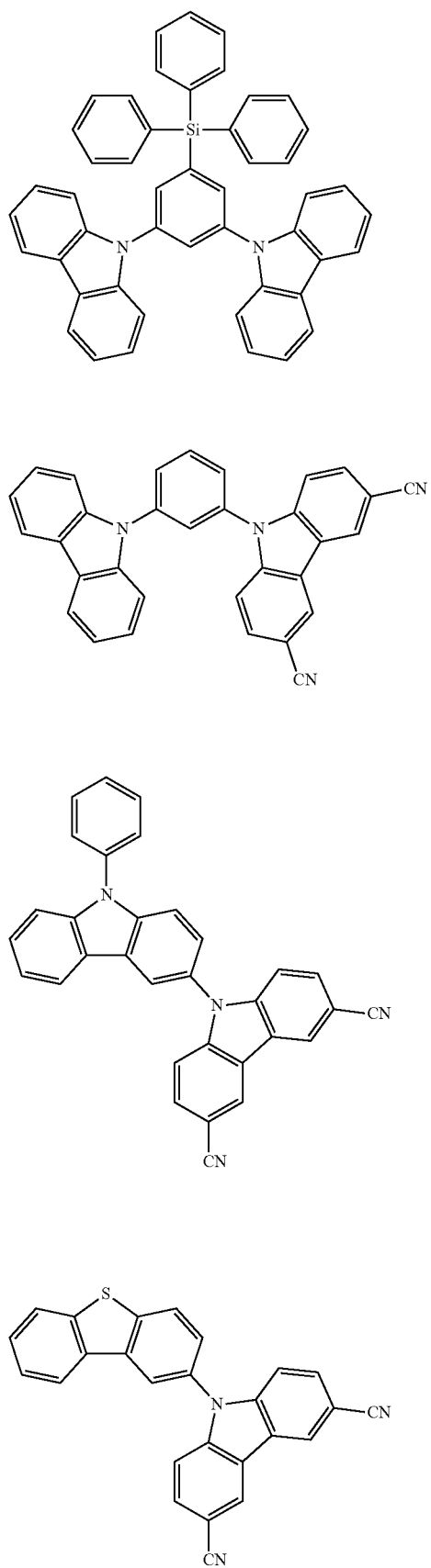
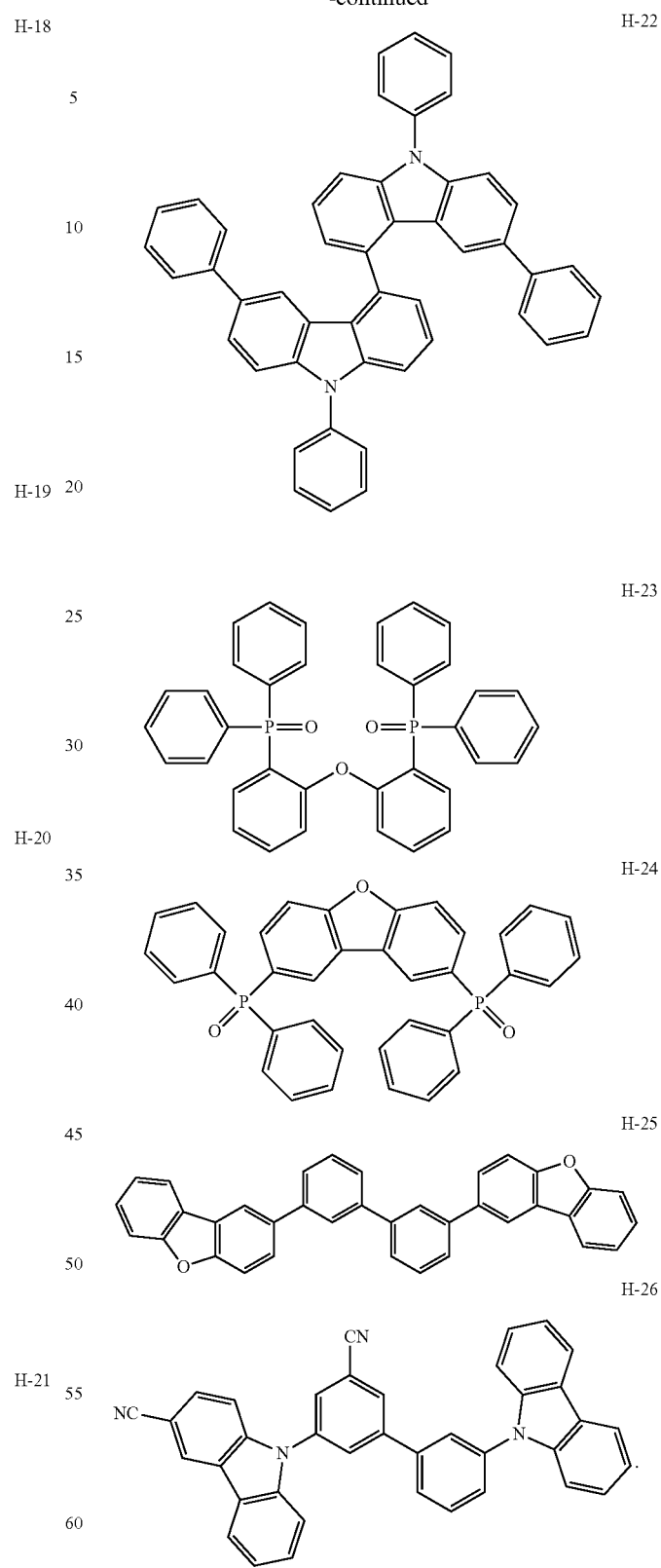
In one or more embodiments, the host may include at least one selected from TPBi, TBADN, ADN (also referred to as "DNA"), CBP, CDBP, TCP, mCP, Compound H50, and Compound H51:

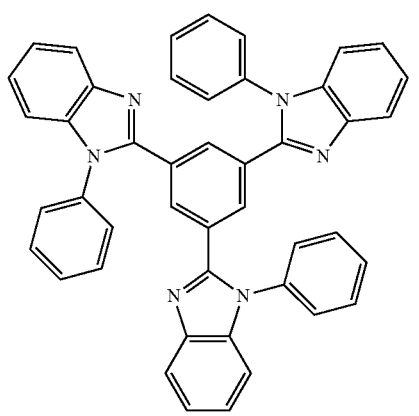
TPBi
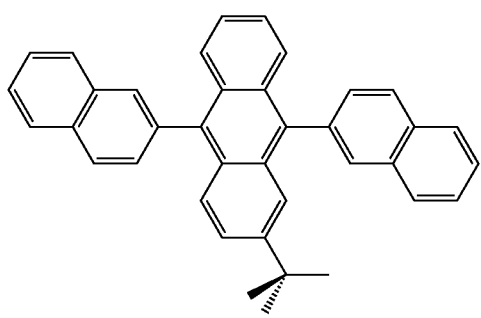
TBADN
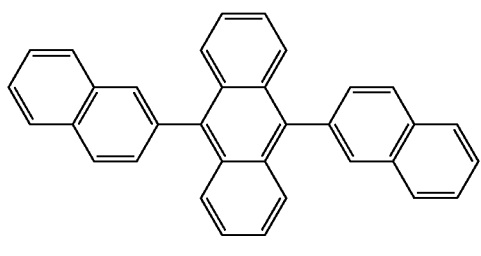
ADN
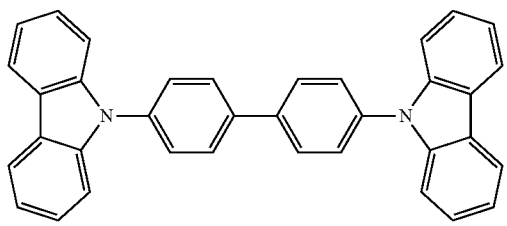
CBP
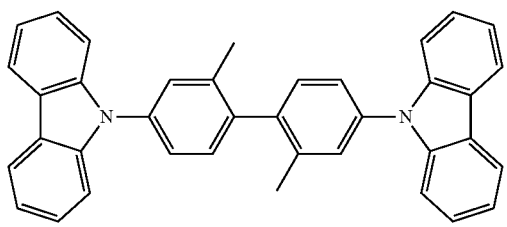
CDBP
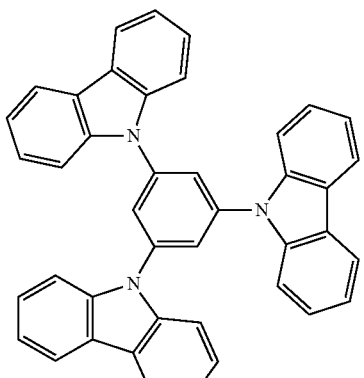
TCP
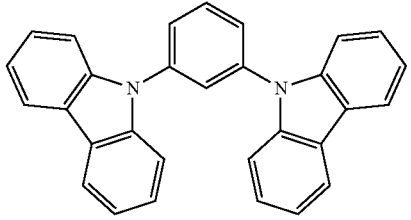
mCP
Compound H50
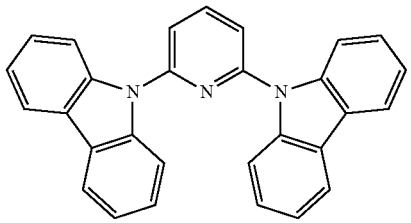
Compound H51
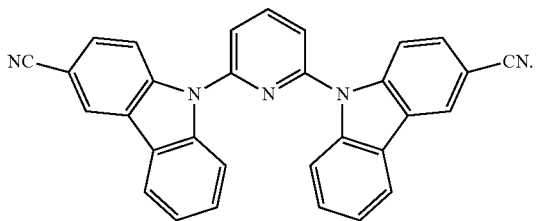
In one or more embodiments, the host may further include a compound represented by Formula 301 below:
Formula 301
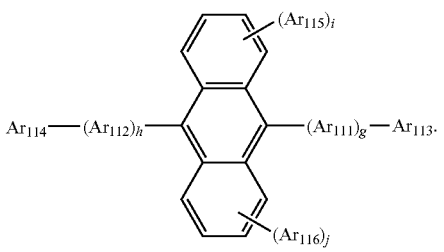

$Ar_{111}$ and $Ar_{112}$ in Formula 301 may each independently be selected from:
- a phenylene group, a naphthylene group, a phenanthrenylene group, and a pyrenylene group; and
- a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may each independently be selected from:
- a $C_1$-$C_{10}$ alkyl group, a phenyl group, a naphthyl group, a phenanthrenyl group, and a pyrenyl group; and
- a phenyl group, a naphthyl group, a phenanthrenyl group, and a pyrenyl group, each substituted with at least one selected from a phenyl group, a naphthyl group, and an anthracenyl group.

g, h, i, and j in Formula 301 may each independently be an integer from 0 to 4, and may be, for example, 0, 1, or 2.

$Ar_{113}$ and $Ar_{116}$ in Formula 301 may each independently be selected from:
- a $C_1$-$C_{10}$ alkyl group substituted with at least one selected from a phenyl group, a naphthyl group, and an anthracenyl group;
- a phenyl group, a naphthyl group, an anthracenyl group, a pyrenyl, a phenanthrenyl group, and a fluorenyl group;
- a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

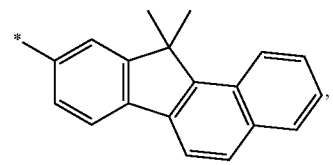 [SMILES: *c1ccc2c(c1)C(C)(C)c1c-2ccc2ccccc12]

but embodiments of the present disclosure are not limited thereto.

In one or more embodiments, the host may include a compound represented by Formula 302 below:

Formula 302

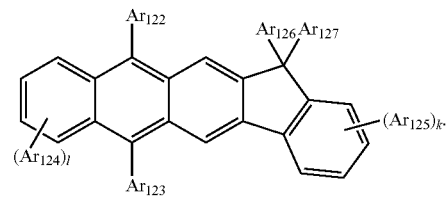

$Ar_{122}$ to $Ar_{125}$ in Formula 302 are the same as described in detail in connection with $Ar_{113}$ in Formula 301.

$Ar_{126}$ and $Ar_{127}$ in Formula 302 may each independently be a $C_1$-$C_{10}$ alkyl group (for example, a methyl group, an ethyl group, or a propyl group).

k and l in Formula 302 may each independently be an integer from 0 to 4. For example, k and l may be 0, 1, or 2.

The compound represented by Formula 301 and the compound represented by Formula 302 may include Compounds H1 to H42 illustrated below, but embodiments of the present disclosure are not limited thereto.

H1

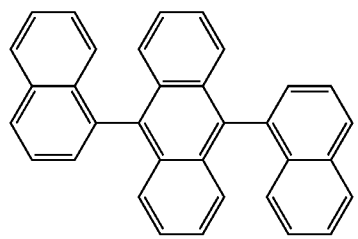

H2

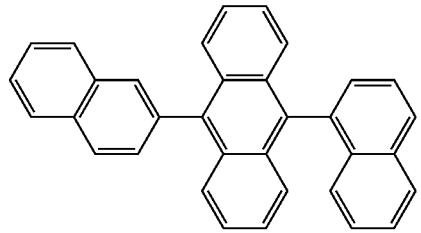

H3

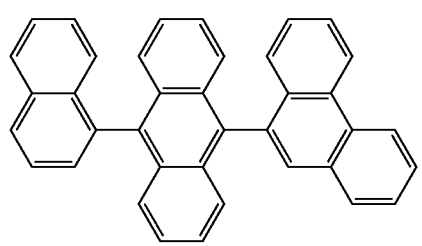

H4

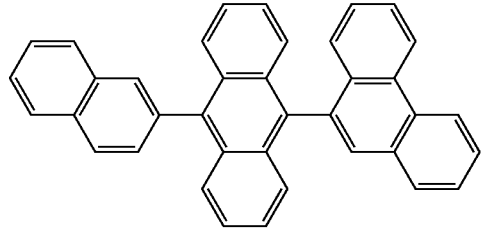

-continued
H5
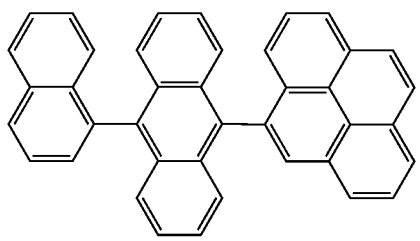
H6
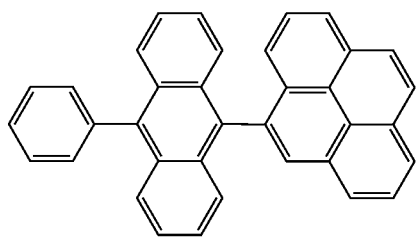
H7
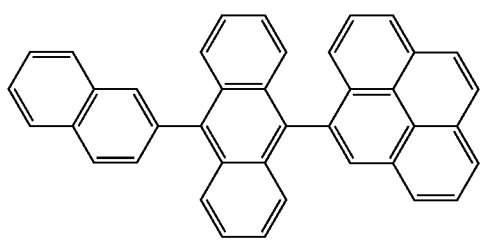
H8
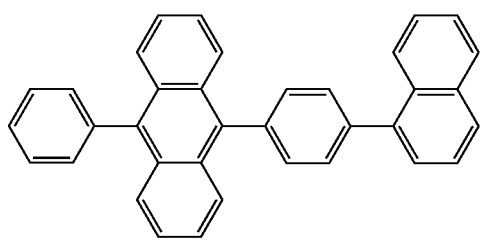
H9
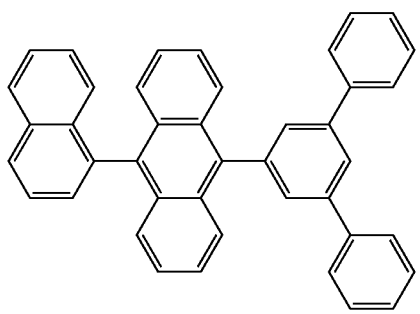
H10
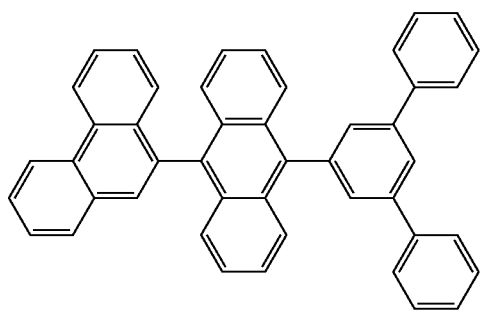
H11
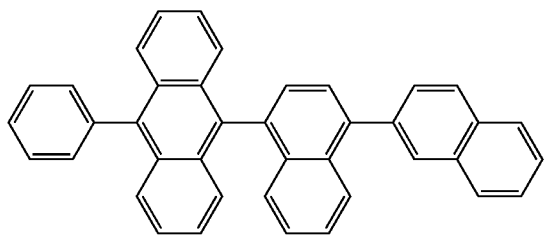
H12
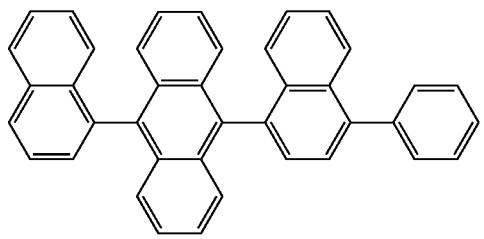
H13
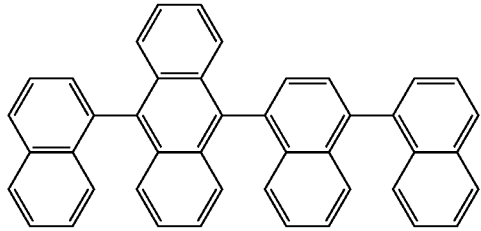
H14
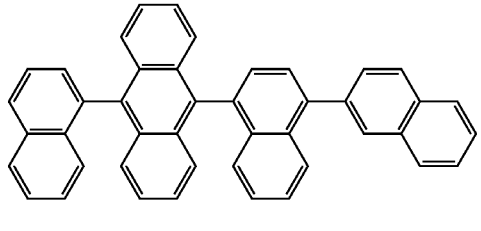
H15
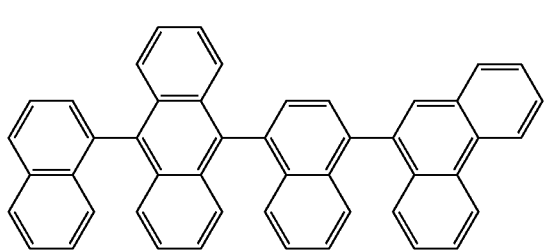

-continued
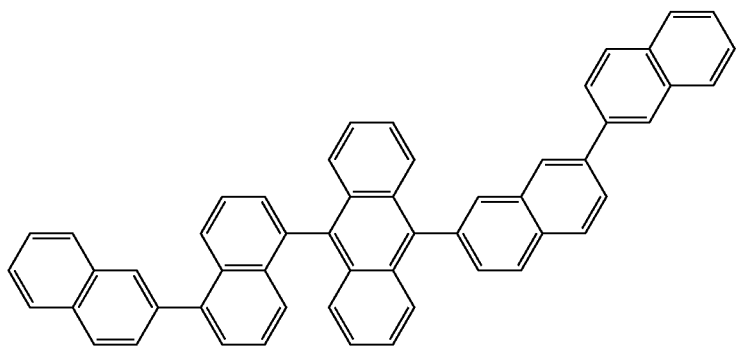
H16
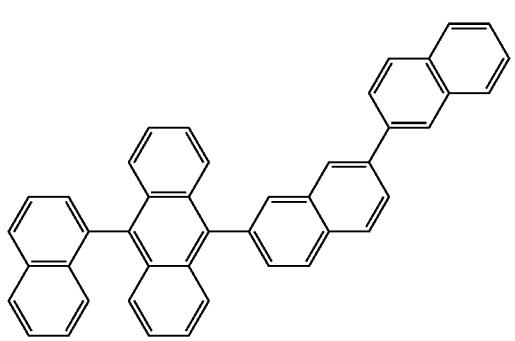
H17
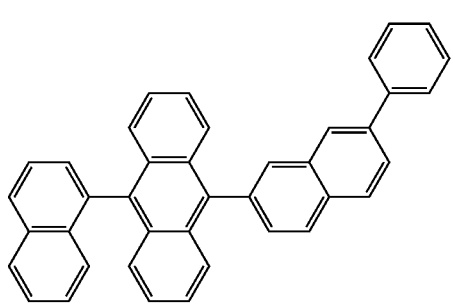
H18
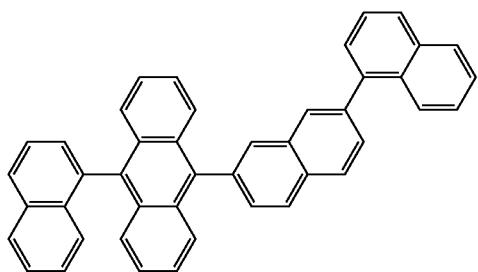
H19
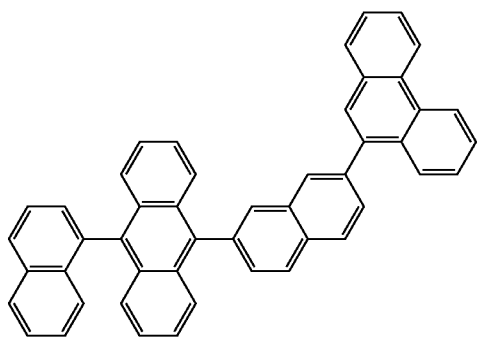
H20
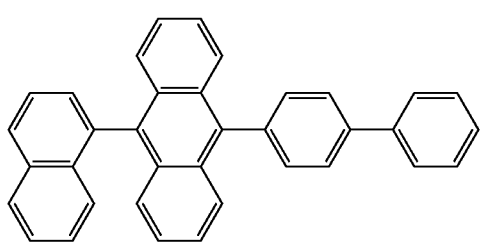
H21
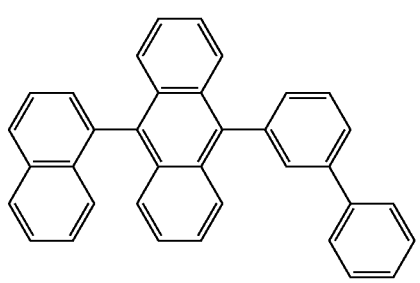
H22
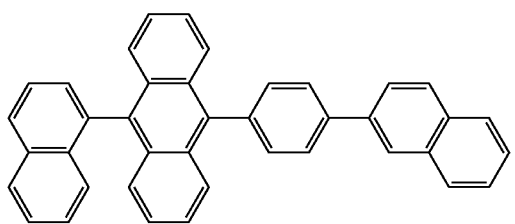
H23
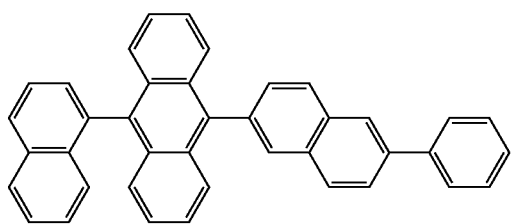
H24

-continued
H25
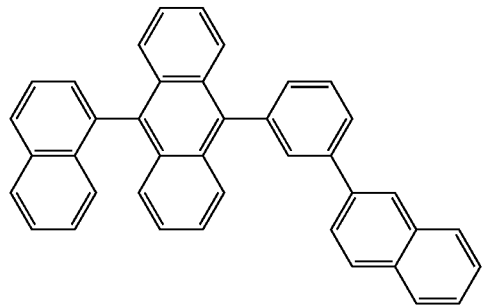
H26
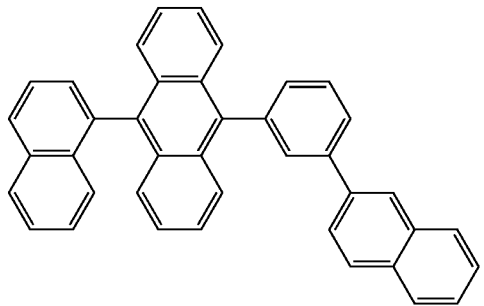
H27
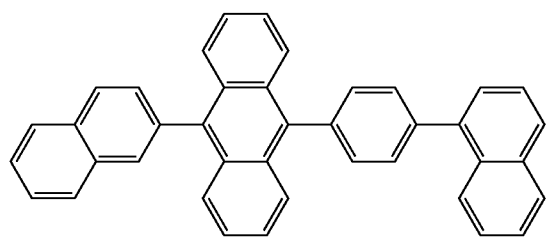
H28
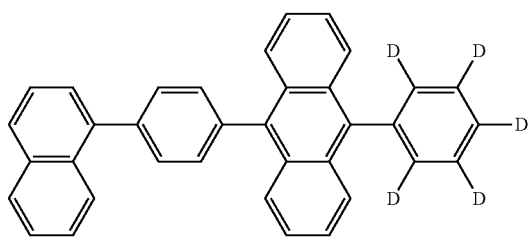
H29
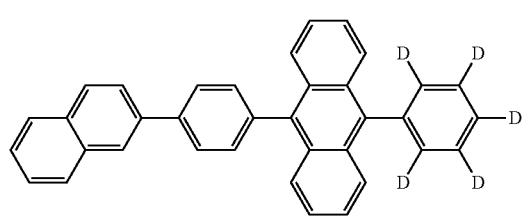
H30
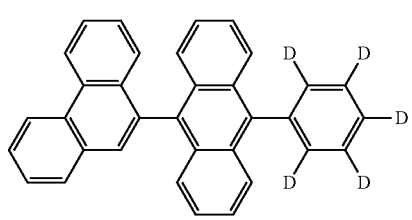
H31
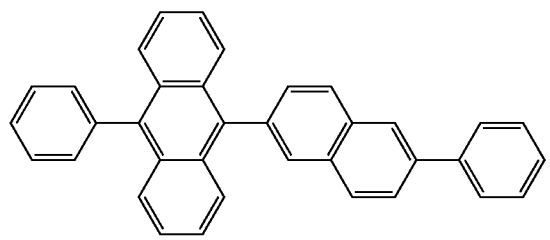
H32
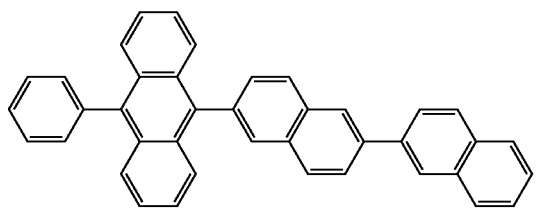
H33
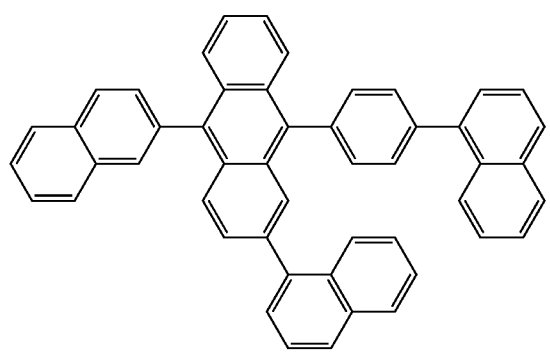
H34
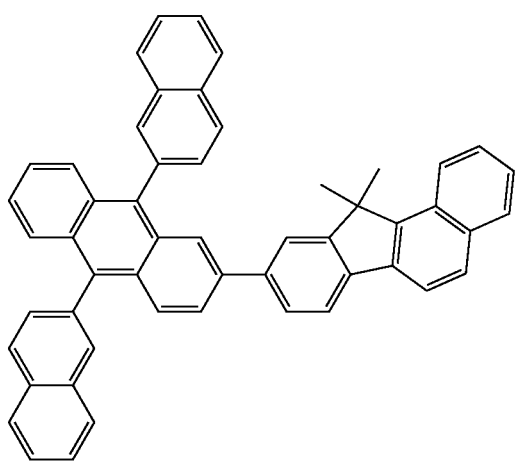

-continued
H35
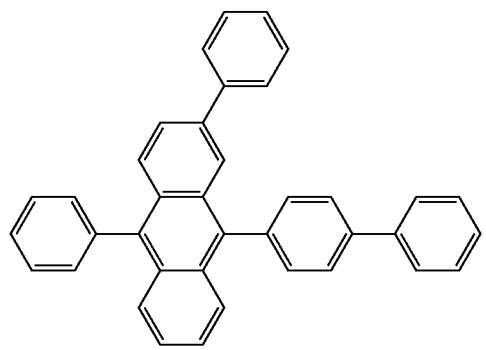
H36
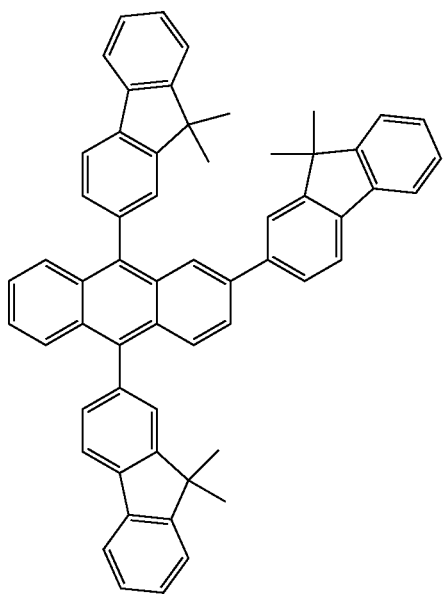
H37
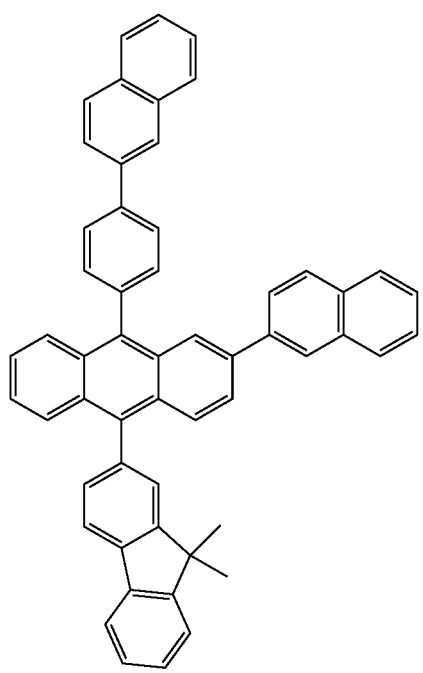
H38
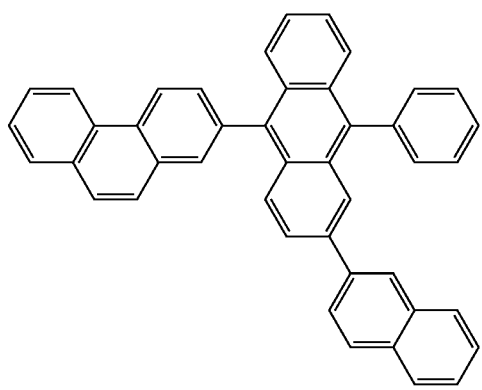

-continued

H39
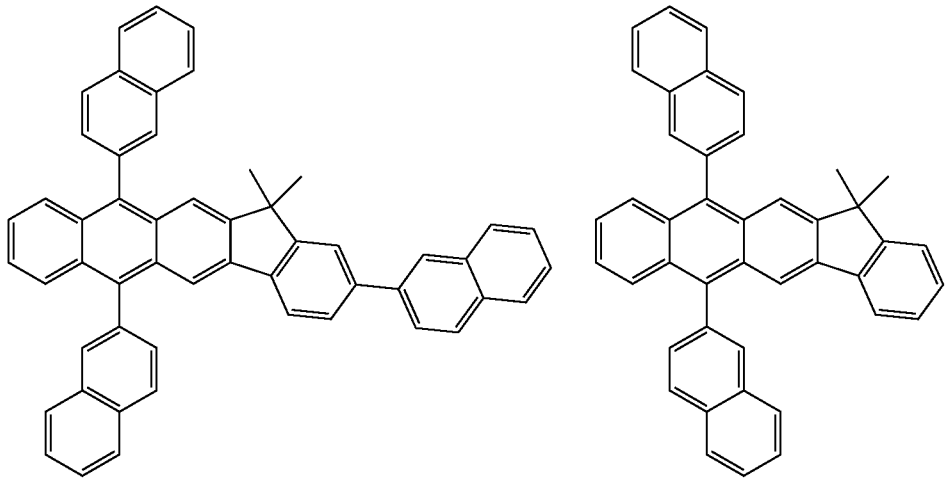

H40

H41
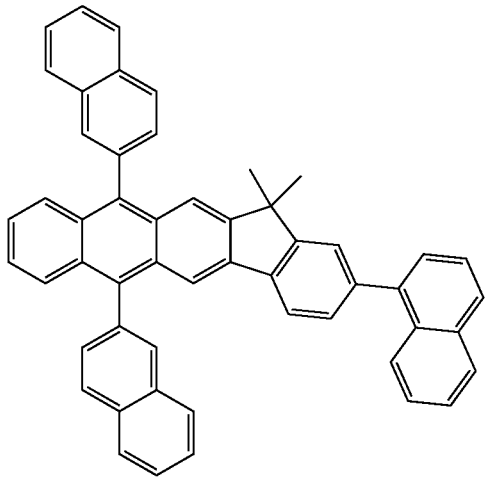

H42
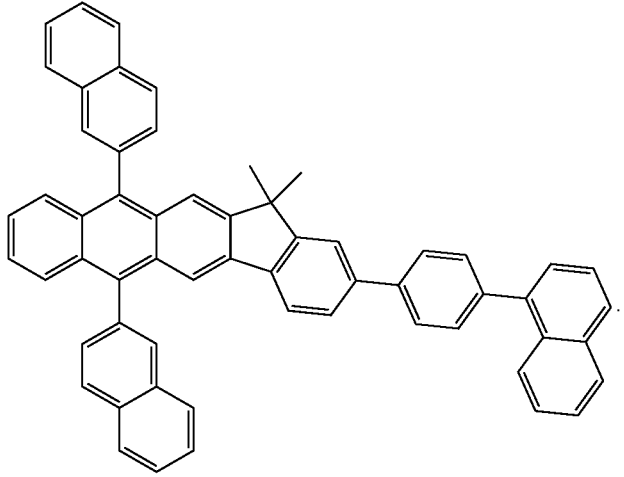

A dopant in the emission layer may be a fluorescent dopant that emits light according to a fluorescent emission mechanism or a phosphorescent dopant that emits light according to a phosphorescent emission mechanism.

The fluorescent dopant may be selected from a condensed polycyclic compound and a styryl-based compound.

For example, the fluorescent dopant may include one selected from a naphthalene-based core, a fluorene-based core, a spiro-bifluorene-based core, a benzofluorene-based core, a dibenzofluorene-based core, a phenanthrene-based core, an anthracene-based core, a fluoranthene-based core, a triphenylene-based core, a pyrene-based core, a chrysene-based core, a naphthacene-based core, a picene-based core, a perylene-based core, a pentaphene-based core, an indenoanthracene-based core, a tetracene-based core, a bis anthracene-based core, and a core represented by one of Formulae 501-1 to 501-18, but embodiments of the present disclosure are not limited thereto:
501-1
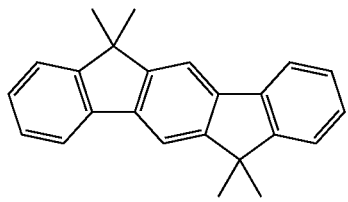
501-2
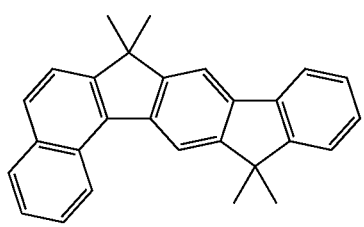
501-3
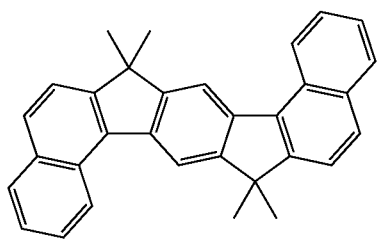
501-4
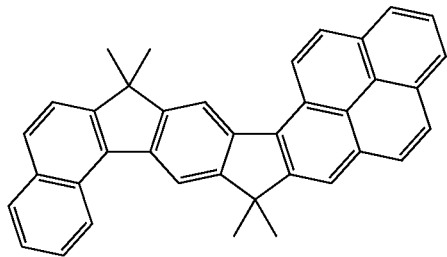
501-5
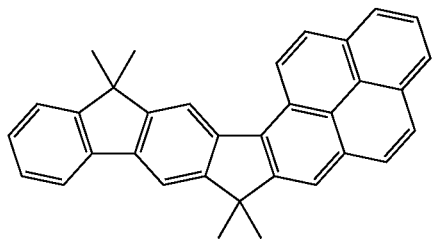
501-6
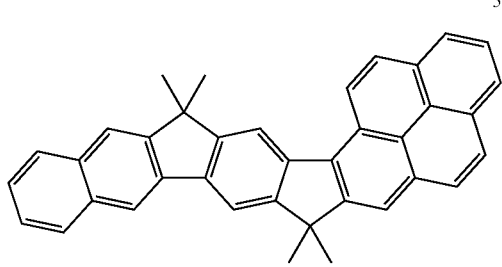
-continued
501-7
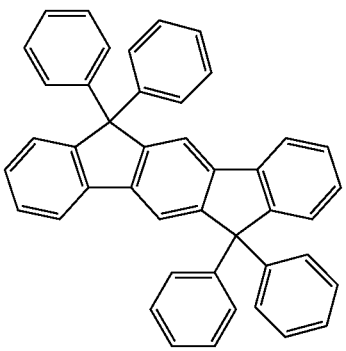
501-8
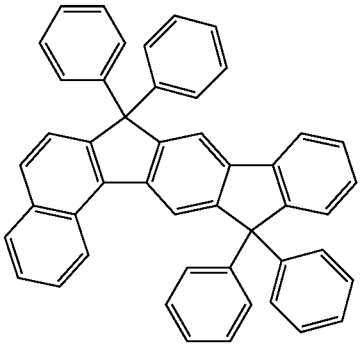
501-9
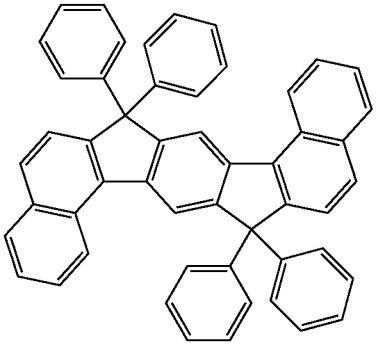
501-10
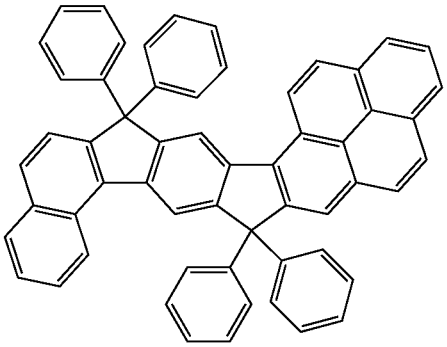

-continued 501-11

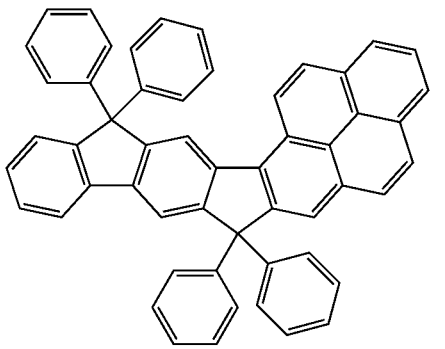

501-12

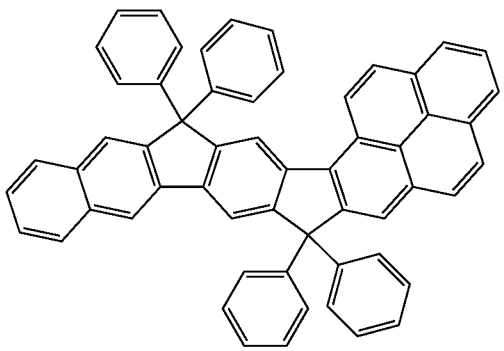

501-13

501-14

501-15

-continued 501-16

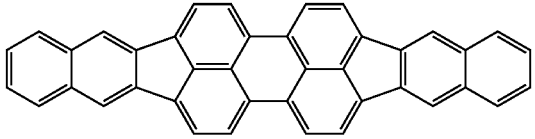

501-17

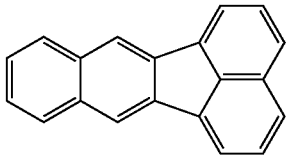

501-18

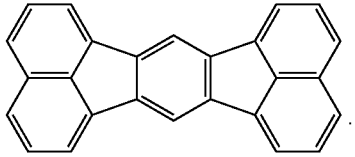

In one or more embodiments, the fluorescent dopant may be selected from a styryl-amine-based compound and a styryl-carbazole-based compound, but embodiments of the present disclosure are not limited thereto.

In one or more embodiments, the fluorescent dopant may be a compound represented by Formula 501:

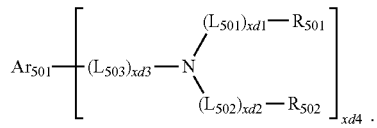

Formula 501

In Formula 501, $Ar_{501}$ may be selected from:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and a group represented by one of Formulae 501-1 to 501-18; and a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and a group represented by one of Formulae 501-1 to 501-18, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group and —Si($Q_{501}$)($Q_{502}$)($Q_{503}$) (where $Q_{501}$ to $Q_{503}$ are each independently selected from hydrogen, a $C_1$-$C_{60}$ alkyl group, a $C_1$-$C_{60}$ alkoxy group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group);

$L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $R_{501}$ and $R_{502}$ may each independently be selected from: a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xd4 may be selected from 0, 1, 2, 3, 4, 5, and 6.

For example, in Formula 501, $Ar_{501}$ may be selected from:
a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and a group represented by one of Formulae 501-1 to 501-18; and a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and a group represented by one of Formulae 501-1 to 501-18, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, and —Si($Q_{501}$)($Q_{502}$)($Q_{503}$) (where $Q_{501}$ to $Q_{503}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group), $L_{501}$ to $L_{503}$ are the same as described in connection with $L_{11}$, xd1 to xd3 may each independently be selected from 0, 1, and 2, xd4 may be selected from 0, 1, 2, and 3, but embodiments of the present disclosure are not limited thereto.

The fluorescent dopant may include, for example, at least one compound selected from Compounds FD(1) to FD(14) and FD1 to FD13:

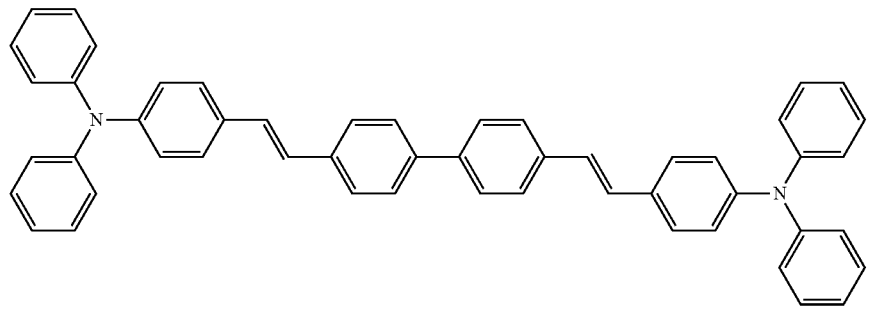

Compound FD(1)

-continued
Compound FD(2)
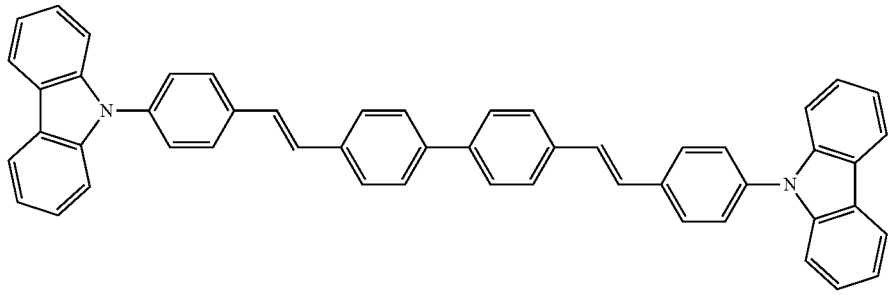
Compound FD(3)
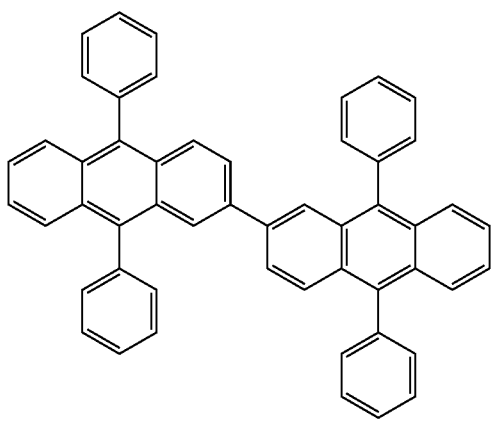
Compound FD(4)
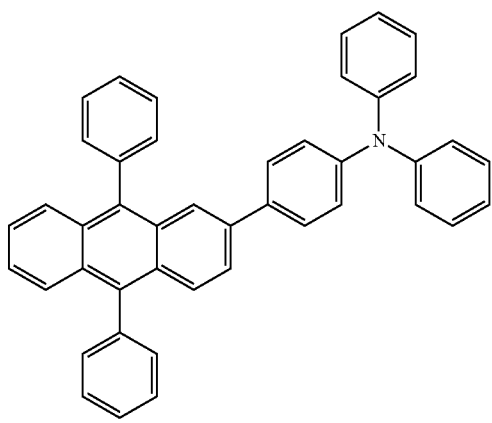
Compound FD(5)
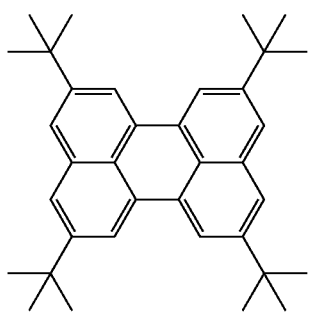
Compound FD(6)
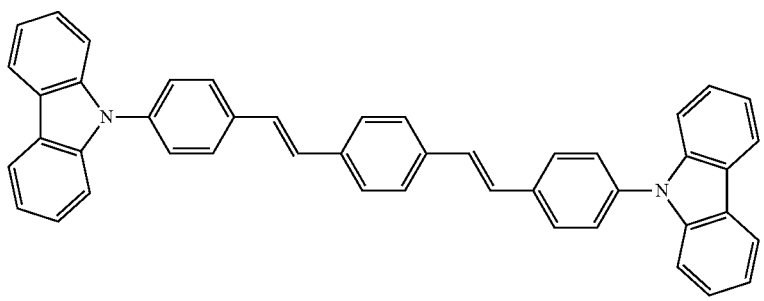

-continued
Compound FD(7)
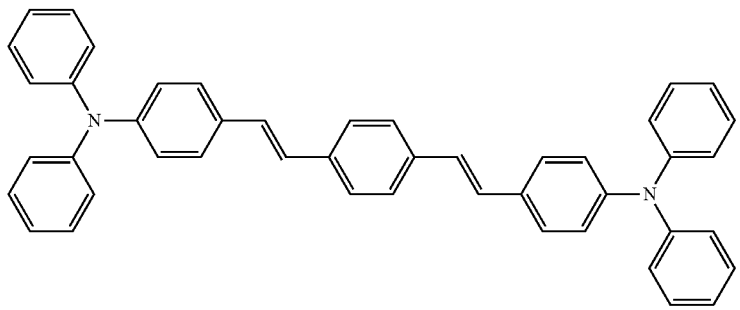
Compound FD(8)
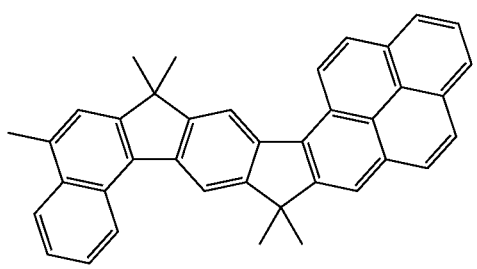
Compound FD(9)
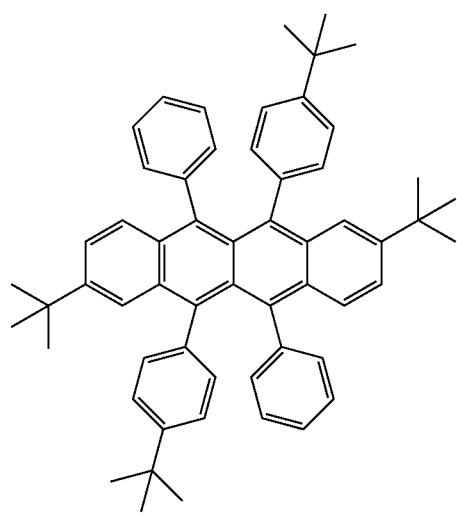
Compound FD(10)
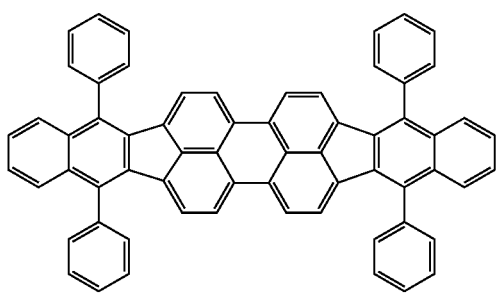
Compound FD(11)
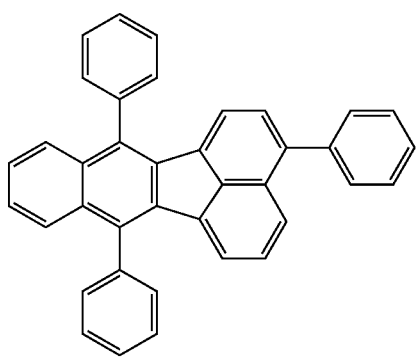
Compound FD(12)
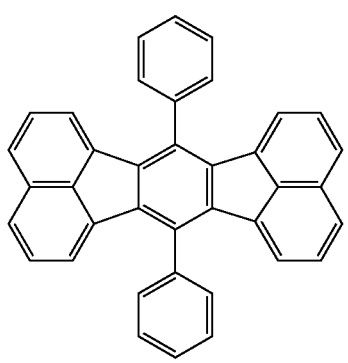
Compound FD(13)
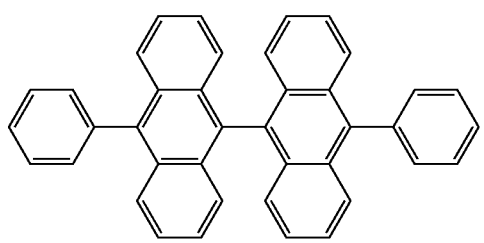

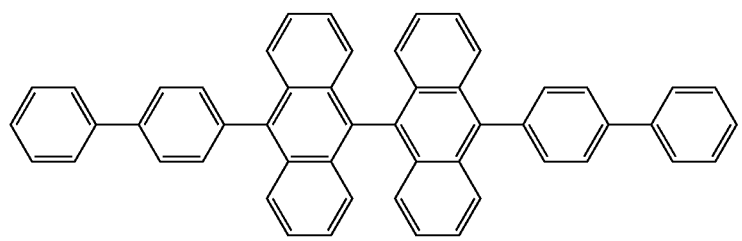
Compound FD(14)
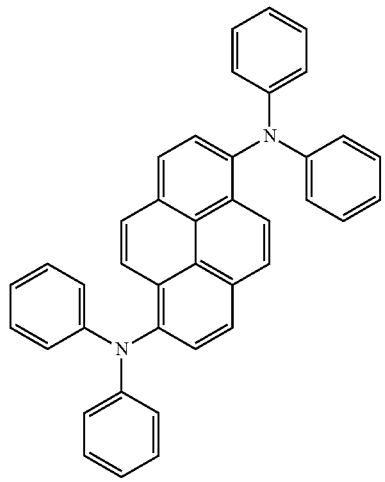
FD1
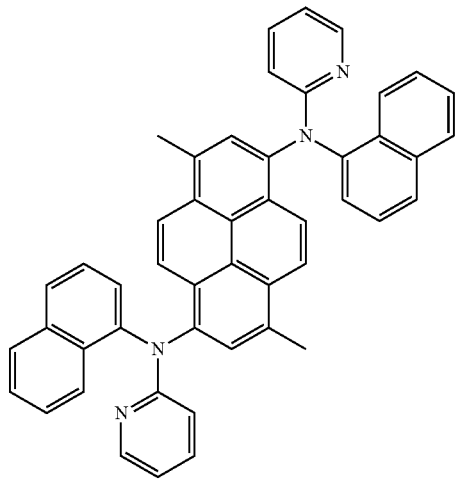
FD2
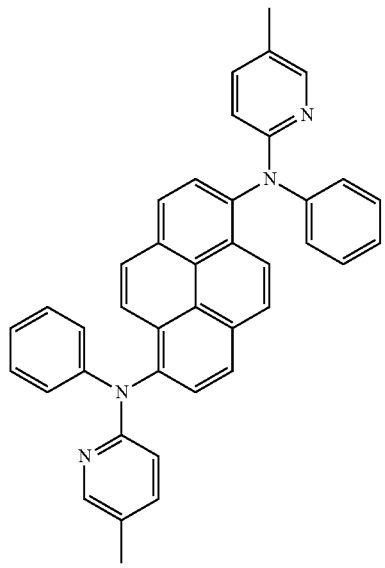
FD3
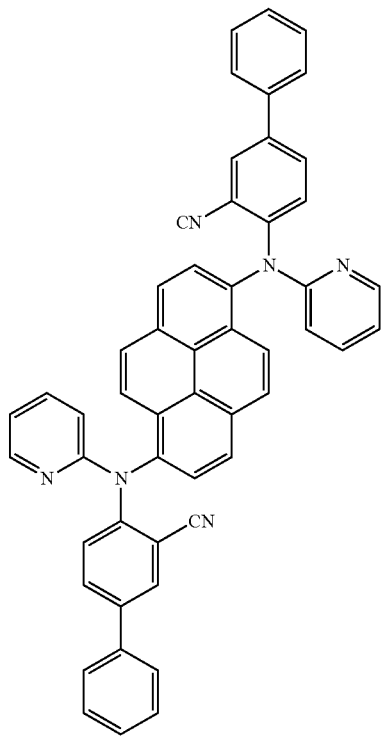
FD4

-continued
FD5
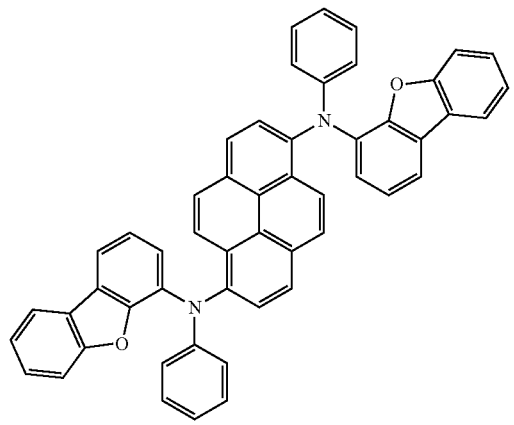
FD6
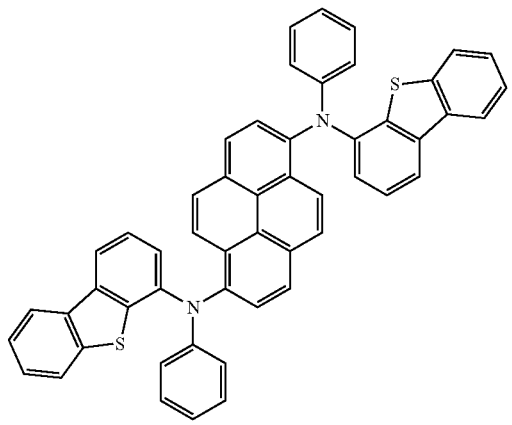
FD7
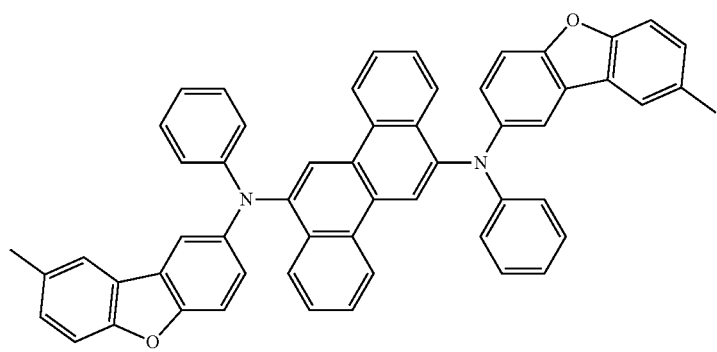
FD8
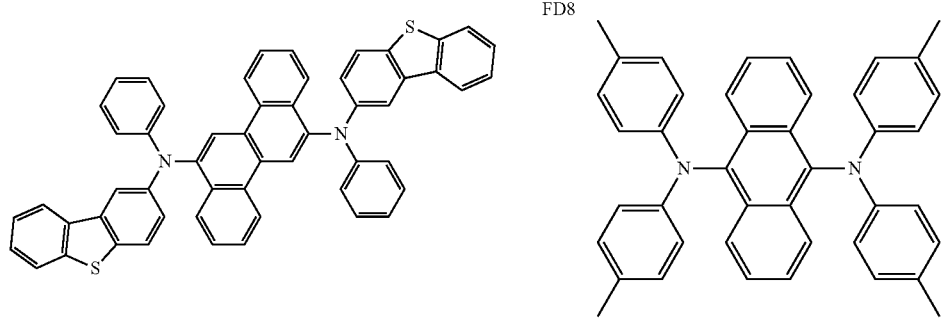
FD9
FD10
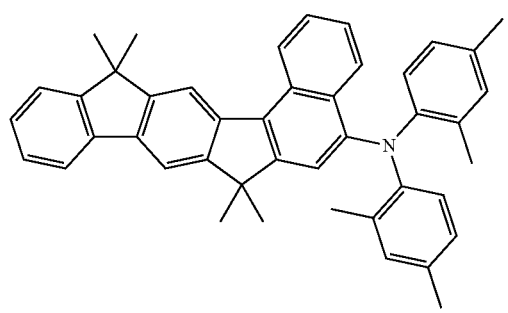

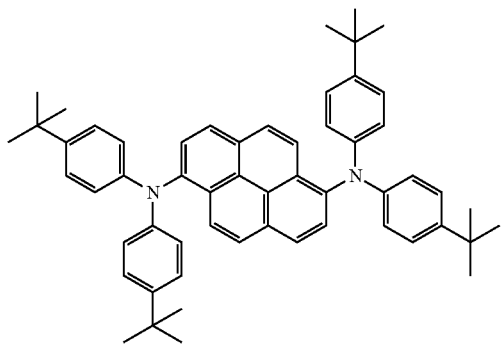

FD11

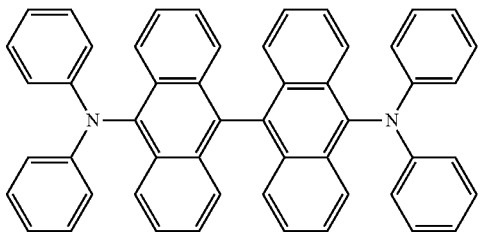

FD12

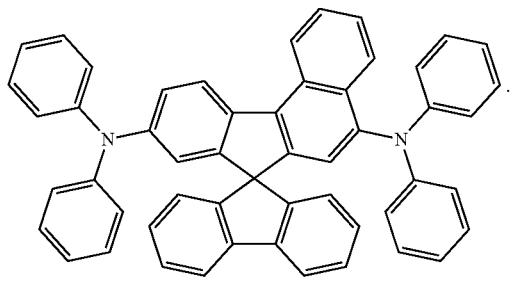

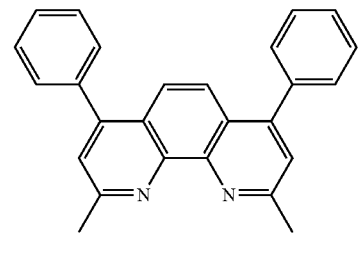

BCP

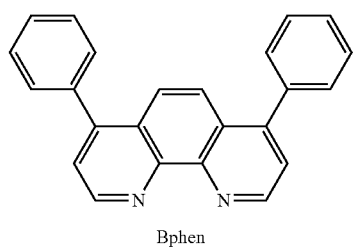

Bphen

FD13

When the emission layer includes a host and a dopant, an amount of the dopant may be in a range of about 0.01 parts to about 15 parts by weight, or may be in a range of about 0.1 parts to about 10 parts by weight, based on 100 parts by weight of the host, but is not limited thereto.

A thickness of the emission layer may be in a range of about 100 Å to about 1,000 Å, for example, about 200 Å to about 400 Å, or for example, about 200 Å to about 600 Å. While not wishing to be bound by theory, it is understood that when the thickness of the emission layer is within this range, excellent light-emission characteristics may be obtained without a substantial increase in driving voltage.

An electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq, but is not limited thereto.

A thickness of the hole blocking layer may be in a range of about 20 Å to about 1,000 Å, for example, about 25 Å to about 750 Å, or for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, BAlq, TAZ, and NTAZ.

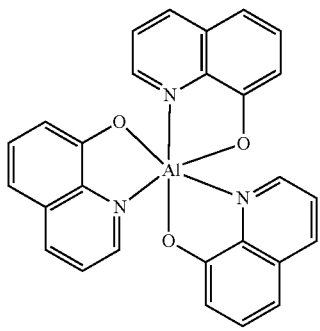

Alq₃

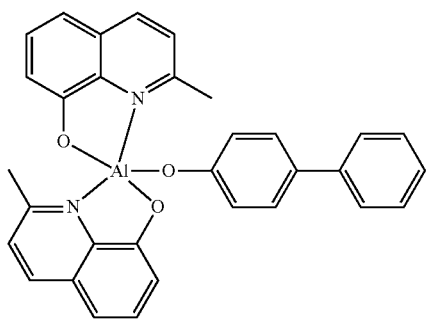

BAlq

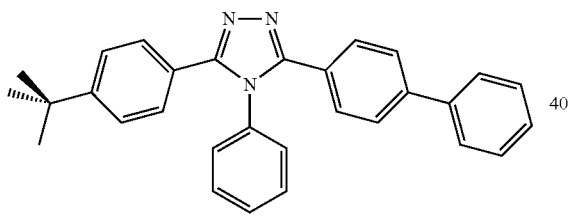

TAZ

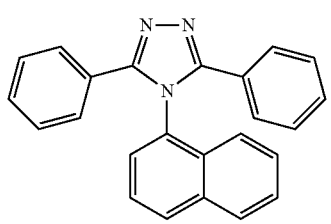

NTAZ

In one or more embodiments, the electron transport layer may include at least one selected from Compounds ET1, ET2, and ET3, but embodiments of the present disclosure are not limited thereto:

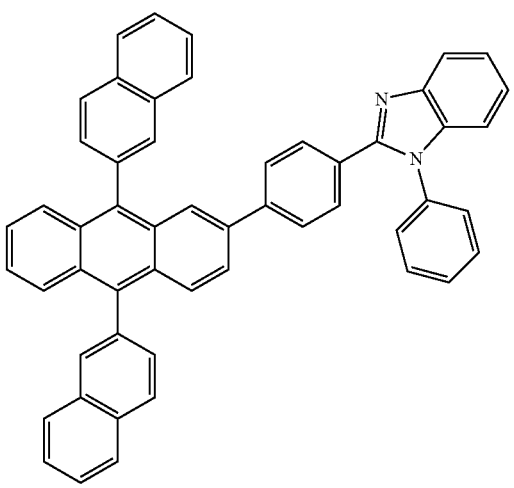

ET1

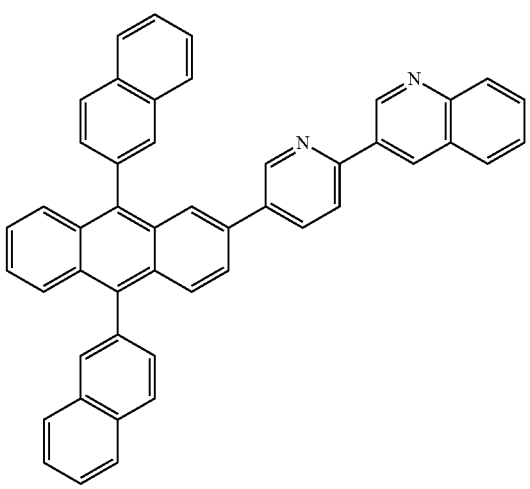

ET2

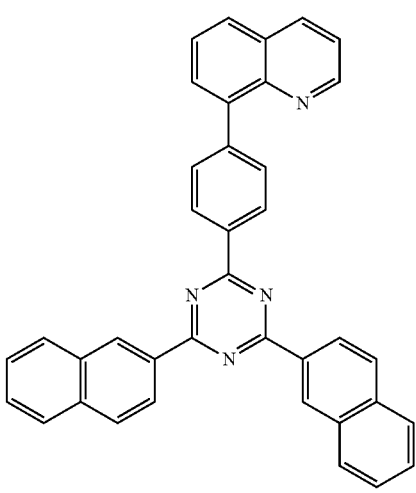

ET3

A thickness of the electron transport layer may be in a range of about 100 Å to about 1,000 Å, for example, about 125 Å to about 750 Å, or for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

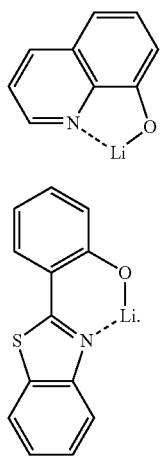

ET-D2

The electron transport region may include an electron injection layer (EIL) that promotes flow of electrons from the second electrode 19 thereinto.

The electron injection layer may include at least one selected from LiF, NaCl, CsF, Li$_2$O, and BaO.

A thickness of the electron injection layer may be in a range of about 1 Å to about 100 Å, and, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be the material for forming the second electrode 19. To manufacture a top-emission type light-emitting device, a transmissive electrode formed using ITO or IZO may be used as the second electrode 19.

Hereinbefore, the organic light-emitting device has been described with reference to the FIGURE, but is not limited thereto.

The term "$C_1$-$C_{60}$ alkyl group" as used herein refers to a linear or branched, saturated aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —OA$_{101}$ (wherein A$_{101}$ is the $C_1$-$C_{60}$ alkyl group). Examples thereof include a methoxy group, an ethoxy group, and an iso-propyloxy (iso-propoxy) group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent hydrocarbon monocyclic group having 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si, and S as a ring-forming atom and 1 to 10 carbon atoms. Examples thereof include a tetrahydrofuranyl group and a tetrahydrothiophenyl group. The term "$C_1$-$C_{10}$ heterocycloalkylene group," as used herein, refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof, and which has no aromaticity in the entire molecular structure. Examples thereof include a cyclopentenyl group, a cyclohexenyl group, and a cycloheptenyl group. The term "$C_3$-$C_{10}$ cycloalkenylene group," as used herein, refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_1$-$C_{10}$ heterocycloalkenyl group are a 2,3-dihydrofuranyl group and a 2,3-dihydrothiophenyl group. The term "$C_1$-$C_{10}$ heterocycloalkenylene group," as used herein, refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group," as used herein, refers to a monovalent group having a cyclic aromatic system that has at least one heteroatom selected from N, O, P, Si, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, P, Si, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_7$-$C_{60}$ arylalkyl group" as used herein refers to -$A_{104}A_{105}$ (wherein $A_{105}$ is a $C_6$-$C_{59}$ aryl group, and $A_{104}$ is a $C_1$-$C_{53}$ alkylene group).

The term "$C_6$-$C_{60}$ aryloxy group" as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

The term "$C_2$-$C_{60}$ heteroaryloxy group" as used herein refers to —$OA_{106}$ (wherein $A_{106}$ is the $C_2$-$C_{60}$ heteroaryl group), and the term "$C_2$-$C_{60}$ heteroarylthio group" as used herein indicates —$SA_{107}$ (wherein $A_{107}$ is the $C_2$-$C_{60}$ heteroaryl group).

The term "$C_3$-$C_{60}$ heteroarylalkyl group" as used herein refers to -$A_{108}A_{109}$ ($A_{109}$ is a $C_2$-$C_{59}$ heteroaryl group, and $A_{108}$ is a $C_1$-$C_{58}$ alkylene group).

The term "monovalent non-aromatic condensed polycyclic group" as used herein refers to a monovalent group (for example, having 8 to 60 carbon atoms) having two or more rings condensed to each other, only carbon atoms as ring-forming atoms, and which has no aromaticity in its entire molecular structure. Examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and which has no aromaticity in its entire molecular structure. Non-limiting examples of the monovalent non-aromatic condensed heteropolycyclic group include a carbazolyl group. The term "divalent non-aromatic condensed heteropolycyclic group," as used herein, refers to a divalent group having the same structure as the monovalent non-aromatic condensed heteropolycyclic group.

The term "$C_5$-$C_{30}$ carbocyclic group" as used herein refers to a saturated or unsaturated cyclic group having, as ring-forming atoms, 5 to 30 carbon atoms only. The $C_5$-$C_{30}$ carbocyclic group may be a monocyclic group or a polycyclic group.

The term "$C_1$-$C_{30}$ heterocyclic group" as used herein refers to a saturated or unsaturated cyclic group having, as a ring-forming atom, at least one heteroatom selected from N, O, Si, P, and S other than 1 to 30 carbon atoms. The term $C_1$-$C_{30}$ heterocyclic group may be a monocyclic group or a polycyclic group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ aryl alkyl group, the substituted $C_1$-$C_{60}$ heteroaryl group, the substituted $C_1$-$C_{60}$ hetero aryloxy group, the substituted $C_1$-$C_{60}$ hetero arylthio group, the substituted $C_2$-$C_{60}$ heteroaryl alkyl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ hetero aryloxy group, a $C_1$-$C_{60}$ hetero arylthio group, a $C_2$-$C_{60}$ heteroaryl alkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ hetero aryloxy group, a $C_1$-$C_{60}$ hetero arylthio group, a $C_2$-$C_{60}$ heteroaryl alkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ hetero aryloxy group, a $C_1$-$C_{60}$ hetero arylthio group, a $C_2$-$C_{60}$ heteroaryl alkyl group, a monovalent non-aromatic condensed polycyclic group, and a monovalent non-aromatic condensed heteropolycyclic group, each substituted with at least one selected from deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ aryl alkyl group, a $C_1$-$C_{60}$ heteroaryl group, a $C_1$-$C_{60}$ hetero aryloxy group, a $C_1$-$C_{60}$ hetero arylthio group, a $C_2$-$C_{60}$ heteroaryl alkyl group, a monovalent non-aromatic condensed polycyclic group, and a monovalent non-aromatic condensed heteropolycyclic group; and —C(=O)($Q_{11}$), —Si($Q_{11}$)($Q_{12}$)($Q_{13}$), and —N($Q_{11}$)($Q_{12}$); wherein $Q_{11}$ to $Q_{13}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ aryl alkyl group, a substituted or unsubstituted $C_1$-$C_{60}$ heteroaryl group, a substituted or unsubstituted $C_1$-$C_{60}$ hetero aryloxy group, a substituted or unsubstituted $C_1$-$C_{60}$ hetero arylthio group, a substituted or unsubstituted $C_2$-$C_{60}$ heteroaryl alkyl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Hereinafter, a compound and an organic light-emitting device according to embodiments of the present disclosure are described in detail with reference to Synthesis Examples and Examples. However, the organic light-emitting device is not limited thereto. The wording "B was used instead of A" used in describing Synthesis Examples means that an amount of A used was identical to an amount of B used, in terms of a molar equivalent.

EXAMPLE

Compounds A to C used in Examples below are as follows:

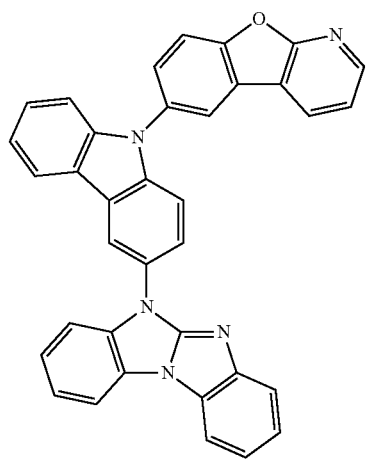

A

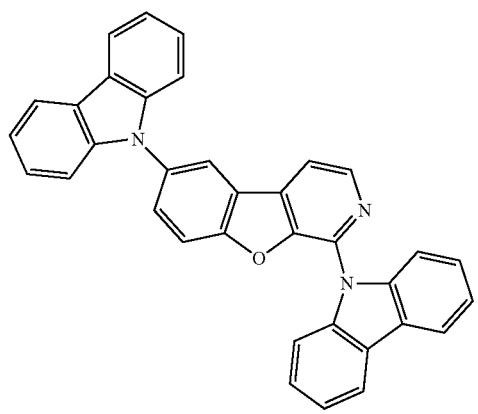

B

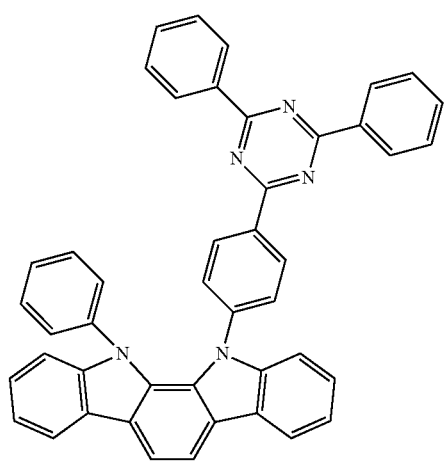

C

Synthesis Example 1: Synthesis of Compound 4

(1) Synthesis of Intermediate 4-1

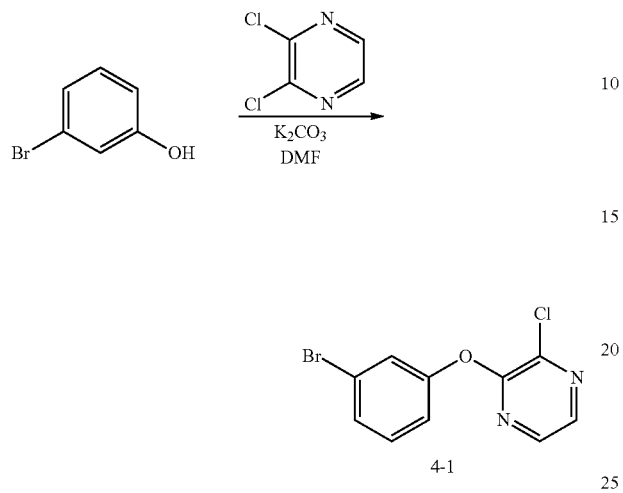

4-1

19.57 grams (g) (113.1 millimoles, mmol) of 3-bromophenol, 18.53 g (124.4 mmol) of 2,3-dichloropyrazine, 15.63 g (113.1 mmol) of $K_2CO_3$, and 113 milliliters (ml) of N,N-dimethylformamide were added to a three-neck flask and heated in a nitrogen atmosphere at a temperature of 80° C. for 4 hours. The reaction mixture was diluted with 300 ml of toluene and filtered by using celite. A filtrate obtained therefrom was washed three times with water. Then, the organic layer was dried by using anhydrous $MgSO_4$. The organic layer was filtered through a silica gel pad with a mixed solvent of toluene and ethyl acetate and concentrated. A solid obtained therefrom was recrystallized by using n-hexane, thereby completing the preparation of 29.53 g (91%) of Intermediate 4-1 as a white solid.

(2) Synthesis of Intermediate 4-2

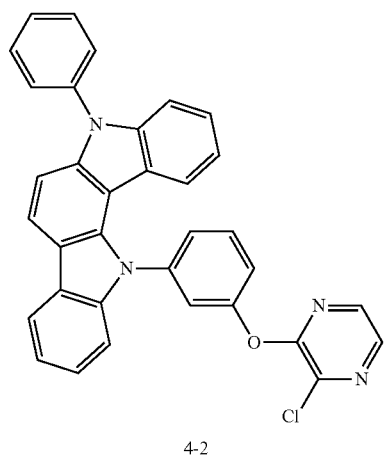

4-2

19.42 g (33 mmol) of Intermediate 4-1, 29.97 g (30 mmol) of Compound a, 4.32 g (45 mmol) of sodium tert-butoxide, 30.55 g (0.6 mmol) of $Pd_2(dba)_3$, 1.21 g of a 50 percent by weight (wt %) tri(tert-butyl)phosphine toluene solution, and 150 ml of toluene were added to a three-neck flask, and the mixture was heated in a nitrogen atmosphere at a temperature of 80° C. for 14 hours. The reaction mixture was diluted with 200 ml of toluene and filtered by using celite. A filtrate obtained therefrom was concentrated and purified by silica gel chromatography (dichloromethane:hexane=8:2 volume to volume, v/v), thereby completing the preparation of 14.47 g (90%) of Intermediate 4-2.

(3) Synthesis of Compound 4

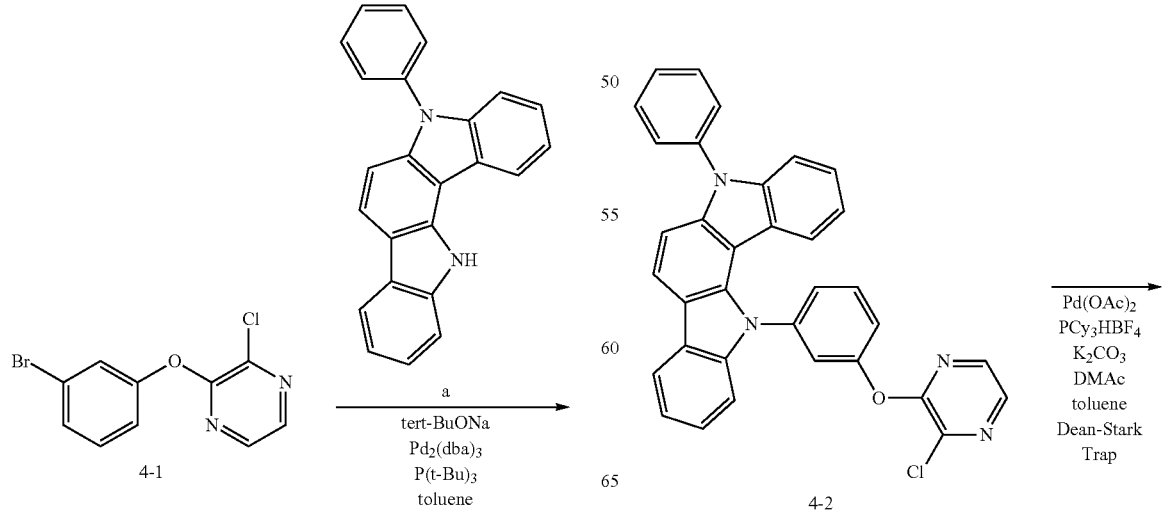

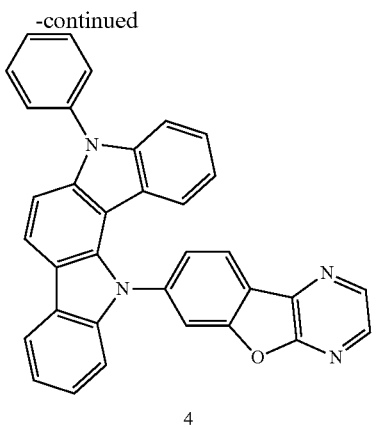

4

114.47 g (27 mmol) of Intermediate 4-2, 7.46 g (54 mmol) of potassium carbonate, 21.21 g (5.4 mmol) of Pd(OAc)$_2$, 3.98 g (10.8 mmol) of tricyclohexylphosphine tetrafluoroborate, 135 ml of N,N-dimethylacetamide (DMAc), and 135 ml of toluene were added to a three-neck flask with a Dean-Stark trap, and the mixture was refluxed in a nitrogen atmosphere for 4 hours. The reaction mixture was diluted with 200 ml of toluene and filtered by using celite. A filtrate obtained therefrom was washed three times by water. Then, the organic layer was dried by using anhydrous MgSO$_4$. The organic layer was filtered through a silica gel pad with a mixed solvent of toluene and ethyl acetate and concentrated. A solid obtained therefrom was purified by silica gel chromatography (dichloromethane), thereby completing the preparation of 4.4 g (32%) of Compound 4. The prepared Compound 4 was identified by MALDI-MS.

MALDI-MS: calc: 500.16 found: 500.19

Evaluation Example of 1: Evaluation of PL Quantum Yield and $\Delta E_{ST}$ of Compounds Samples were prepared by diluting each of Compounds 4, A, B, and C with toluene to a concentration of 0.1 millimolar (mM).

(1) Photoluminescence (PL) quantum yield: PL spectra were measured at room temperature by using a PL measuring apparatus equipped with a xenon lamp (F-7000, manufactured by Hitachi Technologies Corporation). PL quantum yield was obtained by calculating a number of photons absorbed by each sample with respect to a number of photons emitted as PL by each sample.

(2) $\Delta E_{ST}$: As shown in Table 1 below, $T_1$ and $S_1$ energy levels were evaluated with respect to each sample. $\Delta E_{ST}$ was obtained by calculating {($S_1$ energy level)–($T_1$ energy level)} based on the obtained result.

The obtained PL quantum yield and $\Delta E_{ST}$ are shown in Table 2 below.

TABLE 1

| | |
|---|---|
| $T_1$ energy level evaluation method | Samples are prepared by diluting each of Compounds 4, A, B, and C with toluene to a concentration of 0.1 mM. Each of the samples is added to a quartz cell, and the mixture is added to liquid nitrogen (77 Kelvin, K). A phosphorescence spectrum is measured in a phosphorescence measurement mode by using a PL measuring apparatus (F-7000, manufactured by Hitachi Technologies Corporation), and a $T_1$ energy level is calculated from a start wavelength of a short wavelength side of the phosphorescence spectrum. |

TABLE 1-continued

| | |
|---|---|
| $S_1$ energy level evaluation method | Samples are prepared by diluting each of Compounds 4, A, B, and C with toluene to a concentration of 0.1 mM. Each of the samples is added to a quartz cell. Then, a PL spectrum is measured at room temperature by using a PL measuring apparatus (F-7000, manufactured by Hitachi Technologies Corporation), and an $S_1$ energy level is calculated from a start wavelength of a short wavelength side of the PL spectrum. |

TABLE 2

| Compound No. | PL quantum yield (%) | $\Delta E_{ST}$ (eV) |
|---|---|---|
| 4 | 100 | 0.09 |
| A | 1 | 0.15 |
| B | 4 | 0.35 |
| C | 110 | 0.08 |

Referring to Table 2, it was determined that Compound 4 had higher PL quantum yield than the yield of Compounds A and B.

Evaluation Example 2: Evaluation of Deposition Temperature

Deposition temperatures of Compounds 4, A, B, and C were measured by using a resistive-heating type deposition apparatus. Results thereof are shown in Table 3. Referring to Table 3, it was determined that Compound 4 had a lower deposition temperature than those of Compounds A to C.

TABLE 3

| Compound No. | Deposition temperature (° C.) |
|---|---|
| 4 | 195 |
| A | 290 |
| B | 240 |
| C | 250 |

Example 1

An ITO glass substrate was cut to a size of 50 mm×50 mm×0.5 mm (mm=millimeter), sonicated in acetone isopropyl alcohol and pure water, each solvent for 15 minutes, and then washed by exposing the ITO glass substrate to UV irradiation and ozone for 30 minutes.

Then, m-MTDATA was deposited on an ITO electrode (anode) of the ITO glass substrate at a deposition rate of 1 Angstroms per second (Å/sec) to form a hole injection layer having a thickness of 600 Å, and α-NPD was deposited on the hole injection layer at a deposition rate of 1 Å/sec to form a hole transport layer having a thickness of 250 Å.

Compound H-25 (host) and Compound 4 (dopant) were each co-deposited on the hole transport layer at a deposition rate of 0.15 Å/sec and 1 Å/sec to form an emission layer having a thickness of 400 Å.

BAlq was deposited on the emission layer at a deposition rate of 1 Å/sec to form a hole blocking layer having a thickness of 50 Å, Alq$_3$ was deposited on the hole blocking layer to form an electron transport layer having a thickness of 300 Å, LiF was deposited on the electron transport layer to form an electron injection layer having a thickness of 10 Å, and Al was vacuum-deposited on the electron injection layer to form a second electrode (cathode) having a thickness of 1,200 Å, thereby completing the manufacture of an organic light-emitting device.

Comparative Examples 1 to 3

Organic light-emitting devices of Comparative Examples 1 to 3 were manufactured in the same manner as in Example 1, except that Compounds shown in Table 4 were each used instead of Compound 4 as a dopant in forming an emission layer.

Evaluation Example 3: Evaluation of Characteristics of Organic Light-Emitting Devices The external quantum efficiency and lifespan ($T_{95}$) of the organic light-emitting devices manufactured according to Example 1 and Comparative Examples 1 to 3 were evaluated. Results thereof are shown in Table 4. This evaluation was performed by using a current-voltage meter (Keithley 2400) and a luminance meter (Minolta Cs-1000A). The lifespan ($T_{95}$) (at 500 nit) indicates an amount of time that has lapsed when luminance reaches 95% of initial luminance (100%), and the lifespan ($T_{95}$) is a relative value based on a value of Comparative Example 3.

TABLE 4

| | Dopant | External quantum efficiency (%) | Lifespan (relative value) |
|---|---|---|---|
| Example 1 | Compound 4 | 15 | 600 |
| Comparative Example 1 | Compound A | 0.5 | <1 |
| Comparative Example 2 | Compound B | 1.1 | <5 |
| Comparative Example 3 | Compound C | 13 | 100 |

Referring to Table 4, it was determined that the organic light-emitting device of Example 1 had excellent light emission efficiency and lifespan characteristics as compared with those characteristics of Comparative Examples 1 to 3.

Since the condensed cyclic compound has excellent electrical characteristics and thermal stability, an organic light-emitting device including the condensed cyclic compound may have excellent light emission efficiency, color purity, and lifespan characteristics. Also, since the condensed cyclic compound may be deposited at a relatively low temperature, the organic light-emitting device including the condensed cyclic compound may be easily manufactured.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:
1. A condensed cyclic compound represented by Formula 1:

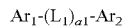

Formula 1

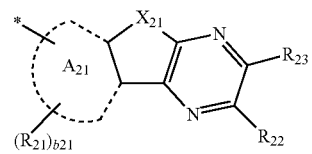

Formula 2-3

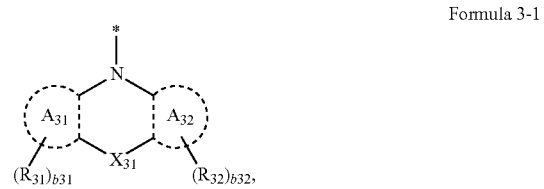

Formula 3-1 wherein, in Formulae 1, 2-3, and 3-1,
$Ar_1$ is a group represented by Formula 2-3,
$Ar_2$ is a group represented by Formula 3-1,
$L_1$ is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
a1 is selected from 0, 1, 2, and 3,
$X_{21}$ is selected from O, S, and Se,
$X_{31}$ is selected from a single bond, O, S, N($R_{33}$), C($R_{33}$)($R_{34}$), Si($R_{33}$)($R_{34}$), Ge($R_{33}$)($R_{34}$), and P(=O)($R_{33}$),
$A_{21}$, $A_{31}$, and $A_{32}$ are each independently selected from a $C_5$-$C_{30}$ carbocyclic group and a $C_1$-$C_{30}$ heterocyclic group,
$R_{21}$ to $R_{23}$ and $R_{31}$ to $R_{34}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ aryl alkyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ heteroaryl alkyl group, a substituted or unsubstituted $C_1$-$C_{60}$ hetero aryloxy group, a substituted or unsubstituted $C_1$-$C_{60}$ hetero arylthio group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_1$)($Q_2$)($Q_3$), and —B($Q_1$)($Q_2$),
$R_{22}$ and $R_{23}$ are optionally linked to form a substituted or unsubstituted $C_5$-$C_{30}$ carbocyclic group or a substituted or unsubstituted $C_1$-$C_{30}$ heterocyclic group,
$R_{33}$ and $R_{34}$ are optionally linked via a first linking group to form a substituted or unsubstituted $C_5$-$C_{30}$ carbocyclic group or a substituted or unsubstituted $C_1$-$C_{30}$ heterocyclic group, b21, b31, and b32 are each independently selected from 1, 2, 3, 4, 5, 6, 7, and 8, $Q_1$ to $Q_3$ are each independently selected from:

hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, substituted with at least one selected from deuterium, a $C_1$-$C_{60}$ alkyl group, and a $C_6$-$C_{60}$ aryl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ arylalkyl group, a $C_6$-$C_{60}$ aryloxy group, a $C_6$-$C_{60}$ arylthio group, a $C_1$-$C_{60}$ heteroaryl group, a $C_2$-$C_{60}$ heteroaryl alkyl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group; and a $C_6$-$C_{60}$ aryl group, substituted with at least one selected from deuterium, a $C_1$-$C_{60}$ alkyl group, and a $C_6$-$C_{60}$ aryl group, and indicates a binding site to a neighboring atom.

2. The condensed cyclic compound of claim 1, wherein $L_1$ is selected from:

a phenylene group, a naphthylene group, a fluorenylene group, a phenanthrenylene group, an anthracenylene group, a triphenylenylene group, a pyrenylene group, a chrysenylene group, a pyridinylene group, a pyrazinylene group, a pyrimidinylene group, and a triazinylene group; and a phenylene group, a naphthylene group, a fluorenylene group, a phenanthrenylene group, an anthracenylene group, a triphenylenylene group, a pyrenylene group, a chrysenylene group, a pyridinylene group, a pyrazinylene group, a pyrimidinylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a triphenylenyl group, a pyrenyl group, a chrysenyl group, a pyridinyl group, a pyrazinyl group, a pyrimidinyl group, and a triazinyl group.

3. The condensed cyclic compound of claim 1, wherein a1 is 0 or 1.

4. The condensed cyclic compound of claim 1, wherein a1 iso.

5. The condensed cyclic compound of claim 1, wherein $A_{21}$ is selected from a benzene group, a naphthalene group, a phenanthrene group, a pyrene group, a chrysene group, a triphenylene group, a fluoranthene group, an indene group, a fluorene group, a benzofluorene group, a dibenzofluorene group, a spiro-bifluorene group, a pyridine group, a pyrimidine group, a quinoline group, an isoquinoline group, an indole group, a carbazole group, a benzocarbazole group, a dibenzocarbazole group, a furan group, a benzofuran group, a dibenzofuran group, a naphtho furan group, a benzo naphtho furan group, a dinaphtho furan group, a thiophene group, a benzothiophene group, a dibenzothiophene group, a naphtho thiophene group, a benzonaphtho thiophene group, and a dinaphtho thiophene group.

6. The condensed cyclic compound of claim 1, wherein $A_{21}$ is selected from a benzene group, a naphthalene group, a phenanthrene group, a pyrimidine group, a quinoline group, and an isoquinoline group.

7. The condensed cyclic compound of claim 1, wherein $Ar_1$ is selected from groups represented by Formulae 2-11 to 2-14:

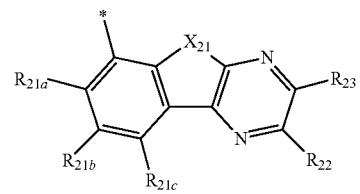

2-11

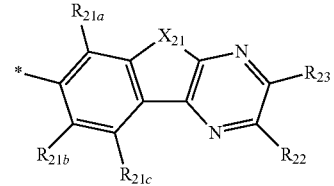

2-12

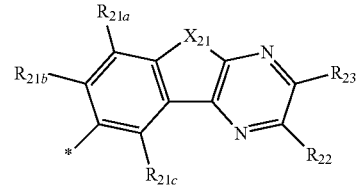

2-13

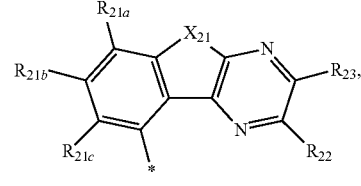

2-14 wherein, in Formulae 2-11 to 2-14, $X_{21}$, $R_{22}$, and $R_{23}$ are the same as described in Formula 2-3, $R_{21a}$ to $R_{21d}$ are each independently the same as described in connection with $R_{21}$ in Formula 2-3, and indicates a binding site to a neighboring atom.

8. The condensed cyclic compound of claim 1, wherein $X_{31}$ is selected from a single bond, O, S, N($R_{33}$), and C($R_{33}$)($R_{34}$).

9. The condensed cyclic compound of claim 1, wherein $A_{31}$ and $A_{32}$ are each independently selected from a benzene group, a naphthalene group, a phenanthrene group, a pyrene group, a chrysene group, a triphenylene group, a fluoranthene group, an indene group, a fluorene group, a benzofluorene group, a dibenzofluorene group, a spiro-bifluorene group, a pyridine group, a pyrimidine group, a quinoline group, an isoquinoline group, an indole group, a carbazole group, a benzocarbazole group, a dibenzocarbazole group, a furan group, a benzofuran group, a dibenzofuran group, a naphtho furan group, a benzonaphtho furan group, a dinaphtho furan group, a thiophene group, a benzothiophene group, a dibenzothiophene group, a naphtho thiophene group, a benzonaphtho thiophene group, and a dinaphtho thiophene group.

10. The condensed cyclic compound of claim 1, wherein $A_{31}$ and $A_{32}$ are each independently selected from a benzene group, a naphthalene group, a phenanthrene group, an indene group, a fluorene group, a benzofluorene group, a dibenzofluorene group, a pyridine group, a pyrimidine group, a quinoline group, an isoquinoline group, an indole group, a carbazole group, a benzocarbazole group, a dibenzocarbazole group, a benzofuran group, a dibenzofuran group, a naphtho furan group, a benzonaphtho furan group, a dinaphtho furan group, a benzothiophene group, a dibenzothiophene group, a naphtho thiophene group, a benzonaphtho thiophene group, and a dinaphtho thiophene group.

11. The condensed cyclic compound of claim 1, wherein $Ar_2$ is selected from groups represented by Formulae 3-11 to 3-17:

3-11

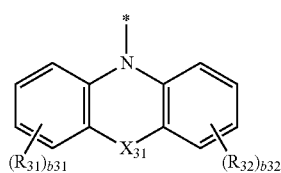

3-12

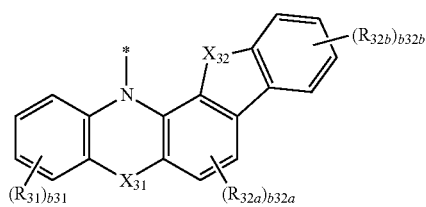

3-13

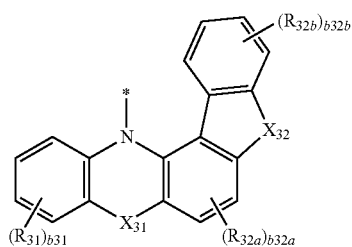

3-14

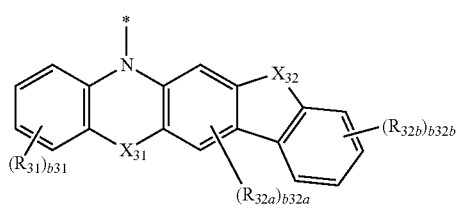

3-15

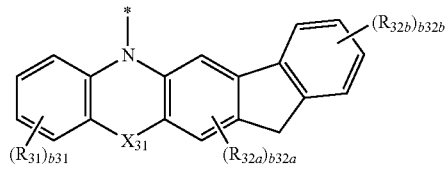

3-16

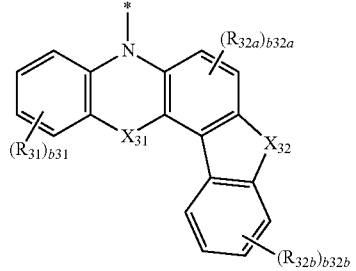

3-17

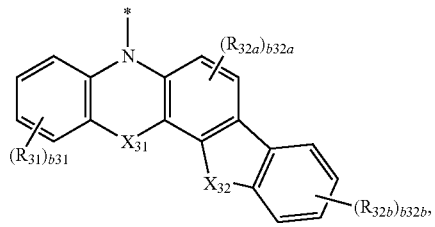

wherein, in Formulae 3-11 to 3-17, $X_{31}$, $R_{31}$, $R_{32}$, b31, and b32 are the same as described in Formula 3-1, $X_{32}$ is selected from O, S, $N(R_{32c})$, and $C(R_{32c})(R_{32d})$, $R_{32a}$ to $R_{32d}$ are each independently the same as described in connection with $R_{32}$ in Formula 3-1, b32a and b32b are each independently the same as described in connection with b32 in Formula 3-1, and * indicates a binding site to a neighboring atom.

12. The condensed cyclic compound of claim 1, wherein $R_{21}$ to $R_{23}$ and $R_{31}$ to $R_{34}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a pyridinyl group, a pyrimidinyl group, and a triazinyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a piperidinyl group, a tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a piperidinyl group, tetrahydro-2H-pyranyl group, a tetrahydro-2H-thiopyranyl group, a phenyl group, a fluorenyl group, a dibenzosilolyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a furanyl group, a thiophenyl group, a thiazolyl group, an isothiazolyl group, an isoxazolyl group, an oxazolyl group, a triazolyl group, a tetrazolyl group, an oxadiazolyl group, a triazinyl group, a carbazolyl group, a dibenzofuranyl group, a dibenzothiophenyl group, —Si($Q_{31}$)($Q_{32}$)($Q_{33}$), —N($Q_{31}$)($Q_{32}$), and —B($Q_{31}$)($Q_{32}$); and —Si($Q_1$)($Q_2$)($Q_3$), —N($Q_1$)($Q_2$), and —B($Q_1$)($Q_2$), $R_{22}$ and $R_{23}$ are optionally linked to form a substituted or unsubstituted $C_5$-$C_{30}$ carbocyclic group or a substituted or unsubstituted $C_1$-$C_{30}$ heterocyclic group, $R_{33}$ and $R_{34}$ are optionally linked via a first linking group to form a substituted or unsubstituted $C_5$-$C_{30}$ carbocyclic group or a substituted or unsubstituted $C_1$-$C_{30}$ heterocyclic group, and $Q_1$ to $Q_3$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group.

13. The condensed cyclic compound of claim 1, wherein the condensed cyclic compound represented by Formula 1 is represented by one of Formulae 1-1 to 1-10:

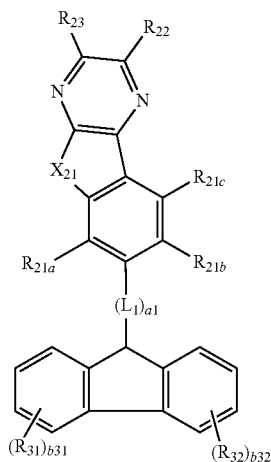

1-1

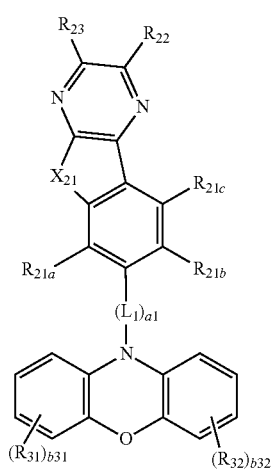

1-2

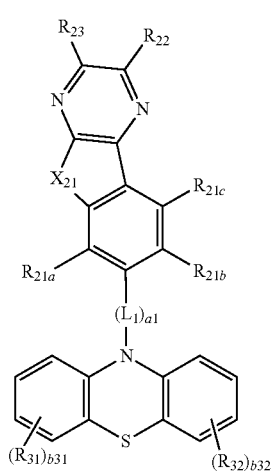

1-3

-continued
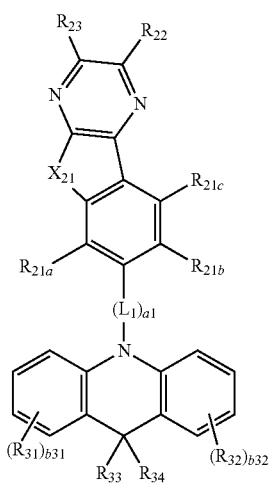
1-4
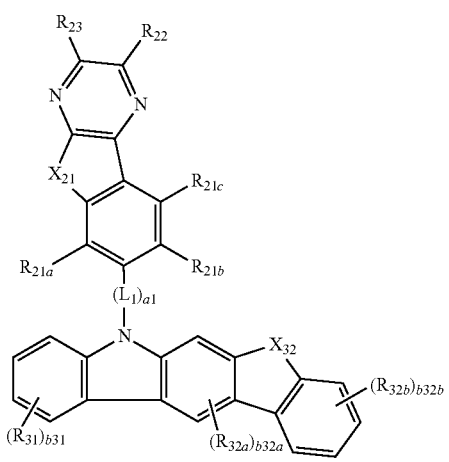
1-7
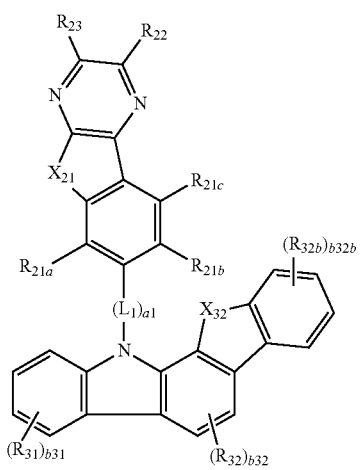
1-5
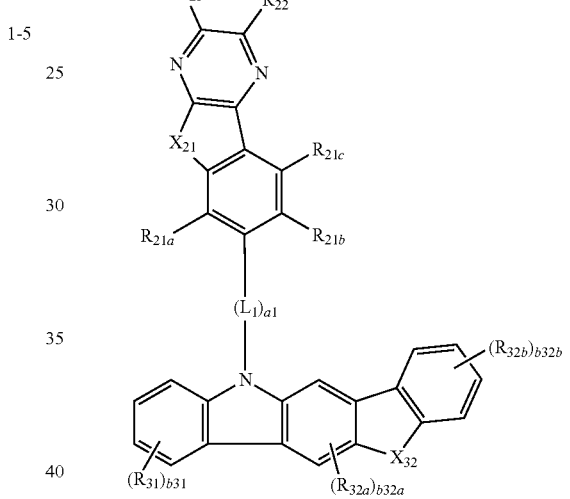
1-8
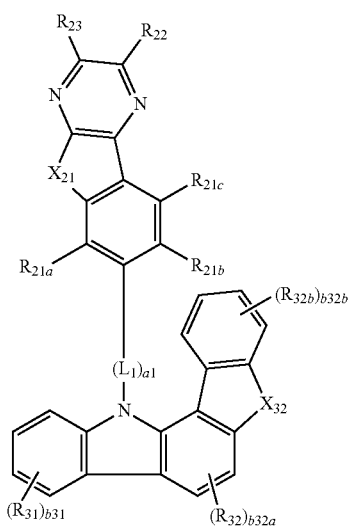
1-6
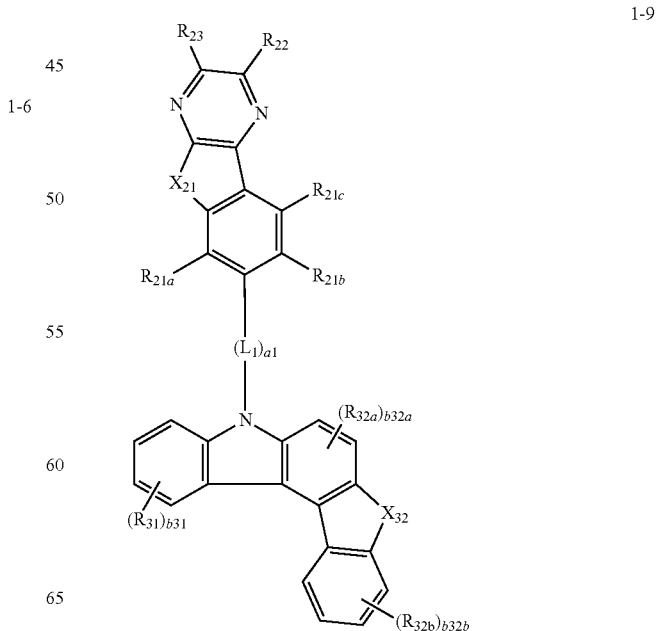
1-9

-continued 1-10

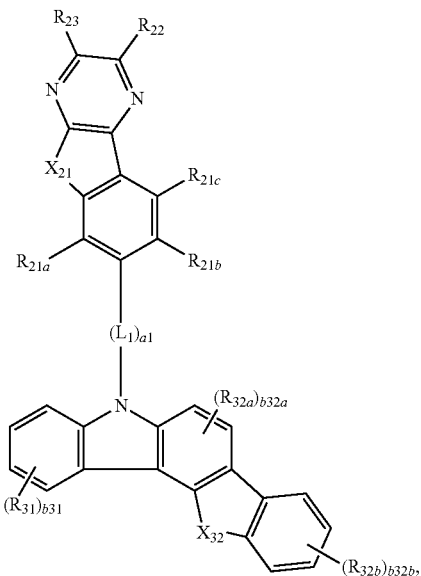

wherein, in Formulae 1-1 to 1-10, $L_1$ and a1 are the same as described in Formula 1, $X_{21}$, $R_{22}$, and $R_{23}$ are the same as described in Formulae 2-1 to 2-3, $R_{21a}$ to $R_{21c}$ are each independently the same as described in connection with $R_{21}$ in Formulae 2-1 to 2-3, $R_{31}$ to $R_{34}$, b31, and b32 are the same as described in Formula 3-1, $X_{32}$ is selected from O, S, $N(R_{32c})$, and $C(R_{32c})(R_{32d})$, $R_{32a}$ to $R_{32d}$ are each independently the same as described in connection with $R_{32}$ in Formula 3-1, and b32a and b32b are each independently the same as described in connection with b32 in Formula 3-1.

14. The condensed cyclic compound of claim 1, wherein a molecular weight of the condensed cyclic compound represented by Formula 1 is 1,000 grams per mole or less.

15. The condensed cyclic compound of claim 1, wherein the condensed cyclic compound represented by Formula 1 satisfies Equation 1:

$$0 \text{ electron volts} \leq \Delta E_{ST} \leq 0.3 \text{ electron volts}, \quad \text{Equation 1}$$

wherein, in Equation 1, $\Delta E_{ST}$ is a difference between the lowest excitation singlet energy level ($E_{S1}$) of the condensed cyclic compound represented by Formula 1 and the lowest excitation triplet energy level ($E_{T1}$) of the condensed cyclic compound represented by Formula 1.

16. An organic light-emitting device comprising:
a first electrode;
a second electrode; and
an organic layer disposed between the first electrode and the second electrode,
wherein the organic layer comprising an emission layer, and
wherein the organic layer comprises at least one condensed cyclic compound represented by Formula 1 of claim 1.

17. The organic light-emitting device of claim 16, wherein the first electrode is an anode,
the second electrode is a cathode, and
the organic layer comprises a hole transport region disposed between the first electrode and the emission layer and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

18. The organic light-emitting device of claim 16, wherein the emission layer comprises at least one condensed cyclic compound represented by Formula 1.

19. A condensed cyclic compound selected from Compounds 1 to 84:

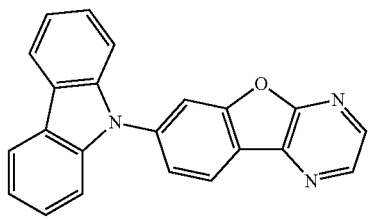

1

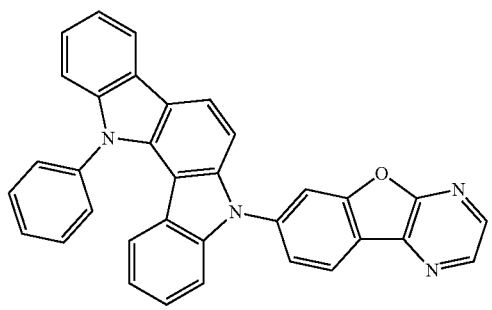

2

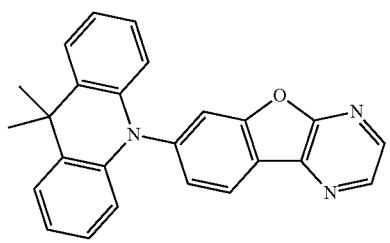

3

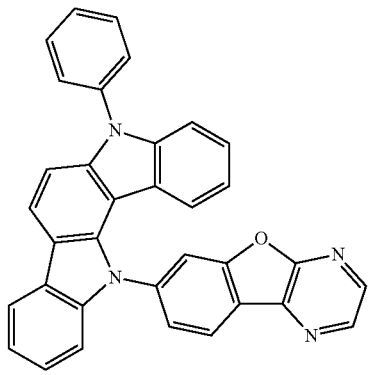

4

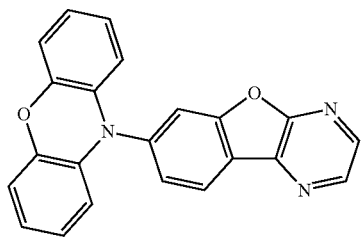
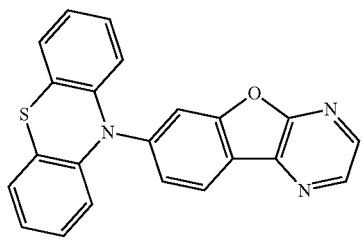
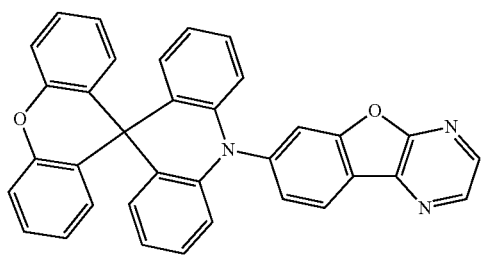
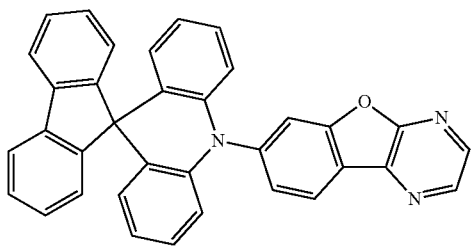
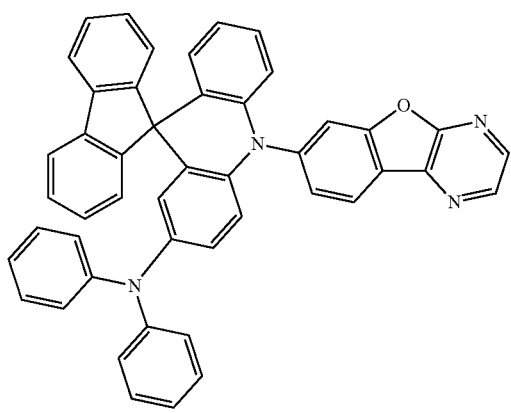
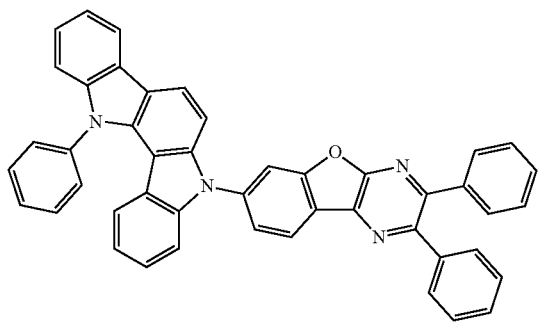
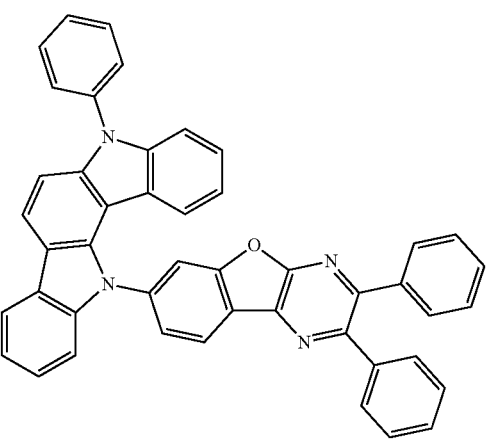
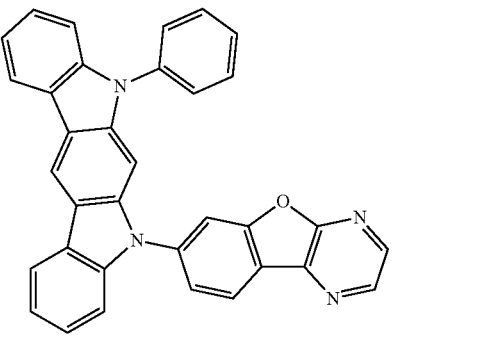
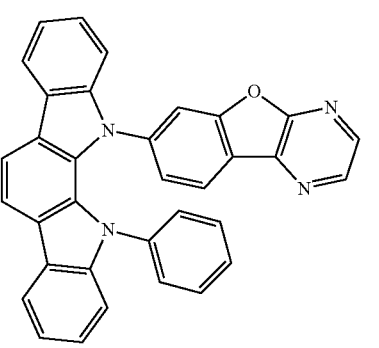

137
-continued
14
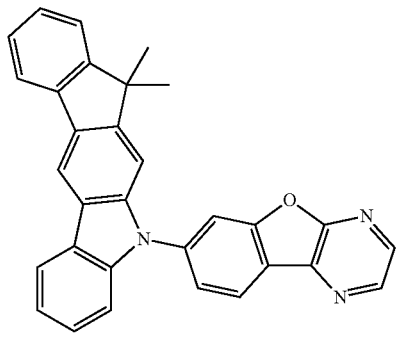
15
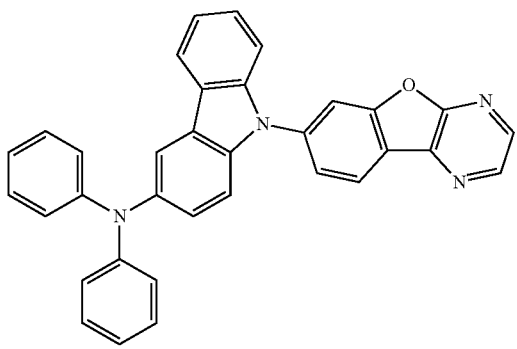
16
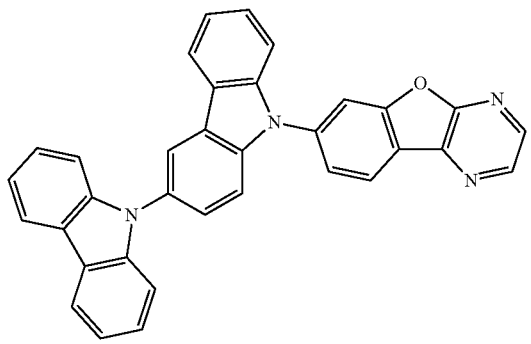
17
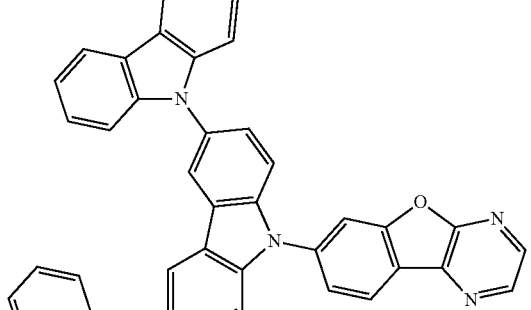
138
-continued
18
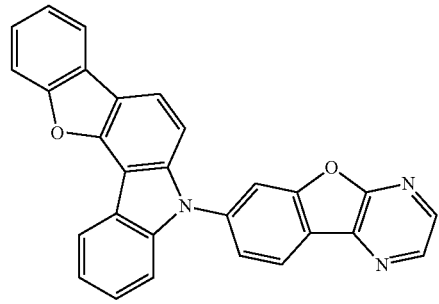
19
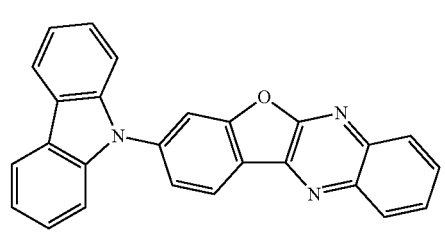
20
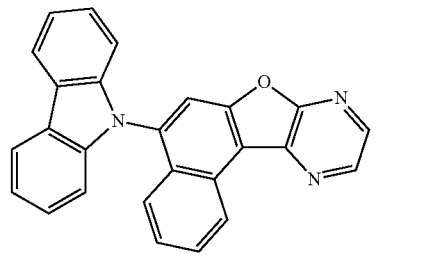
21
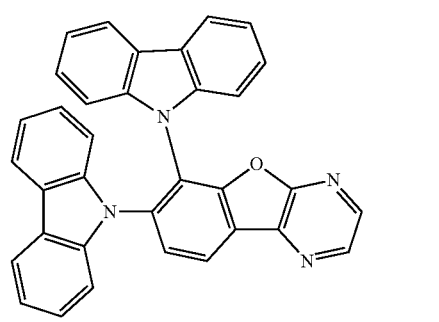
22
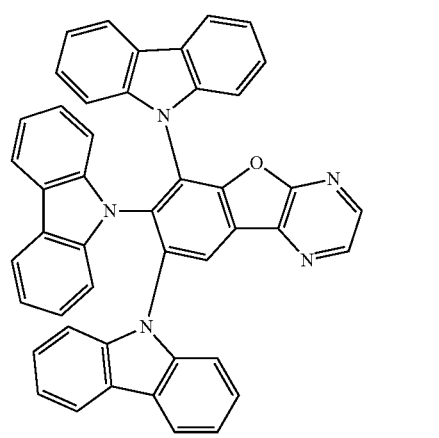

-continued
23
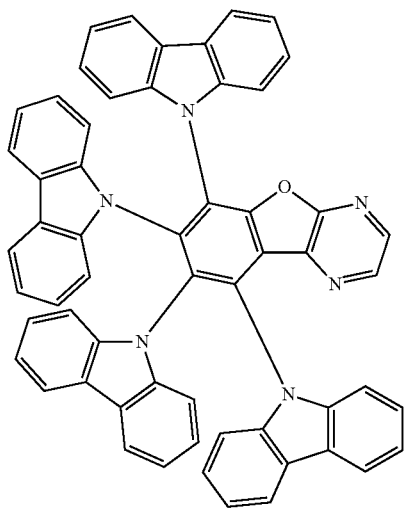
24
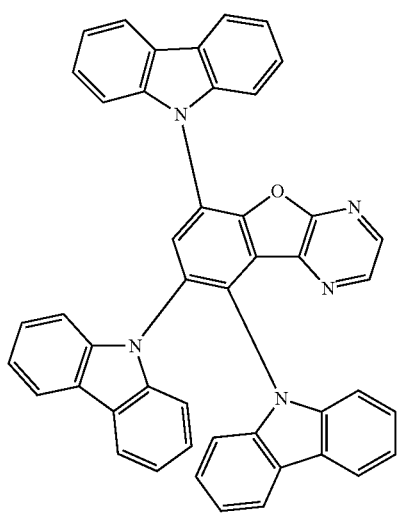
25
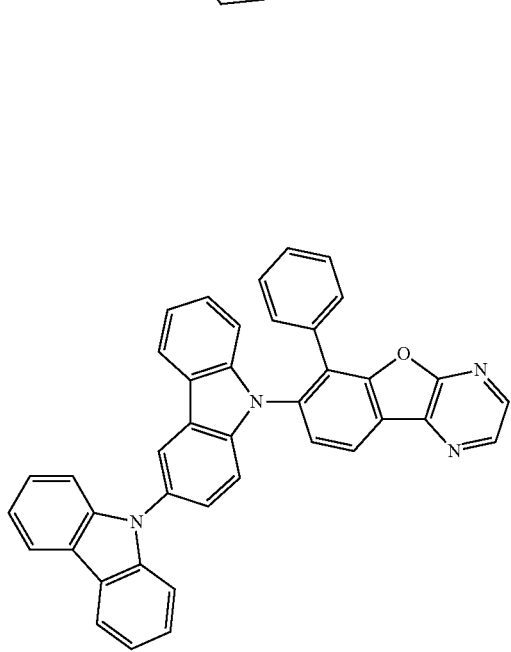
-continued
26
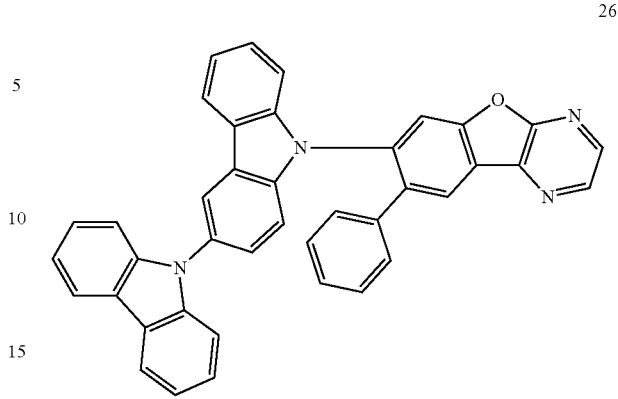
27
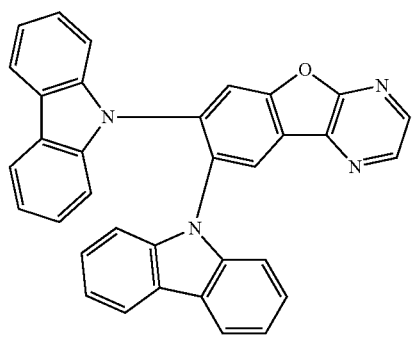
28
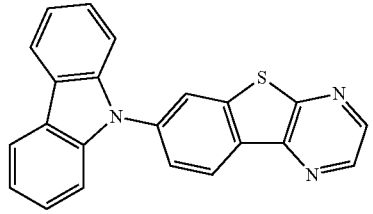
29
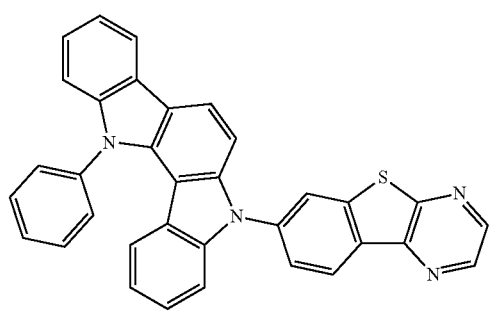
30
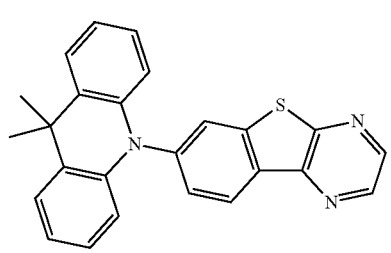

31
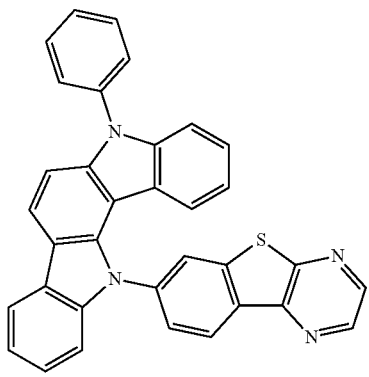
32
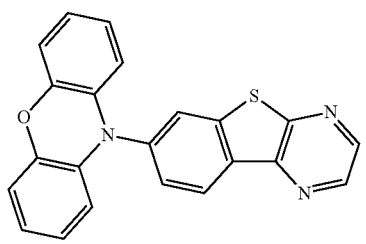
33
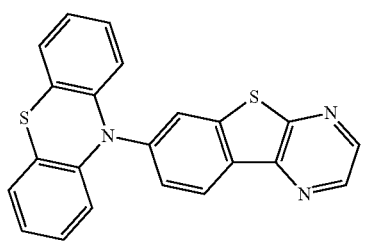
34
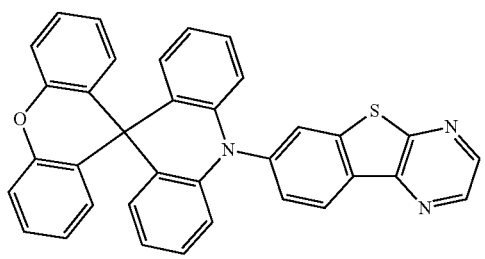
35
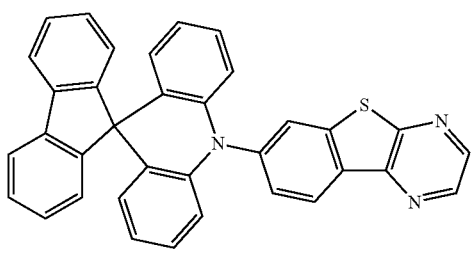
36
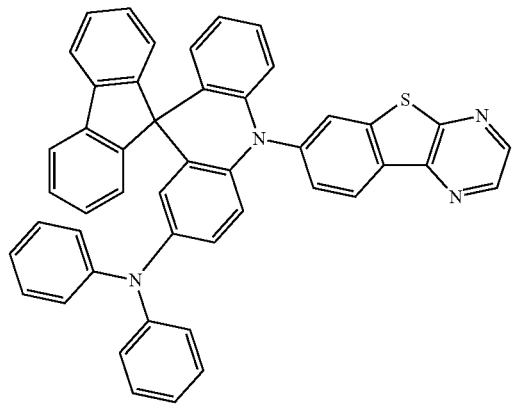
37
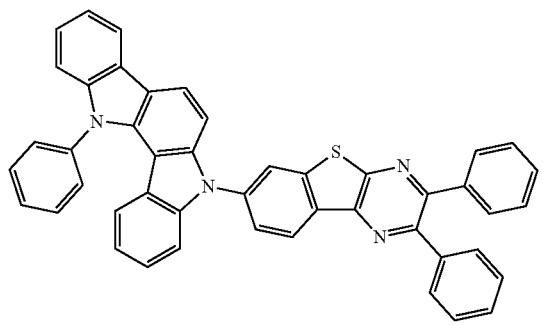
38
39
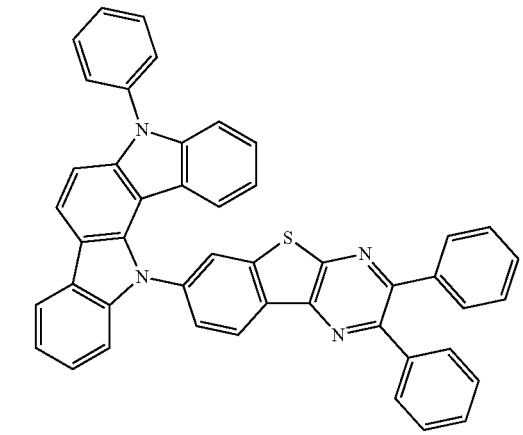

40
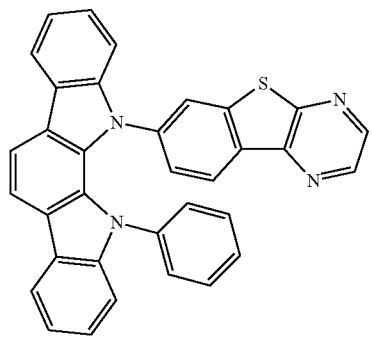
41
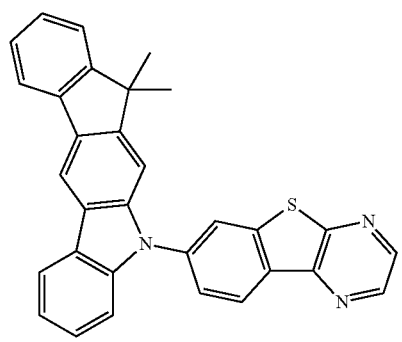
42
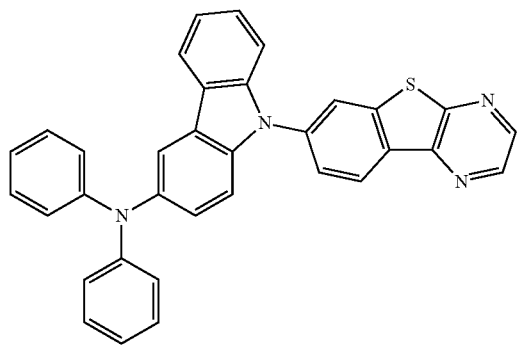
43
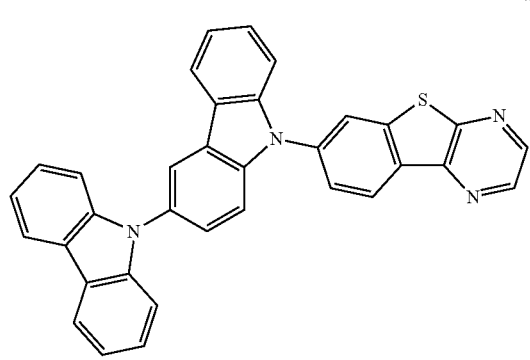
44
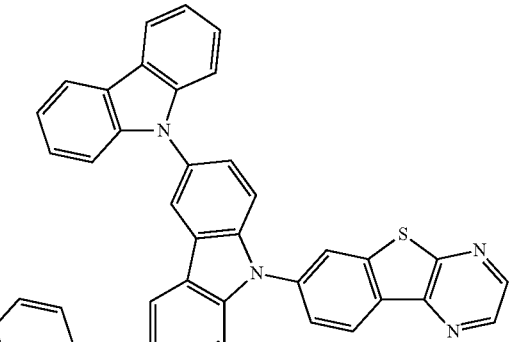
45
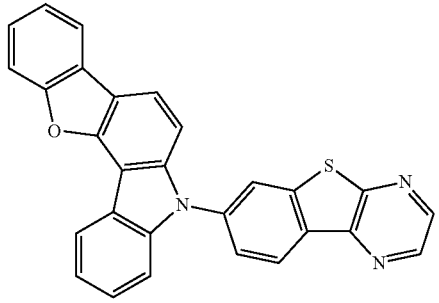
46
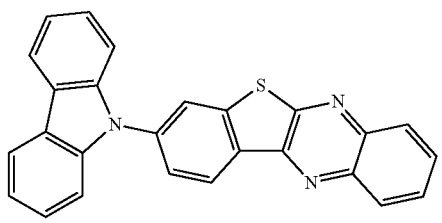
47
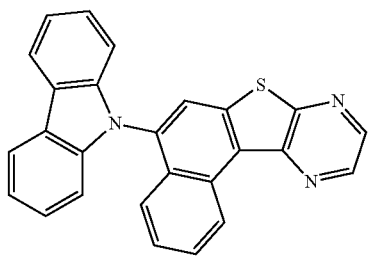
48
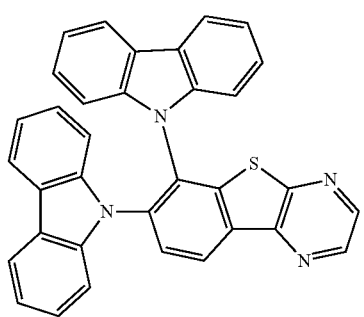

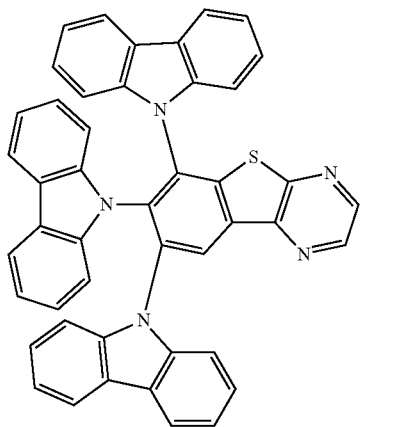
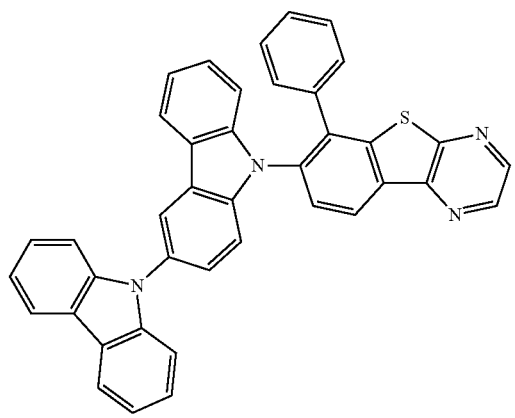
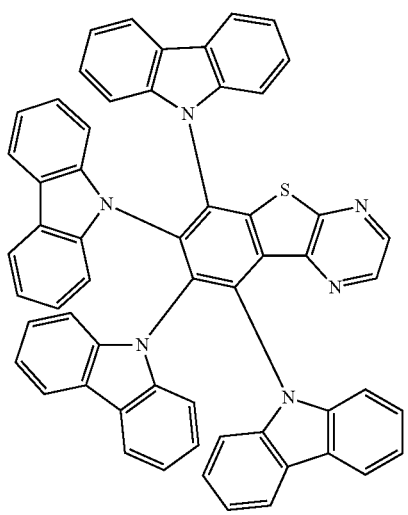
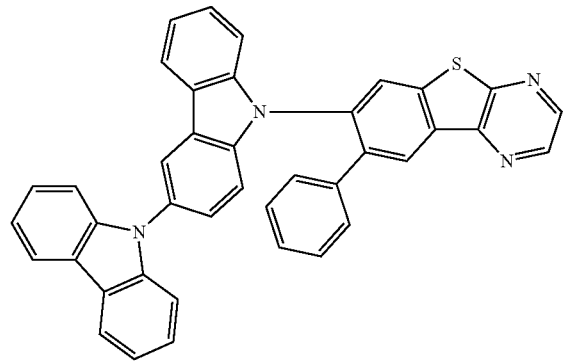
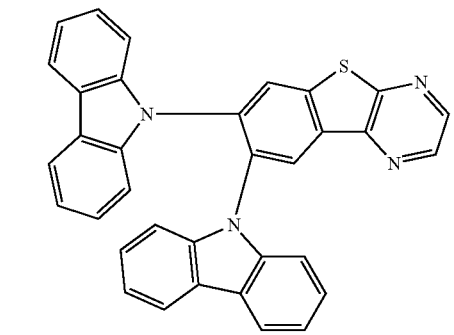
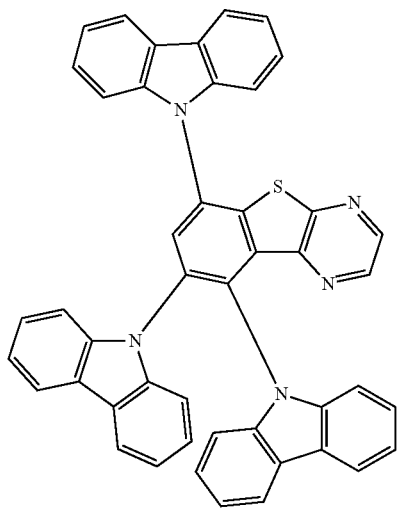
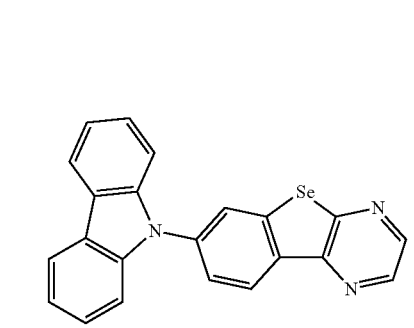

56
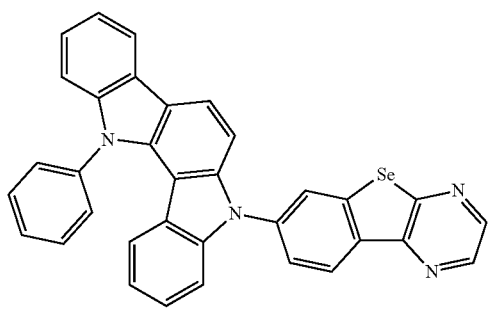
57
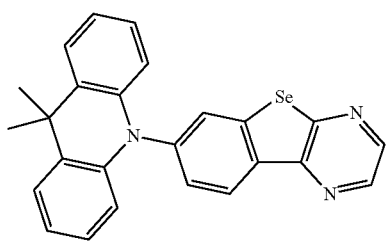
58
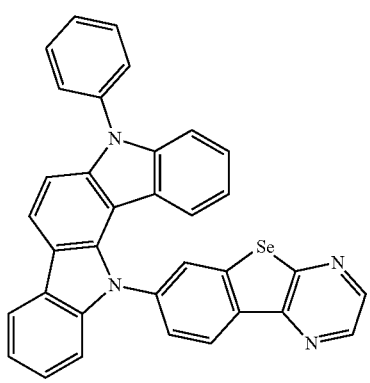
59
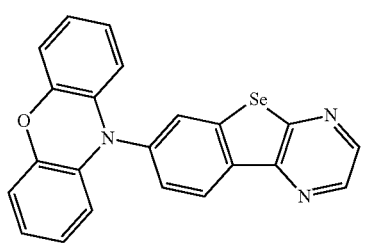
60
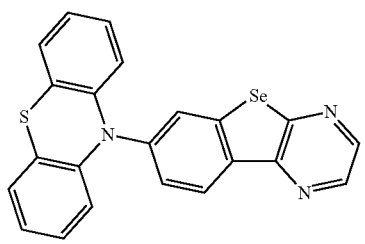
61
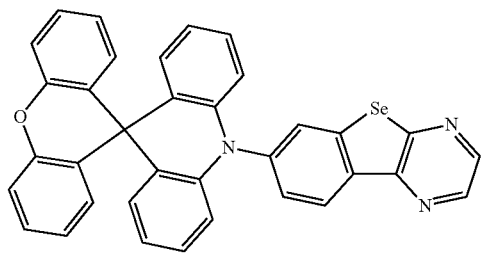
62
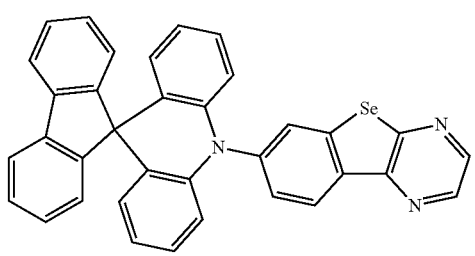
63
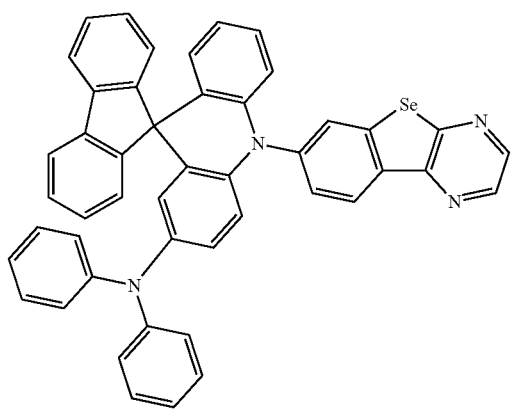
64
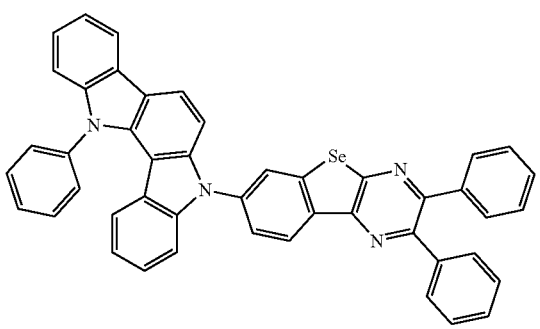

65
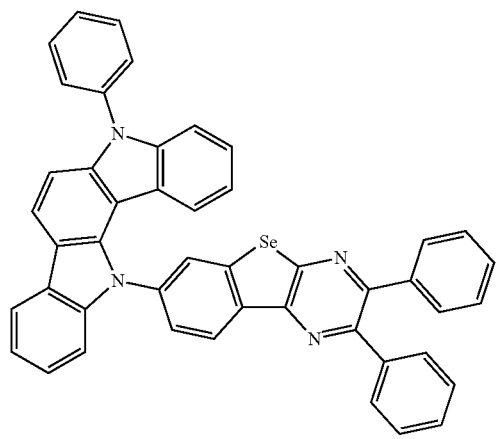
66
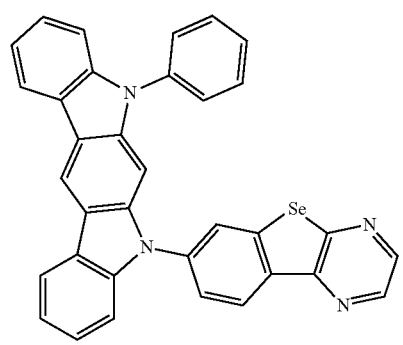
67
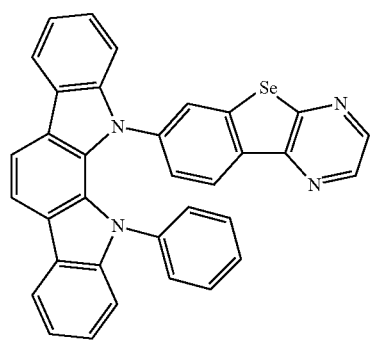
68
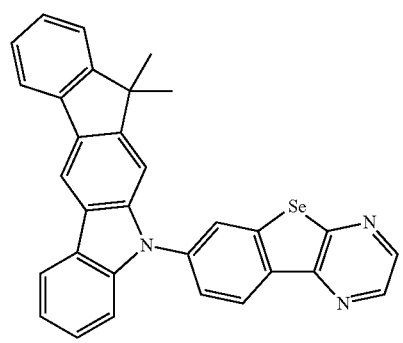
69
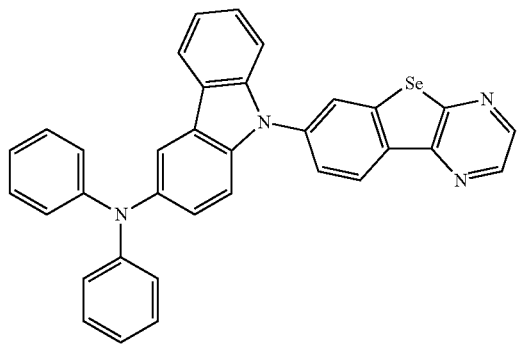
70
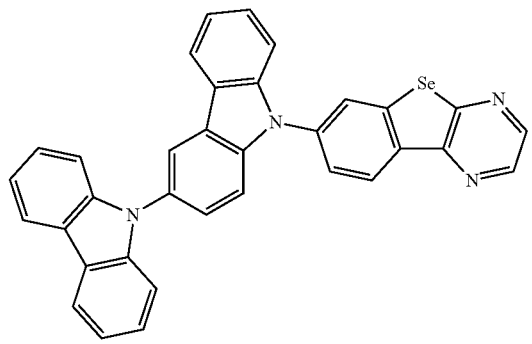
71
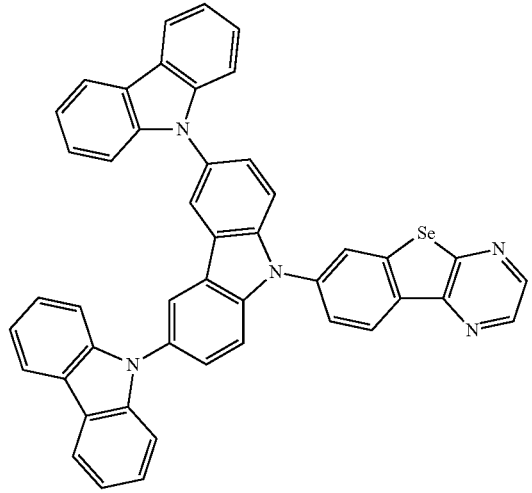
72
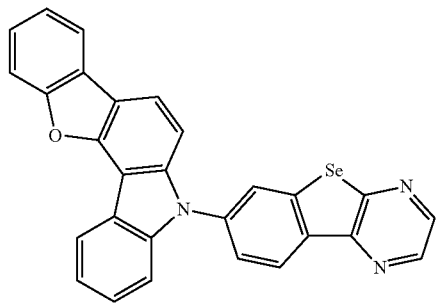

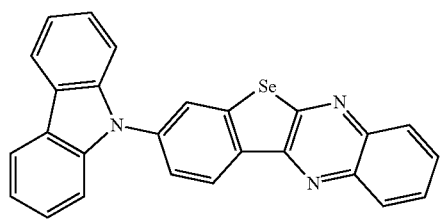
73
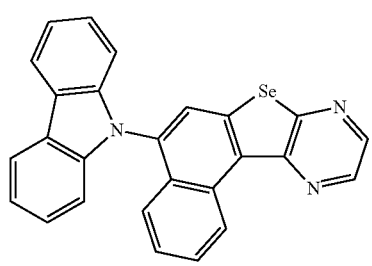
74
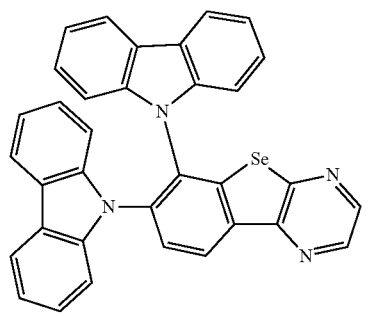
75
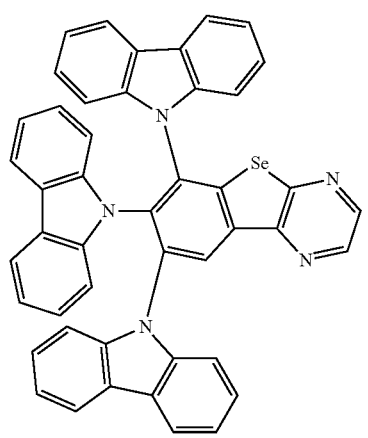
76
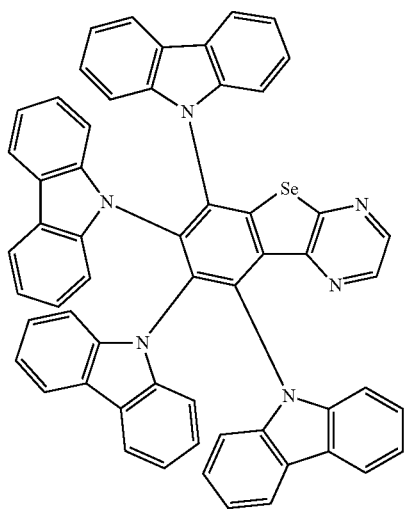
77
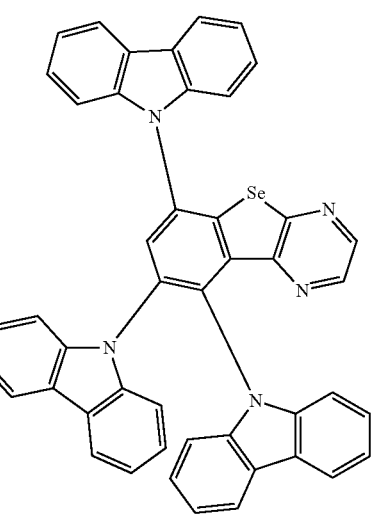
78
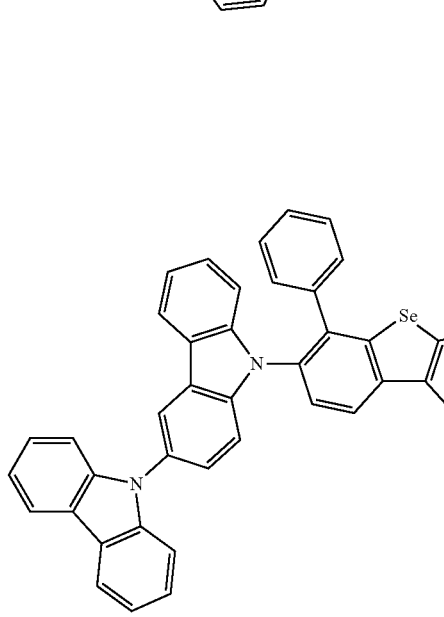
79

80
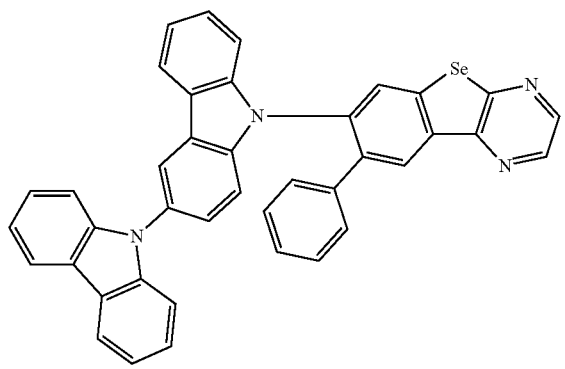
81
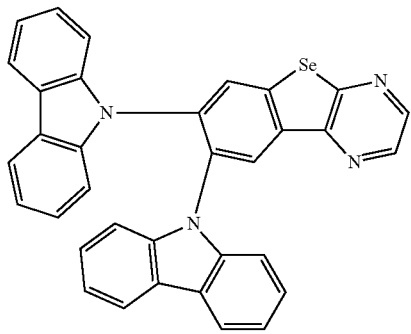
82
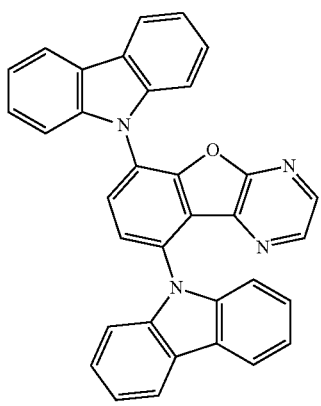
83
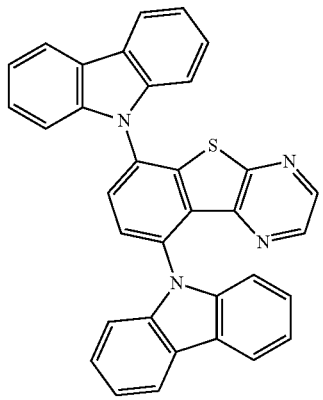
84
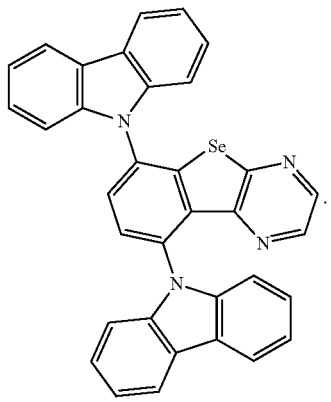
* * * * *